US011938187B2

(12) United States Patent
Lo et al.

(10) Patent No.: US 11,938,187 B2
(45) Date of Patent: Mar. 26, 2024

(54) METHODS AND COMPOSITIONS FOR SYNTHESIS OF TWO-PHOTON CLEAVABLE PHOSPHORAMIDITE MOLECULES FOR OLIGONUCLEOTIDE CONJUGATION

(71) Applicant: City University of Hong Kong, Kowloon (HK)

(72) Inventors: Peggy Pik Kwan Lo, Kowloon (HK); Ling Sum Liu, Kowloon (HK); Dick Yan Tam, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 245 days.

(21) Appl. No.: 17/344,920

(22) Filed: Jun. 10, 2021

(65) Prior Publication Data
US 2023/0000983 A1    Jan. 5, 2023

(51) Int. Cl.
*A61K 41/00* (2020.01)
*A61K 31/713* (2006.01)
*A61K 47/54* (2017.01)
*C07F 9/24* (2006.01)

(52) U.S. Cl.
CPC ........ *A61K 41/0042* (2013.01); *A61K 31/713* (2013.01); *A61K 47/54* (2017.08); *C07F 9/242* (2013.01)

(58) Field of Classification Search
CPC ... A61K 41/0042; A61K 31/713; A61K 47/54
USPC ............... 435/6.1, 91.1, 91.31, 455, 458; 514/44 A; 536/23.1, 24.5
See application file for complete search history.

(56) References Cited

PUBLICATIONS

Gug et al (Angew. Chem. Int. Ed., vol. 47, No. 49, pp. 9525-9529 (2008)) (Year: 2008).*
Dai et al (Small, vol. 11, No. 33, pp. 4990-4996 (2015)) (Year: 2015).*

* cited by examiner

*Primary Examiner* — Jane J Zara
(74) *Attorney, Agent, or Firm* — Conley Rose, P.C.; Michael W. Piper; Andrew M. Metrailer

(57) ABSTRACT

The syntheses of two phosphoramidite building blocks based on BNSF and BNSMB structures are disclosed. Furthermore, some common molecular intermediates have been designed and linked to the central biphenyl core of the two molecules, resulting in a versatile and cost-effective design. These compounds can be effectively introduced to DNA oligonucleotides via the well-established standard cyanoethylphosphoramidite chemistry on the nucleic acid synthesizer. Fragmentation of these BNSF- and BNSMB-functionalized DNA strands is achieved by both one-photon and two-photon photolysis of photoliable bonds of [2-(2-nitrophenyl)propoxy]carbonyl groups on BNSF and BNSMB molecules respectively, resulting in two short pieces of single-stranded DNAs. The versatile design and facile synthesis of these two-photon photocleavage phosphoramidite molecules are beneficial to synthetic chemists and photochemists for the development of new caged compounds which enables to introduce into oligonucleotides as light-triggered carriers via solid-phase synthesis for a wide range of applications in materials science, polymer, chemistry, biology and DNA nanoecthnology.

3 Claims, 50 Drawing Sheets
Specification includes a Sequence Listing.

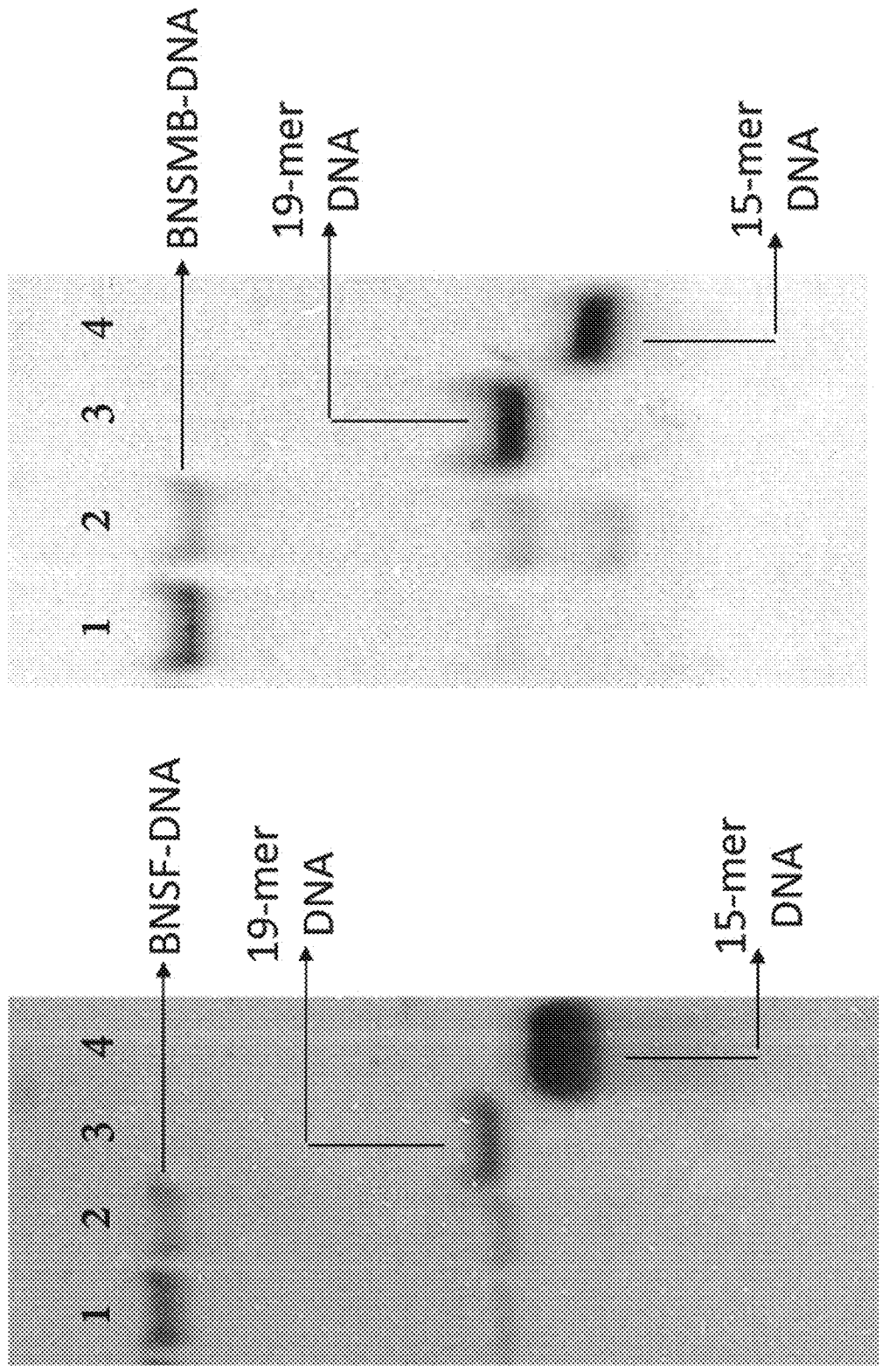

METHODS AND COMPOSITIONS FOR SYNTHESIS OF TWO-PHOTON CLEAVABLE PHOSPHORAMIDITE MOLECULES FOR OLIGONUCLEOTIDE CONJUGATION

INCORPORATION BY REFERENCE OF MATERIAL IN ASCII TEXT FILE

This application incorporates by reference the Sequence Listing contained in the following ASCII text file being submitted concurrently herewith: File name: 470202000_ST25.txt; created on Nov. 19, 2021; and having a files size of 2 KB.

The information in the Sequence Listing is incorporated herein in its entirety for all purposes.

TECHNICAL FIELD

The present disclosure relates to photocleavage and liberation of DNA oligonucleotides. More particularly, the present disclosure relates to photo-release of DNA oligonucleotides by ultraviolet (UV) or near-infrared (NIR) lights.

BACKGROUND

Photo-release of functionalized molecules is a tool to manipulate bioactivities. While the photo-cleavable molecules have been extensively studied, along with the applications on drug delivery, functionalization of pro-drugs and activation of proteins, the significant application on photo-release of DNA oligonucleotides is often overlooked.

SUMMARY

In a first aspect, the invention proposes a method of preparing a phosphoramidite building block comprising: preparing 2-(2-methoxyethoxy)ethyl 4-methylbenzenesulfonate; converting 2-(2-methoxyethoxy)ethyl 4-methylbenzenesulfonate) to 2,7-dibromo-9,9-bis(2-(2-methoxyethoxy)ethyl)-9H-fluorene; converting 2,7-dibromo-9,9-bis(2-(2-methoxyethoxy)ethyl)-9H-fluorene to 9,9-bis(2-(2-methoxyethoxy)ethyl)-2,7-divinyl-9H-fluorene; converting 9,9-bis(2-(2-methoxyethoxy)ethyl)-2,7-divinyl-9H-fluorene to (E)-2-(3-(1-(bis(4-methoxyphenyl)(phenyl)methoxy)propan-2-yl)-4-nitrostyryl)-9,9-bis(2-(2-methoxyethoxy)ethyl)-7-vinyl-9H-fluorene; converting (E)-2-(3-(1-(Bis(4-methoxyphenyl)(phenyl)methoxy)propan-2-yl)-4-nitrostyryl)-9,9-bis(2-(2-methoxyethoxy)ethyl)-7-vinyl-9H-fluorene to 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propan-1-ol; and converting 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propan-1-ol to 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propyl (2-cyanoethyl) diisopropylphosphoramidite.

In a second aspect, the invention proposes a method of making a phosphoramidite building block comprising: preparing 4,4'-dibromo-3,3'-dimethoxy-1,1'-biphenyl; converting 4,4'-dibromo-3,3'-dimethoxy-1,1'-biphenyl to 3,3'-dimethoxy-4,4'-divinyl-1,1'-biphenyl converting 3,3'-dimethoxy-4,4'-divinyl-1,1'-biphenyl to E)-4-(3-(1-(bis(4-methoxyphenyl)(phenyl)methoxy)propan-2-yl)-4-nitrostyryl)-3,3'-dimethoxy-4'-vinyl-1,1'-biphenyl converting E)-4-(3-(1-(bis(4-methoxyphenyl)(phenyl)methoxy)propan-2-yl)-4-nitrostyryl)-3,3'-dimethoxy-4'-vinyl-1,1'-biphenyl to 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propan-1-ol; and converting 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propan-1-ol to 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl (2-cyanoethyl) diisopropylphosphoramidite.

Furthermore, in a further aspect, the invention proposes the further step of conjugating the phosphoramidite building block to a biomolecule to form a conjugated agent.

In yet a further aspect, the invention proposes a composition comprising: (i) a 2,7-bis-(4-nitro-8-(3-(2-propyl)-styryl))-9,9-bis-(1-(3,6-dioxaheptyl))-fluorene (BNSF) group, or a 4,4'-bis-(8-(4-nitro-3-(2-propyl)-styryl))-3,3'-dimethoxybiphenyl (BNSMB) group; and (ii) a biomolecule selected from the group consisting of therapeutic agent, siRNAs, miRNAs, antisense oligonucleotides, nucleotides, peptides, enzymes, mRNA, DNA or a combination thereof.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIGS. 22A and 22B are PAGE analysis of the photocleavable DNA conjugates upon NIR light (700 nm) irradiation.

DETAILED DESCRIPTION

Figure 1:
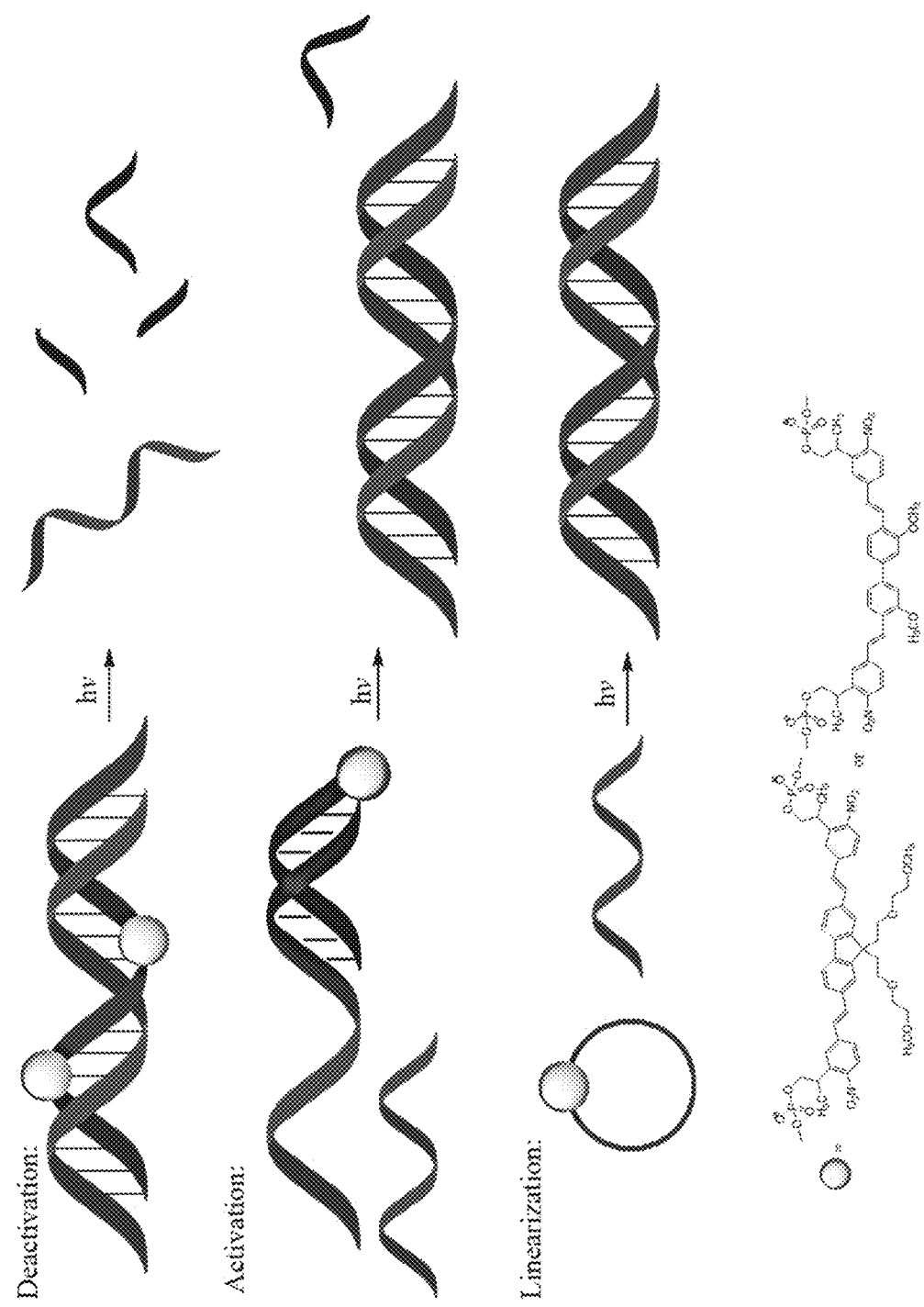
FIG. 1 is a schematic depiction of different modes of photo-modification of functionalized oligonucleotides.

Efforts have been made in the development of conjugated biomolecules where the function and activity of biomolecules is "turned off" before reaching the sites of interest and then turned back "on" in response to an external stimulus. The addition of small molecules or enzymes, pH or temperature variation, ultrasound or magnetic field utilization, and photon irradiation have been used as external stimuli to trigger stimuli-responsive systems switching from "off" to "on" state. Of these methods, photo-control (e.g., photoirradiation) has a number of advantages over other external stimuli as light does not introduce contaminants into the reaction system.

Once a photo-responsive molecule is directly attached to oligonucleotides as a receptor, photo-regulation of the biological process regulated by that biomacromolecule could be achieved. Methods and compositions that function as photoresponsive molecules that can be utilized in the regulation of a biomolecule activity can be useful.

Disclosed herein are methods for the synthesis and utilization of photocleavable molecules (PCM). A PCM of this disclosure may be chemically associated with a functional biomolecule (e.g., bonded). The resultant chemically associated PCM and biomolecule is termed a PCM-biomolecule-conjugate. Herein a PCM refers to a molecule which when exposed to an appropriate source of electromagnetic radiation chemically disassociates from the biomolecule. Chemical disassociation of the PCM, for example by lysis of a chemical bond between the PCM and biomolecule, may allow the biomolecule to express its functionality or activity.

A PCM of the present disclosure comprises a 2,7-bis-(4-nitro-8-(3-(2-propyl)-styryl))-9,9-bis-(1-(3,6-dioxaheptyl))-fluorene (BNSF) group, a 4,4'-bis-(8-(4-nitro-3-(2-propyl)-styryl))-3,3'-dimethoxybiphenyl (BNSMB) group or a combination thereof. In an aspect, BNSF, BNSMB or both are phosphoramidite building blocks. It is to contemplated that the methods disclosed herein are applicable to the introduction of a PCM to a biomolecule (e.g., oligonucleotide); thus, BNSF and BNSMB are exemplary of a methodology that can be more generally applied.

An aspect of a method for the synthesis of BNSF and BNSMB is depicted in Scheme I and further described in the experimental section.

Scheme 1
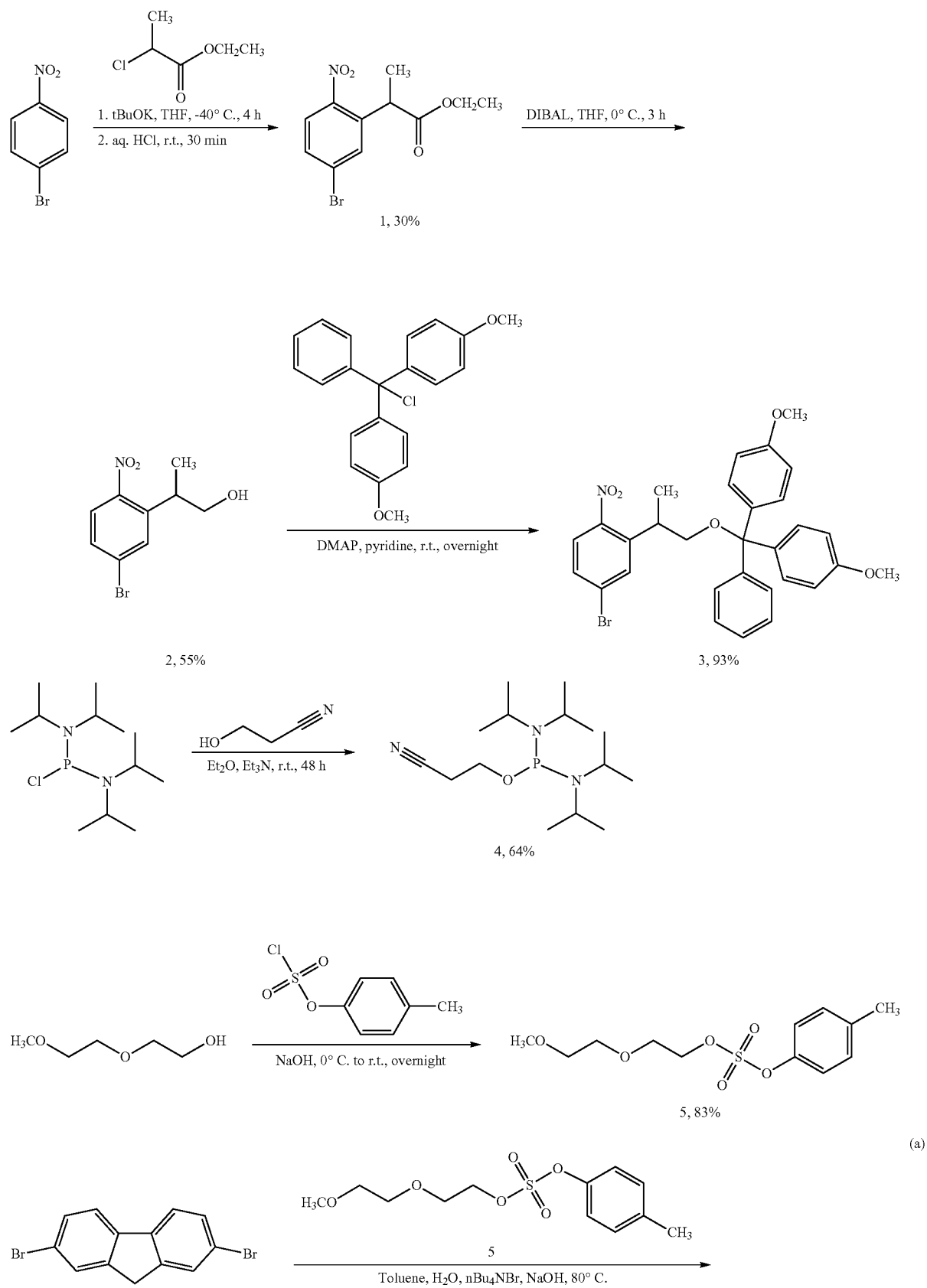

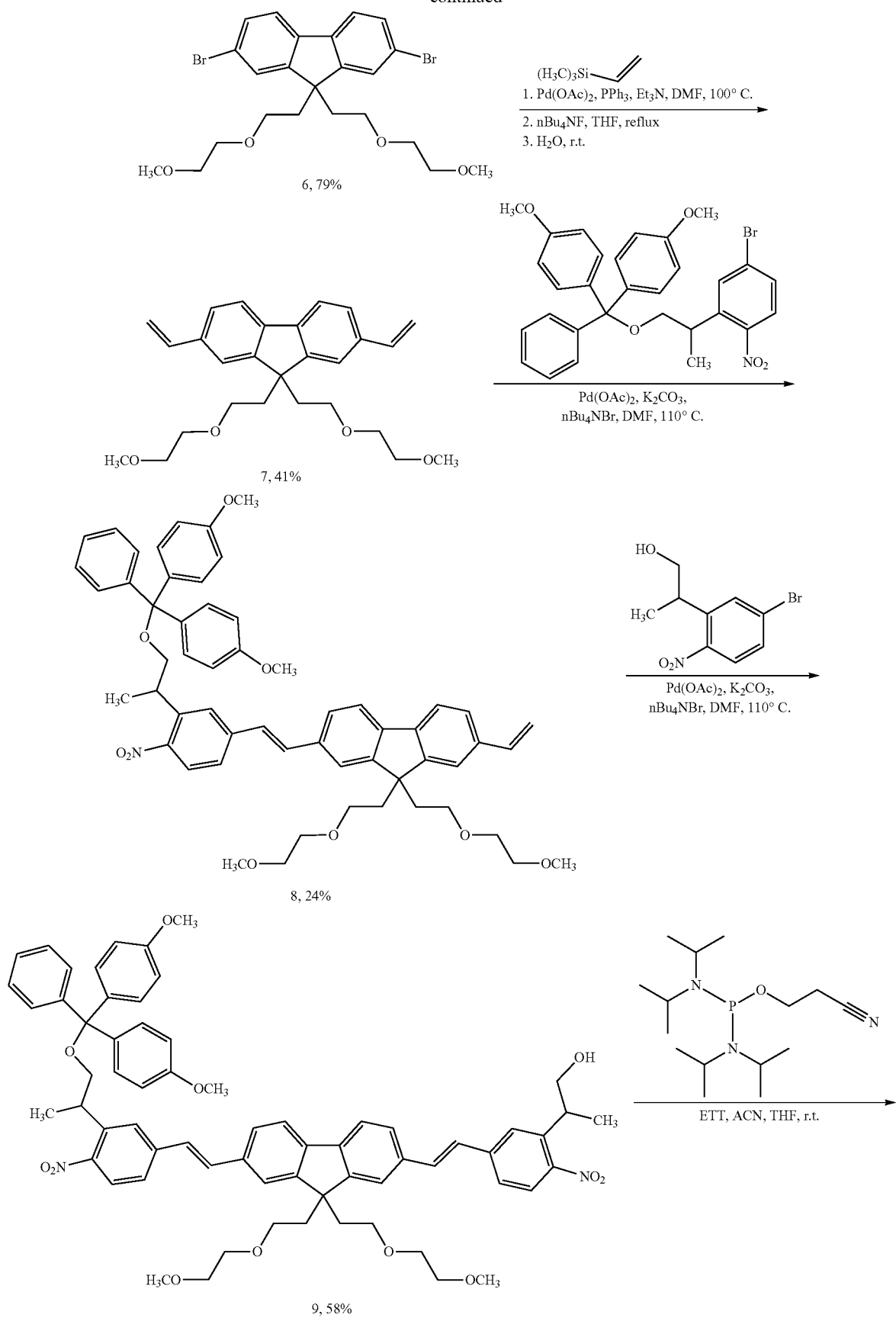

-continued
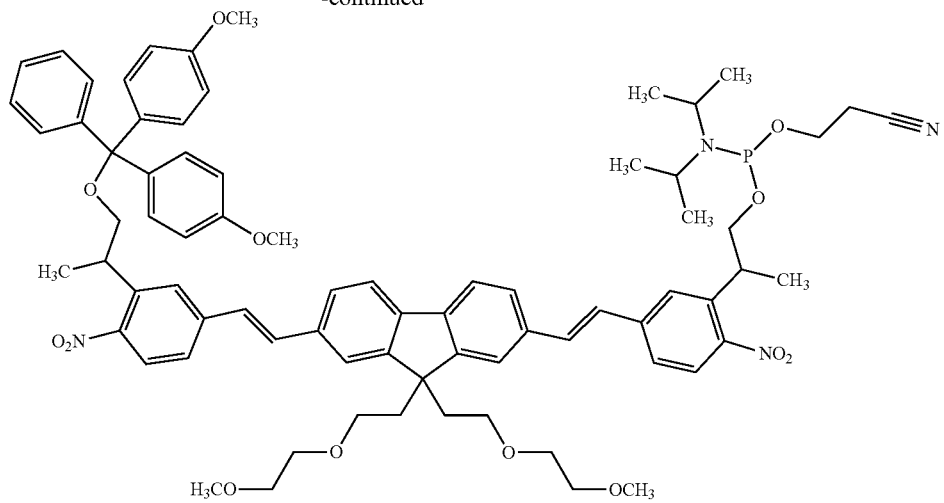
10, 40%
(b)
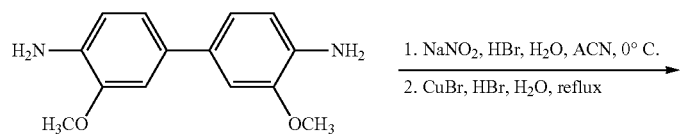
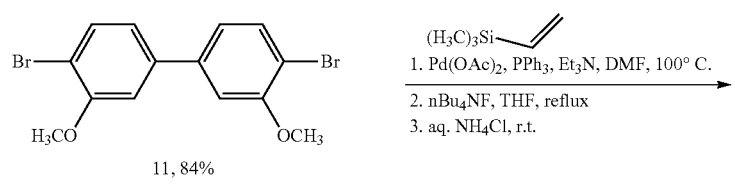
11, 84%
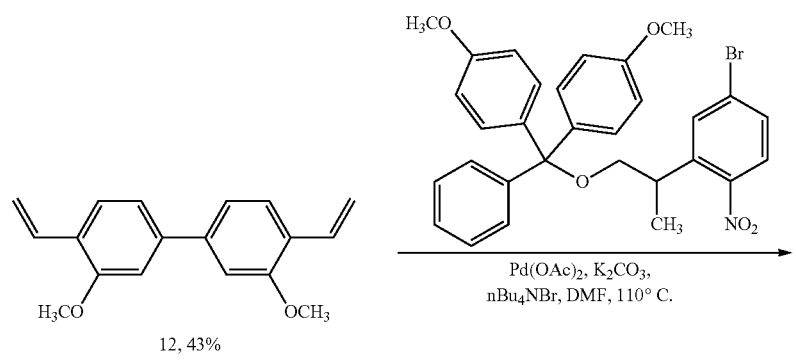
12, 43%

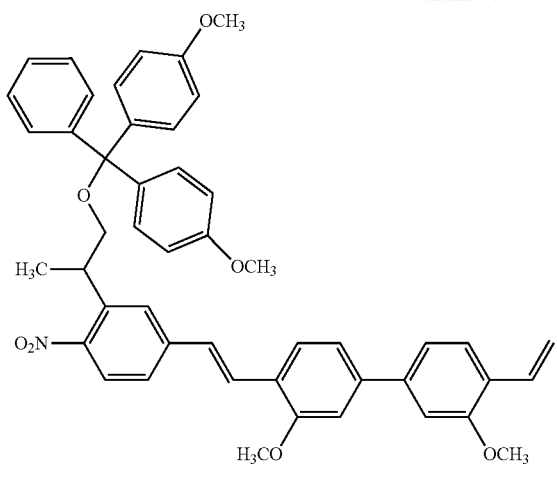
13, 31%
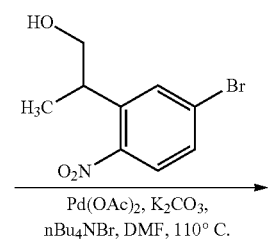
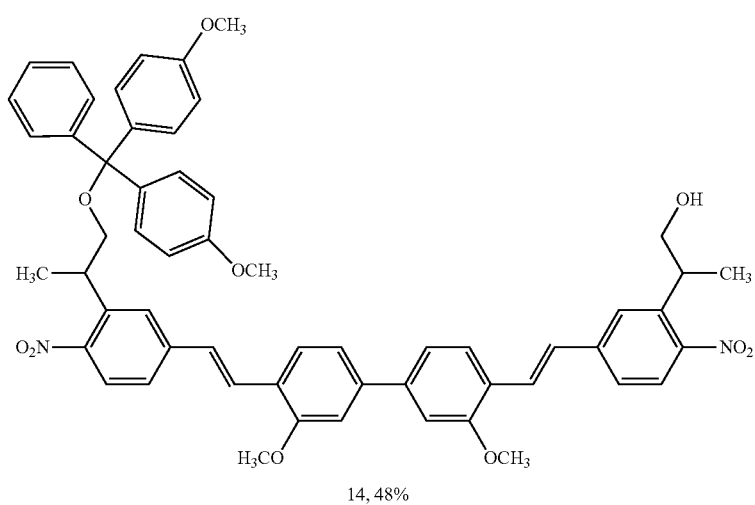
14, 48%
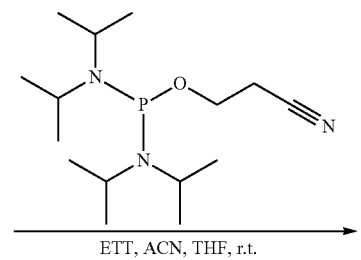
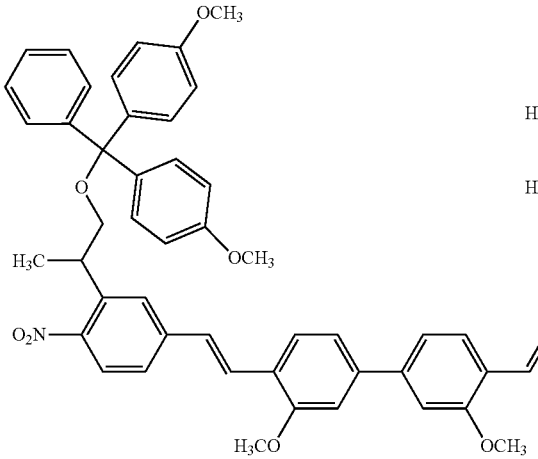
15, 33%

Some common molecular intermediates have been designed and linked to the central biphenyl core of BNSF and BNSMB, resulting in a versatile and cost-effective design. They can be effectively introduced to DNA oligonucleotides via the well-established standard cyanoethylphosphoramidite chemistry on a nucleic acid synthesizer. Additionally, fragmentation of these BNSF- and BNSMB-functionalized DNA strands is achieved by both one-photon and two-photon photolysis of photoliable bonds of [2-(2-nitrophenyl)propoxy]carbonyl groups on the BNSF and BNSMB molecules respectively, resulting in two short pieces of single-stranded DNAs. The versatile design and facile synthesis of these two-photon photocleavage phosphoramidite molecules are beneficial to synthetic chemists and photochemists for the development of new caged compounds. These methodologies may enable the introduction of oligonucleotides as light-triggered carriers via solid-phase synthesis for a wide range of applications in materials science, polymer, biology, chemistry and DNA nanotechnology.

The PCM-biomolecule conjugate is photocleavable. The photocleavable property of the PCM is within a two-photon excitation region which is beneficial to biological systems. The two-photon excitation region is a longer wavelength light source with lower energy which would allow for deeper tissue penetration, less photodamage to the living cells/tissues and three-dimensional control with femtoliter resolution.

Furthermore, the present disclosure provides PCMs that can be applied in different linker strategies for regulating oligonucleotide activity with low energy light sources such as near infrared (NIR) light and widely used in biological systems. For example, as depicted in FIG. 1, functional oligonucleotides can be deactivated by photocleavage into smaller fragments (a). In contrast, they can be activated by photo-induced cleavage of an intermolecular inhibitor nucleic acid (b). Alternatively, a circularized oligonucleotide can be activated by photocleavage into a linear, single-stranded oligonucleotide for further action (c).

A PCM-biomolecule conjugate of the type disclosed herein provides for photo-release of materials such as therapeutic agents for disease treatment, siRNAs, miRNAs, and antisense oligonucleotides for light-controlled gene expression. In another aspect, a PCM-biomolecule conjugate of the type disclosed herein provides a building block for self-assembly of photo-responsive DNA-based nanocarriers for precise control over light-triggered drug/CRISPR-Cas9 release in living system for delivery applications/CRISPR editing. Herein CRISPR/Cas9 refers to a system that edits genes by precisely cutting DNA and then letting natural DNA repair processes to take over. In yet another aspect, the PCM-biomolecule conjugate of the present disclosure provides a tool to build light activated logic gate systems for data storage. In yet another aspect, the PCM-biomolecule conjugate provides for immobilization of photocleavable DNA strands on biochip for photopatterning and photolithography. In yet another aspect, a PCM-biomolecule conjugate of the type disclosed herein is a tool for two photon activation and imaging of live tissues The PCM-biomolecule conjugates of the present disclosure may be used in the treatment of a disease or medical condition. Typically, the PCM-biomolecule conjugate is administered in an effective amount to a patient or subject in need thereof. Optionally, the PCM-biomolecule conjugates of this disclosure are prepared into a composition or formulation for administration to a subject.

The PCMs of the present disclosure can be effectively introduced to DNA oligonucleotides via cyanoethylphosphoramidite chemistry using a nucleic acid synthesizer. In an aspect, fragmentation of a PCM (e.g., BNSF- and BNSMB-functionalized DNA strands) is achieved by one-photon photolysis. In an alternative aspect, fragmentation of these PCM (e.g., BNSF- and BNSMB-functionalized DNA strands) is achieved by two-photon photolysis. For example, photolysis of photoliable bonds of the [2-(2-nitrophenyl)propoxy]carbonyl groups on BNSF and BNSMB molecules respectively, resulting in two short pieces of single-stranded DNAs. The versatile design and facile synthesis of these two-photon photocleavage phosphoramidite molecules are beneficial to synthetic chemists and photochemists for the development of new caged compounds which enables to introduce into oligonucleotides as light-triggered carriers via solid-phase synthesis for a wide range of applications in materials science, polymer, biology, chemistry and DNA nanotechnology.

EXAMPLES

The presently disclosed subject matter having been generally described, the following examples are given as particular aspects of the subject matter and to demonstrate the practice and advantages thereof. It is understood that the examples are given by way of illustration and are not intended to limit the specification or the claims in any manner.

General Procedures

All reactions were performed under $N_2$ atmosphere. Except as otherwise noted, all reagents were reagent grade quality and be utilized as received from J&K Scientific, Sigma-Aldrich, Fluorochem, Apollo Scientific or TCI Chemicals. Anhydrous toluene, anhydrous acetonitrile (ACN), anhydrous diethyl ether ($Et_2O$), anhydrous tetrahydrofuran (THF), anhydrous pyridine and anhydrous dimethylformamide (DMF) were purchased and utilized as received from J&K Scientific or Sigma-Aldrich. Deuterated solvents were used as received from J&K Scientific or Sigma-Aldrich. All other solvents were technical grade unless specified. Column chromatography was performed using 60 Å 40-63-micron silica media (purchased from DAVISIL) as the solid support. The progress of column chromatography was monitored by Merck Millipore TLC silica gel 60 F254 plates, and the elutes were visualized under 254 nm and/or 365 nm UV lamp. Acetic acid, urea, boric acid, ethylenediaminetetraacetic acid disodium salt dihydrate (EDTA), formamide, tris(hydroxymethyl)aminomethane (Tris), (3-aminopropyl)trimethoxysilane, N,N,N',N'-tetramethylethylenediamine, ammonium persulfate, glycerol were used as purchased from Aldrich. 40% acrylamide/bis-acrylamide solution (19:1) was purchased from Bio-Rad. 1000 Å nucleoside-derivatized LCAA-CPG solid support with loading densities of 25-40 μmol/g, 1-[(2-cyanoethyl)-(N,N-diisopropyl)]-phosphoramidite and reagents used for automated DNA synthesis were purchased from BioAutomation. Sephadex G-25 (super fine DNA grade) was used as purchased from Amersham Biosciences. 1 X TBE buffer was composed of 90 mM Tris and boric acid, 1.1 mM EDTA, with a pH of ~8.2. All reagents were reagent grade quality and used as received from J&K (China), unless otherwise indicated.

Instrumentation

All NMR spectra were recorded on Bruker Ascend AVANCE III HD (BBO probe) 600 MHz NMR spectrometer, Bruker AVANCE III (BBO probe) 400 MHz NMR spectrometer or Bruker AVANCE III HD (BBO Probe) 300 MHz NMR spectrometer. $^1$H NMR and $^{13}$C NMR chemical shifts were reported in δ units, parts per million (ppm) relative to the chemical shift of residual solvents. $^{31}$P NMR chemical shifts are reported in δ units, parts per million, relative to the 85% phosphoric acid as the internal standard. Matrix-assisted laser desorption/ionization time of flight (MALDI-TOF) mass spectrometry was performed on ABI 4800 Plus MALDI TOF/TOF mass spectrometers. Anhydrous solvents for reactions were purified by a PureSolv MD5 solvent purification system. Standard automated oligonucleotide solid-phase synthesis was performed on Bio-Automation MerMade MM6 DNA synthesizer. UV/vis measurements were carried out on NanoDrop™ One (Thermofisher). Gel electrophoresis experiments were carried out on an acrylamide 20×20 cm Maxi Vertical electrophoresis apparatus (MV-20DSYS).

HPLC analysis was performed on a set up connecting a Waters 1525 pump to a Waters 2998 Photodiode Array detector. UV/Vis measurements were carried out on Nano-Drop™ One (Thermofisher). UV/Vis photolysis at 365 nm was performed using 8 W handheld UV lamp. (Spectroline, ENF-280C/12). Photolysis at 405 nm was performed using Laser Confocal Scanning Microscope (Leica TCS SPE) with magnification of 10× with a glass 384 well plate. Photolysis at 700 nm was performed using Laser Confocal Scanning Microscope (Leica TCS SP5) with magnification of 10× with a glass 384 well plate. Gel electrophoresis experiments were carried out on an acrylamide 20×20 cm Maxi Vertical electrophoresis apparatus (MV-20DSYS). The mass spectra were measured with ABI/MDS SCIEX 5800 MALDI TOF-TOF by Linear mode. DHAP in 70% methanol was used as matrix.

Synthesis of BNSF and BNSMB Phosphoramidites

Ethyl 3-(5-bromo-2-nitrophenyl)butanoate (1)

Potassium tert-butoxide (1.33 g, 11.8528 mmol, 239 mol %) was dissolved in anhydrous THF (10 mL) and then cooled to −40° C. In a separated flask, 1-bromo-4-nitrobenzene (1.0 g, 4.9502 mmol, 100 mol %) and ethyl 2-chloropropionate (0.8 mL, 6.2791 mmol, 127 mol %) were dissolved in anhydrous THF (8 mL). This reaction mixture was cooled to 0° C. and then transferred to the potassium tert-butoxide solution by cannula. The reaction mixture was stirred at −40° C. for 4 h. After that, the reaction mixture was warmed to room temperature. Aqueous HCl solution (1 M, 17 mL) was added and the reaction mixture was stirred for 30 min at room temperature. The product was extracted by DCM (3×200 mL). The organic phases were collected and dried over $Na_2SO_4$. The crude product was concentrated under reduced pressure and purified on a silica gel column, gradient eluting with 10-50% DCM in n-hexane. The solvent was removed under reduced pressure and the product was obtained as a brown liquid 1 (0.45 g, 1.4895 mmol, yield=30%).

Figure 2A:
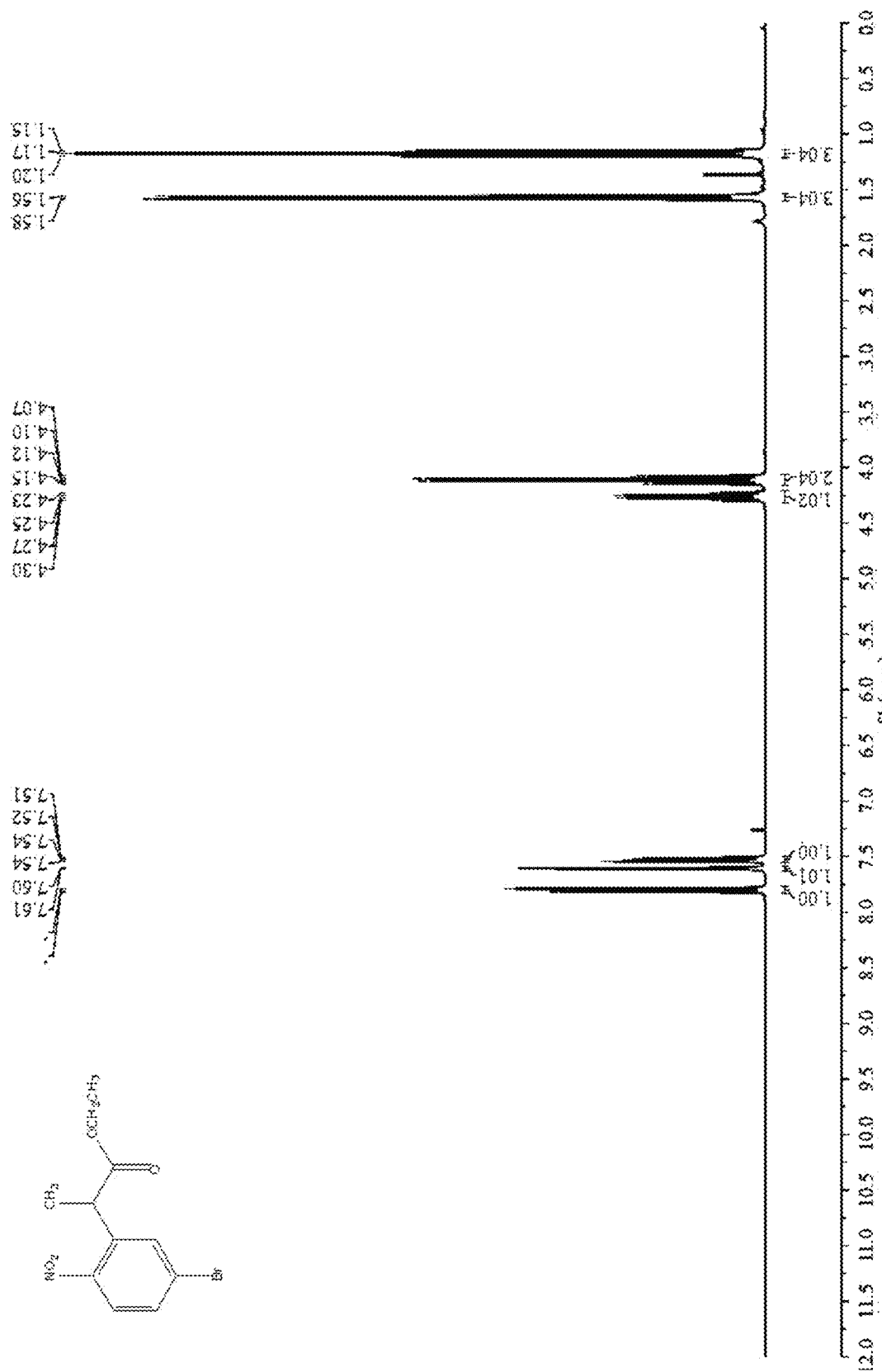
FIG. 2A displays the $^1$H NMR spectra of ethyl-3-5-bromo-2-nitrophenyl)butanoate (1).
Figure 2B:
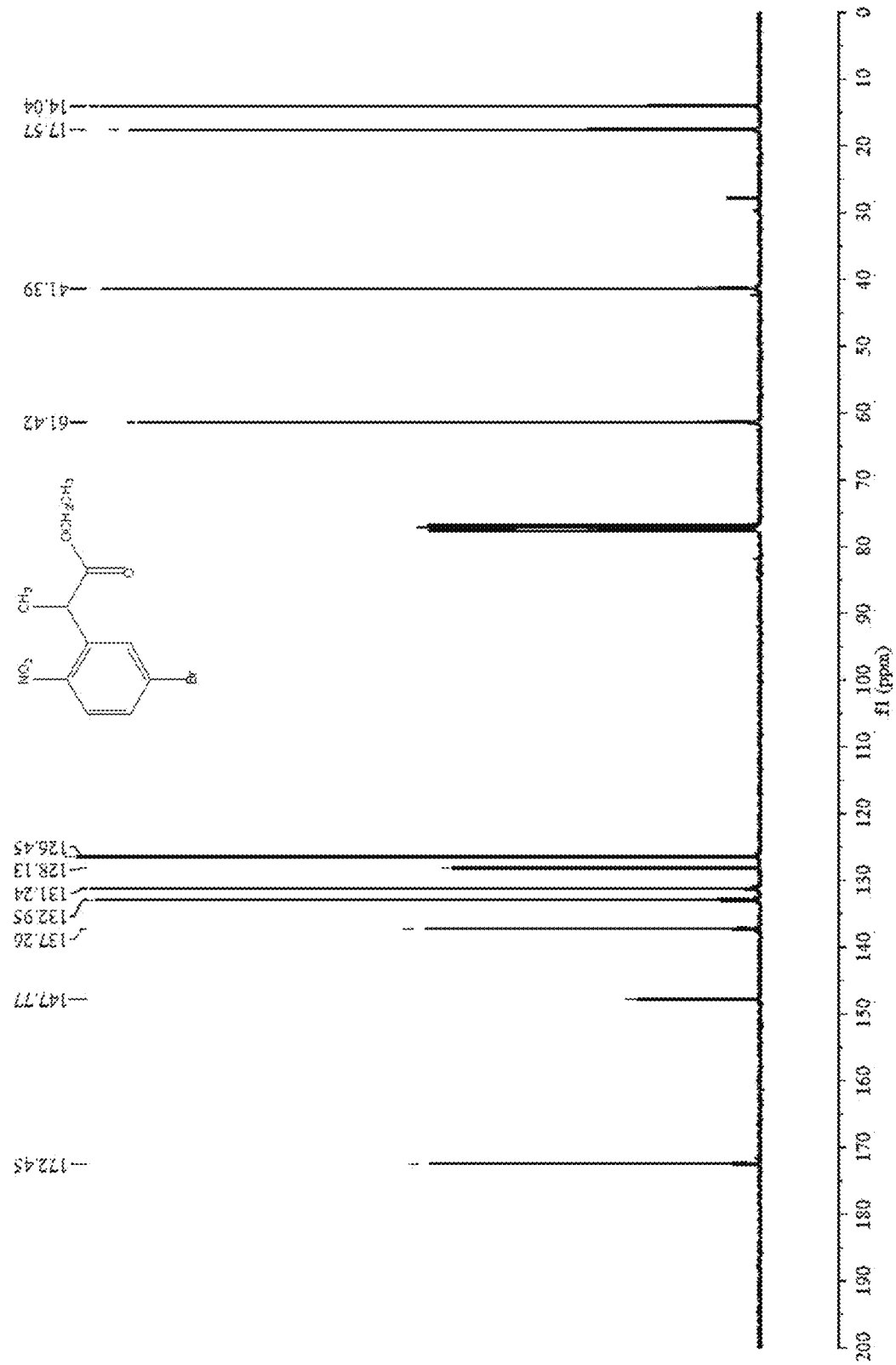
FIG. 2B displays the $^{13}$C NMR spectra of ethyl-3-5-bromo-2-nitrophenyl)butanoate (1).

$^1$H and $^{13}$C NMR spectra of (1) are presented in FIG. 2. $^1$H NMR (300 MHz, CDCl$_3$) δ 7.80 (d, J=8.7 Hz, 1H), 7.61 (d, J=2.1 Hz, 1H), 7.53 (dd, J=8.7, 2.1 Hz, 1H), 4.26 (q, J=7.2 Hz, 1H), 4.11 (q, J=7.1 Hz, 2H), 1.57 (d, J=7.2 Hz, 3H), 1.17 (t, J=7.1 Hz, 3H); $^{13}$C NMR (75 MHz, CDCl$_3$) δ 172.45, 147.77, 137.26, 132.95, 131.24, 128.13, 126.45, 61.42, 41.39, 17.57, 14.04.

2-(5-Bromo-2-nitrophenyl)propan-1-ol (2)

Compound 1 (1.44 g, 5.5365 mmol, 100 mol %) was dissolved in anhydrous THF (40 mL) and then cooled to 0° C. Diisobutylaluminum hydride (1 M in THF, 17 mL, 17 mmol, 307 mol %) was added to the reaction mixture. The reaction mixture was then stirred at 0° C. for 3 h. After that, the reaction mixture was diluted with THF (100 mL) and then aqueous HCl solution (1 M, 25 mL) was added. The reaction mixture was extracted with EtOAc (100 mL×3). The organic phases were collected, combined, and washed with distilled water (30 mL). The crude product was then concentrated under reduced pressure and purified on a silica gel column, isocratic eluting with DCM. The solvent was removed under reduced pressure and the product was obtained as a brown liquid 2 (681 mg, 2.6183 mmol, yield=55%).

Figure 3A:
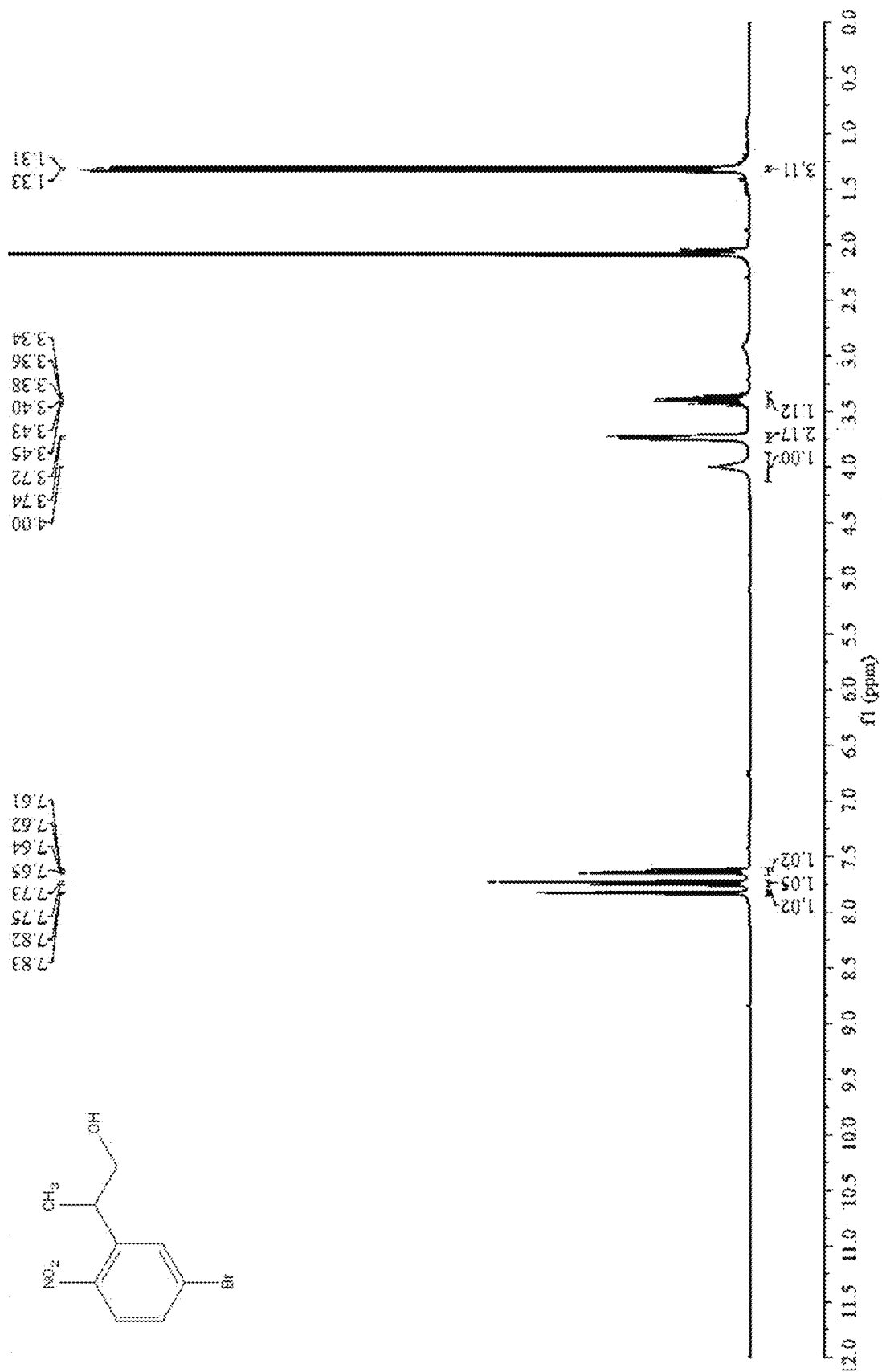
FIG. 3A displays the $^1$H spectra of 2-(5-Bromo-2-nitrophenyl)propan-1-ol (2).
Figure 3B:
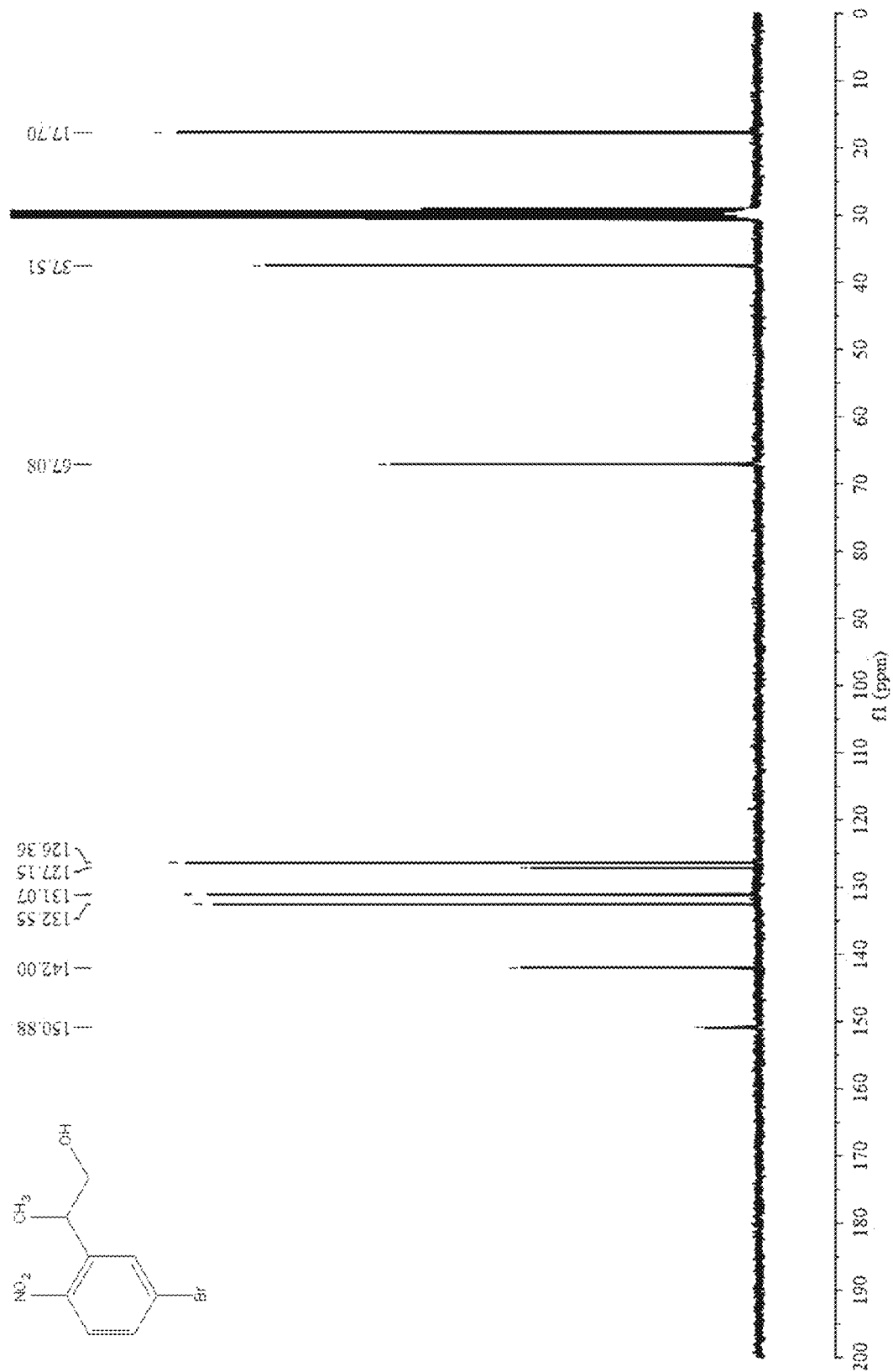
FIG. 3B displays the $^{13}$C spectra of 2-(5-Bromo-2-nitrophenyl)propan-1-ol (2).

$^1$H and $^{13}$C NMR spectra of (2) are presented in FIG. 3. $^1$H NMR (300 MHz, Acetone) δ 7.83 (d, J=2.1 Hz, 1H), 7.74 (d, J=8.6 Hz, 1H), 7.63 (dd, J=8.6, 2.1 Hz, 1H), 4.00 (s, 1H), 3.73 (d, J=6.4 Hz, 2H), 3.47-3.33 (m, 1H), 1.32 (d, J=6.9 Hz, 3H); $^{13}$C NMR (75 MHz, Acetone) δ 150.88, 142.00, 132.55, 131.07, 127.15, 126.36, 67.08, 37.51, 17.70.

4,4'-((2-(5-Bromo-2-nitrophenyl)propoxy)(phenyl)methylene)bis(methoxybenzene) (3)

Figure 4A:
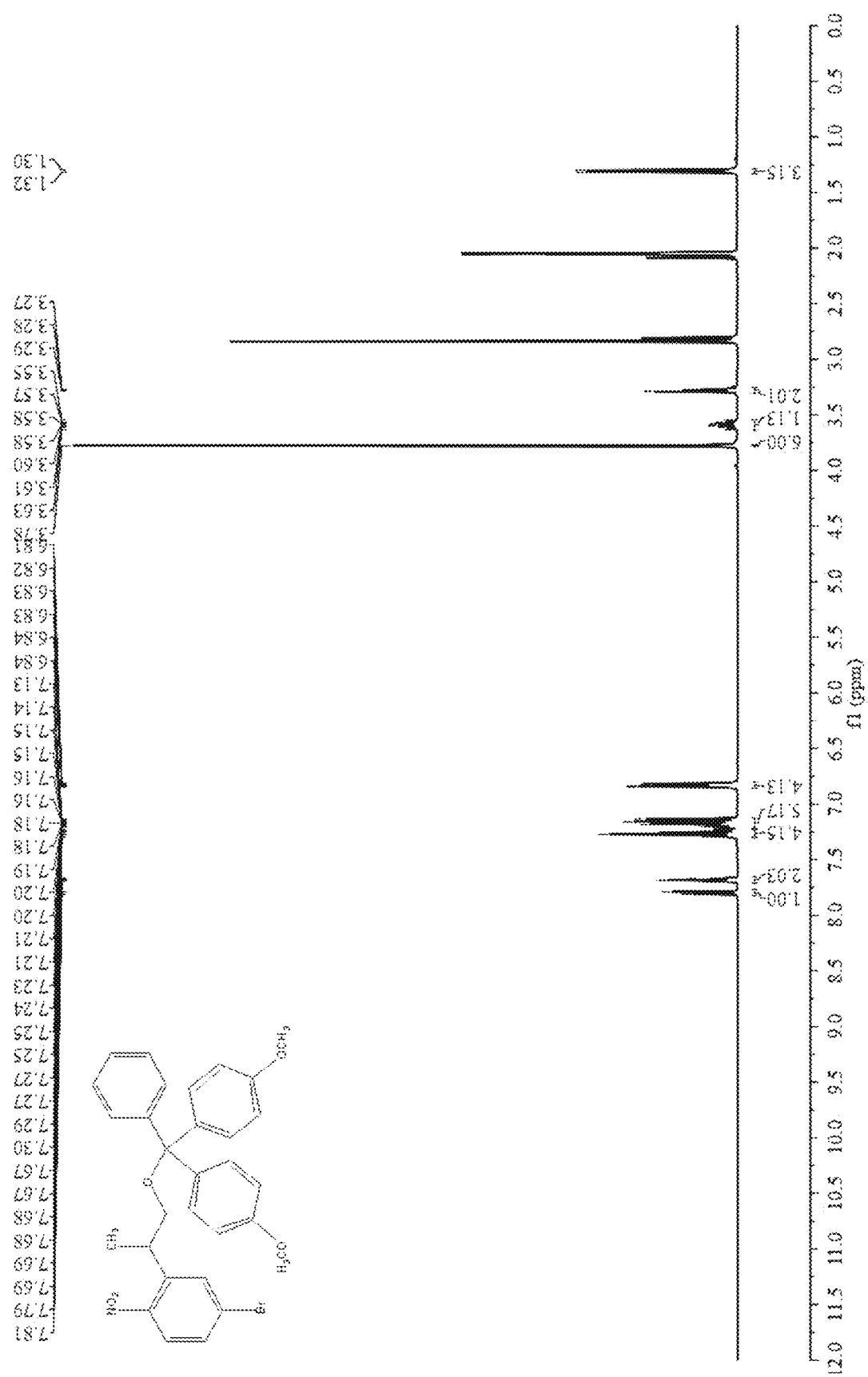
FIG. 4A displays the $^1$H NMR spectra of 4,4'-((2-(5-bromo-2-nitrophenyl)propoxy)(phenyl)methylene)bis(methoxybenzene) (3).
Figure 4B:
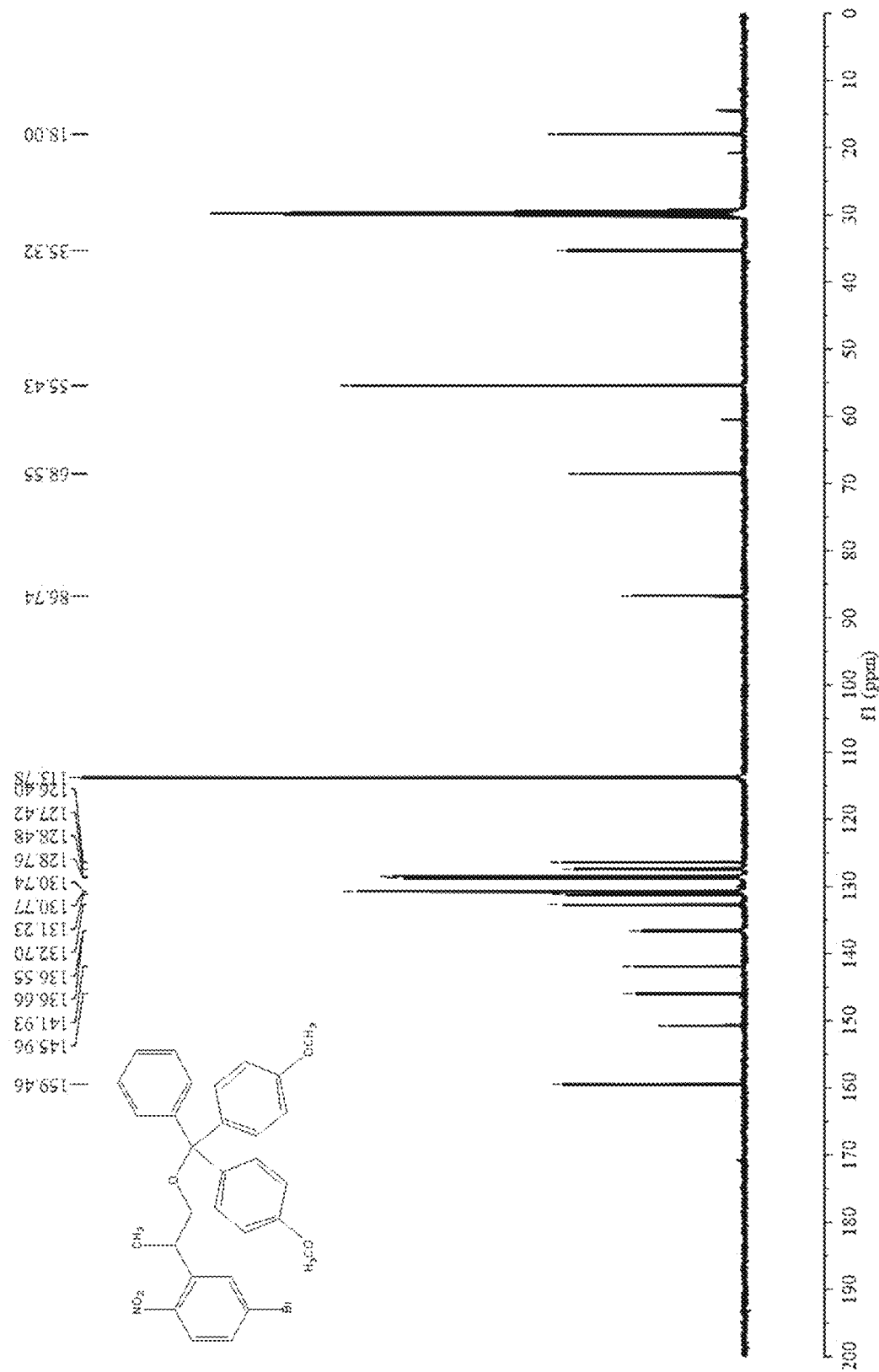
FIG. 4B displays the $^{13}$C NMR spectra of 4,4'-((2-(5-bromo-2-nitrophenyl)propoxy)(phenyl)methylene)bis(methoxybenzene) (3).

Compound 2 (750 mg, 2.8836 mmol, 100 mol %), 4,4'-dimethoxytrityl chloride (1.47 g, 4.3385 mmol, 150 mol %), and 4-dimethylaminopyridine (52.8 mg, 0.4322 mmol, 15 mol %) were stirred in anhydrous pyridine (20 mL) at room temperature for overnight. After that, the volatile materials were removed under reduced pressure. The residue was purified on a silica gel column, isocratic eluting with 80% DCM in n-hexane containing 1% Et$_3$N. The solvent was removed under reduced pressure and the product was obtained as a white solid 3 (1.51 g, 2.6846 mmol, yield=93%). $^1$H and $^{13}$C NMR spectra of (3) are presented in FIG. 4.

$^1$H NMR (400 MHz, Acetone) δ 7.80 (d, J=9.1 Hz, 1H), 7.71-7.65 (m, 2H), 7.31-7.22 (m, 4H), 7.22-7.12 (m, 5H), 6.87-6.79 (m, 4H), 3.78 (s, 6H), 3.64-3.54 (m, 1H), 3.30-3.26 (m, 2H), 1.31 (d, J=7.0 Hz, 3H); $^{13}$C NMR (101 MHz, Acetone) δ 159.46, 150.75, 145.96, 141.93, 136.66, 136.55, 132.70, 131.23, 130.77, 130.74, 128.76, 128.48, 127.42, 127.25, 126.40, 113.78, 86.74, 68.55, 55.43, 35.32, 18.00.

2-Cyanoethyl N,N,N',N'-tetraisopropylphosphorodiamidite (4)

Bis(diisopropylamino)chlorophosphine (5 g, 18.7413 mmol, 100 mol %) was dissolved in anhydrous Et$_2$O (50 mL). 3-Hydroxypropanenitrile (1.8 mL, 26.3365 mmol, 141 mol %) and anhydrous Et$_3$N (5.3 mL, 38.0255 mmol, 203 mol %) were added to the reaction mixture. The reaction mixture was stirred at room temperature for 48 h. The volatile materials were then removed under reduced pressure and the residue was purified on a silica gel column, isocratic eluting with 5% DCM in n-hexane containing 10% Et$_3$N. The solvent was removed under reduced pressure and the product was obtained as a colourless liquid 4 (3.6 g, 11.9439 mmol, yield=64%). The dried product was stored at −20° C. and under N$_2$ atmosphere.

Figure 5A:
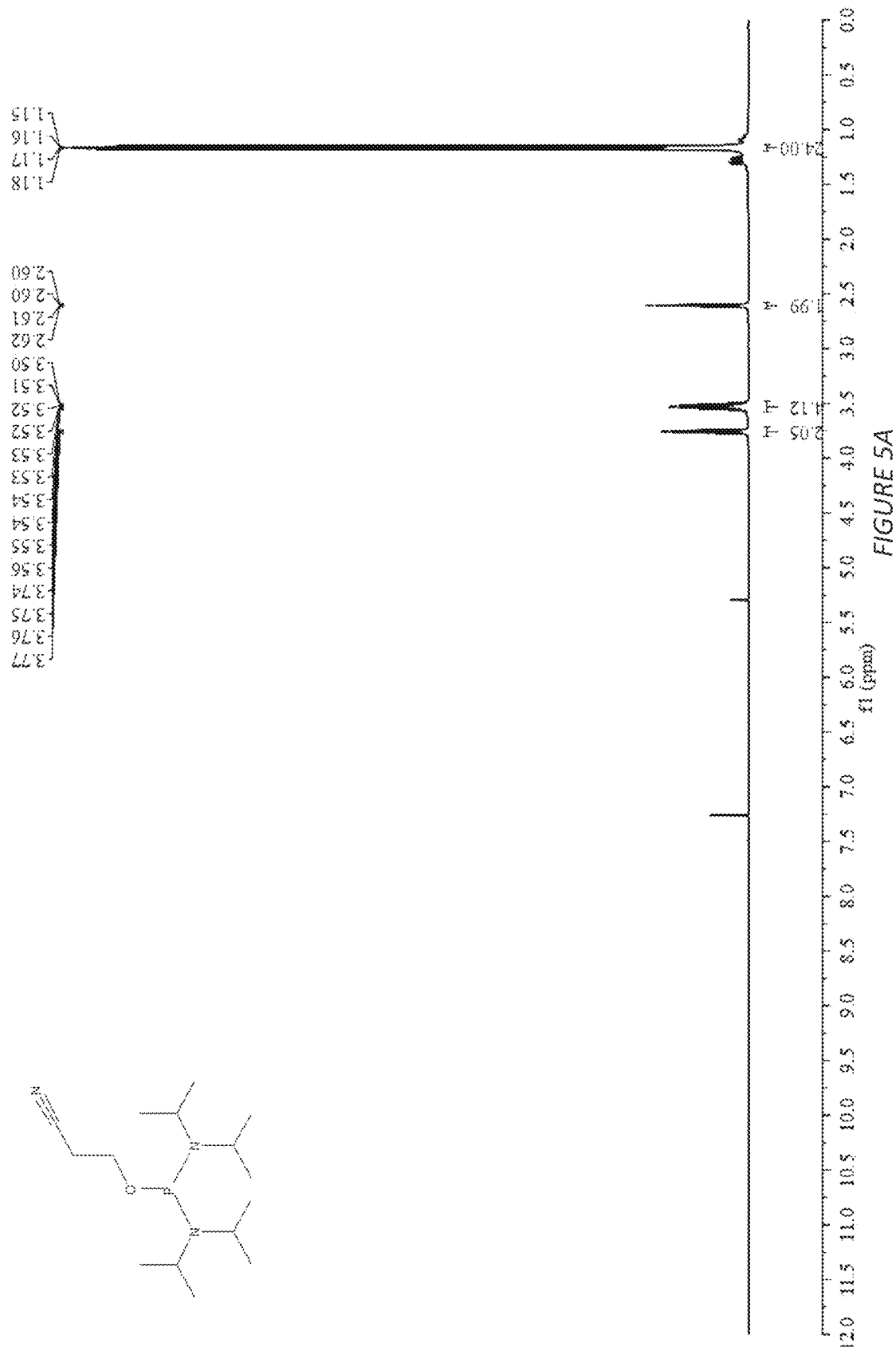
FIG. 5A displays the $^1$H NMR spectra of 2-cyanoethyl, N,N,N',N'-tetraisopropylphosphoramidite (4).
Figure 5B:
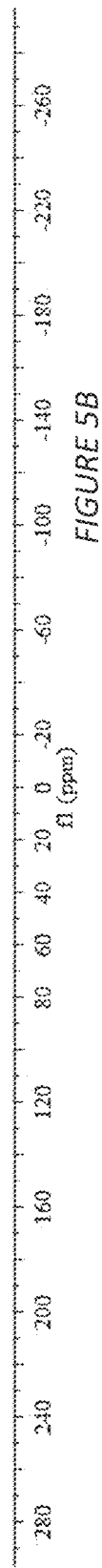
FIG. 5B displays the $^{31}$P NMR spectra of 2-cyanoethyl, N,N,N',N'-tetraisopropylphosphoramidite (4).
Figure 5C:
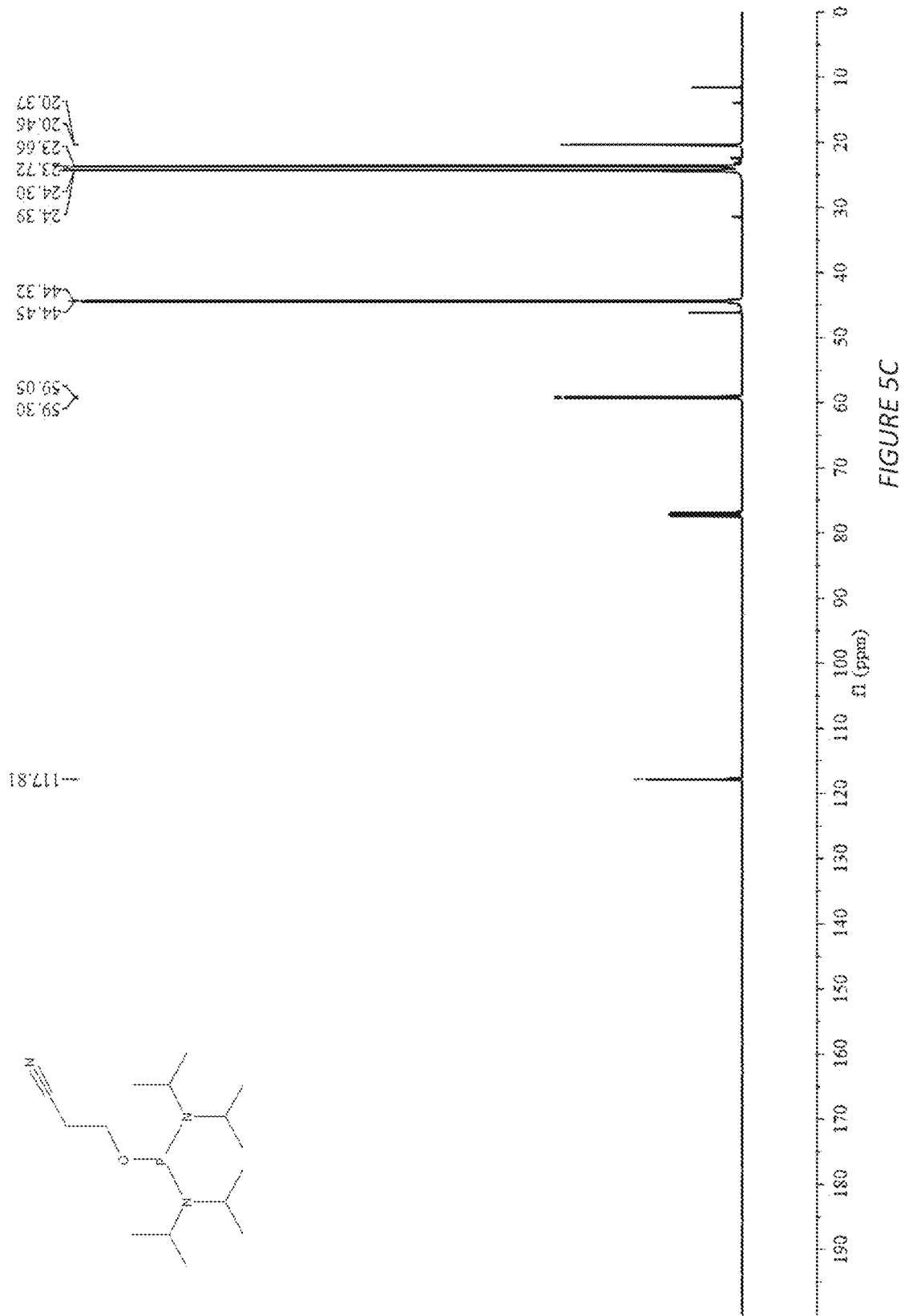
FIG. 5C displays the $^{13}$C NMR spectra of 2-cyanoethyl, N,N,N',N'-tetraisopropylphosphoramidite (4).

$^1$H, $^{31}$P and $^{13}$C NMR spectra of (4) are presented in FIG. 5. $^1$H NMR (600 MHz, CDCl$_3$) δ 3.76 (dd, J=13.7, 6.4 Hz, 2H), 3.58-3.48 (m, 4H), 2.60 (dd, J=9.3, 3.4 Hz, 2H), 1.17 (dd, J=10.0, 6.8 Hz, 24H); $^{31}$P NMR (162 MHz, CDCl$_3$) δ 123.08; $^{13}$C NMR (101 MHz, CDCl$_3$) δ 117.81, 59.30, 59.05, 44.45, 44.32, 24.39, 24.30, 23.72, 23.66, 20.46, 20.37.

2-(2-Methoxyethoxy)ethyl 4-methylbenzenesulfonate (5)

2-(2-Methoxyethoxy)ethanol (10 g, 83.2307 mmol, 100 mol %) was dissolved in anhydrous THF (40 mL) and cooled to 0° C. Sodium hydroxide (5 g, 125 mmol, 151 mol %) was dissolved in distilled water (50 mL) and then added to the reaction mixture. The reaction mixture was stirred for 2 h at 0° C. 4-Toluenesulfonyl chloride (15.8 g, 82.8743 mmol, 100 mol %) was dissolved in anhydrous THF (40 mL) and added to the reaction mixture at 0° C. The reaction mixture was warmed to room temperature and stirred for overnight. After that, the organic layer was separated and collected. The aqueous layer was extracted with chloroform (200 mL×3). The organic phases were combined, and the solvent was removed under reduced pressure. The residue was suspended in DCM (100 mL), and the insoluble material was removed by filtration. The filtrate was concentrated under reduced pressure, and the residue was purified on a silica gel column, isocratic eluting with 30% DCM in n-hexane containing 5% Et$_3$N. The solvent was removed under reduced pressure and the product was obtained as a yellow oil 5 (19 g, 69.2594 mmol, yield=83%).

Figure 6A:
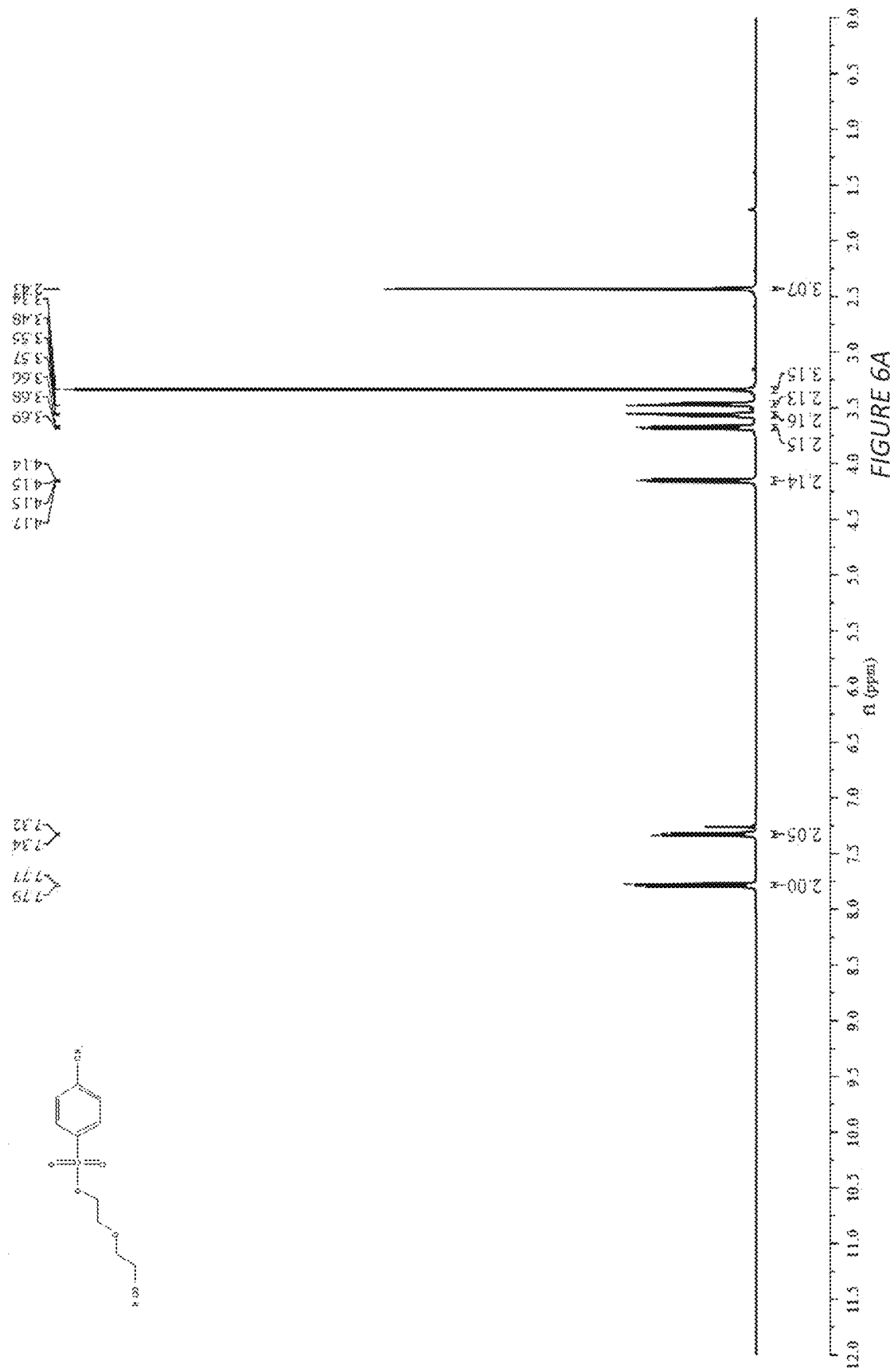
FIG. 6A displays the $^1$H NMR spectra of 2-(2-methoxyethoxy)ethyl 4-methylbenzenesulfonate (5).
Figure 6B:
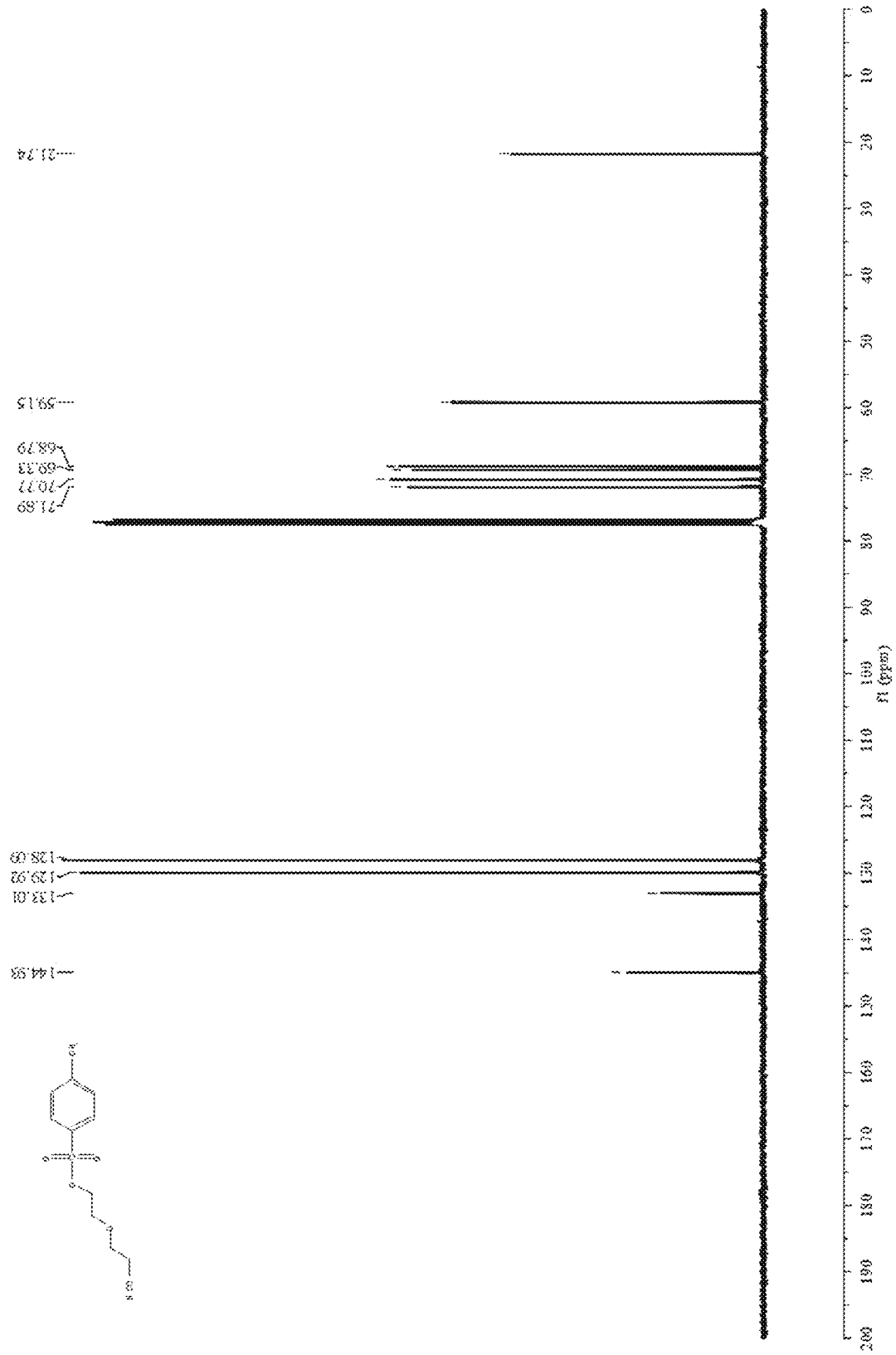
FIG. 6B displays the $^{13}$C NMR spectra of 2-(2-methoxyethoxy)ethyl 4-methylbenzenesulfonate (5).

$^1$H, and $^{13}$C NMR spectra of (5) are presented in FIG. 6. $^1$H NMR (400 MHz, CDCl$_3$) δ 7.78 (d, J=8.3 Hz, 2H), 7.33 (d, J=8.0 Hz, 2H), 4.15 (dd, J=5.4, 4.3 Hz, 2H), 3.68 (dd, J=5.4, 4.4 Hz, 2H), 3.59-3.54 (m, 2H), 3.49-3.44 (m, 2H), 3.34 (s, 3H), 2.43 (s, 3H); $^{13}$C NMR (101 MHz, CDCl$_3$) δ 144.93, 133.01, 129.92, 128.09, 71.89, 70.77, 69.33, 68.79, 59.15, 21.74.

2,7-Dibromo-9,9-bis(2-(2-methoxyethoxy)ethyl)-9H-fluorene (6)

2,7-Dibromo-9H-fluorene (1.56 g, 4.8146 mmol, 100 mol %), compound 5 (4 g, 14.5809 mmol, 302 mol %) and tetrabutylammonium bromide (322 mg, 0.9989 mmol, 21 mol %) were dissolved in anhydrous toluene (30 mL). Sodium hydroxide (3 g, 75 mmol, 1558 mol %) was dissolved in distilled water (12 mL) and then added to the reaction mixture. The reaction mixture was stirred at 80° C. for overnight. After that, the reaction mixture was cooled to room temperature and the organic layer was collected. The solvent was removed under reduced pressure. The residue was suspended in DCM (300 mL), and washed successively with H$_2$O (100 mL), aqueous HCl solution (1 M, 100 mL), H$_2$O (100 mL) and brine (100 mL) and dried over Na$_2$SO$_4$. The crude product was concentrated under reduced pressure and the residue was purified on a silica gel column, gradient eluting with 5-30% EtOAc in n-hexane. The solvent was removed under reduced pressure and the product was obtained as an orange liquid 6 (2.013 g, 3.8105 mmol, yield=79%).

Figure 7A:
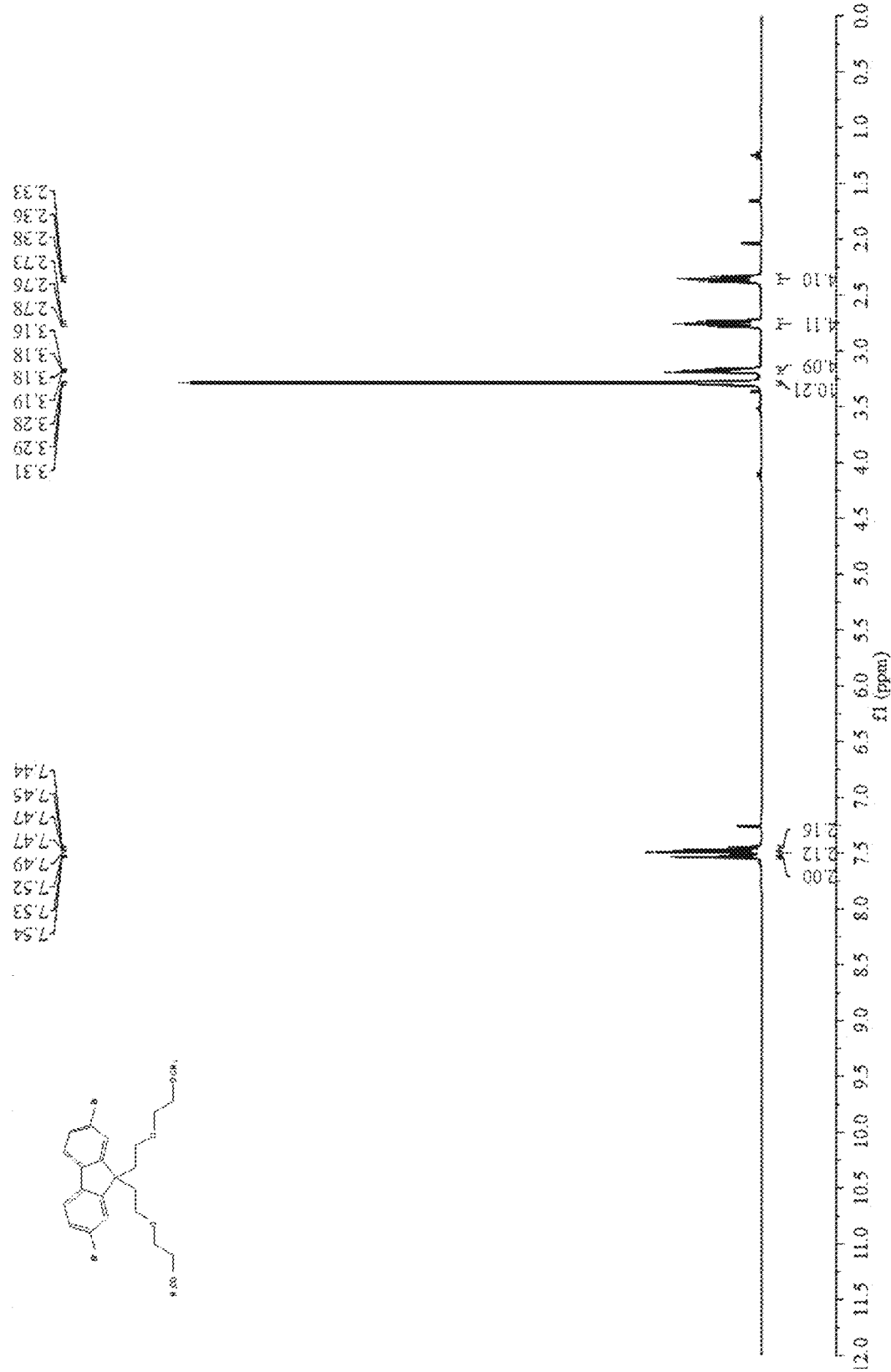
FIG. 7A displays the $^1$H NMR spectra of 2,7-dibromo-9,9-bis(2-(2-methoxyethoxy)ethyl)-9H-fluorene (6).
Figure 7B:
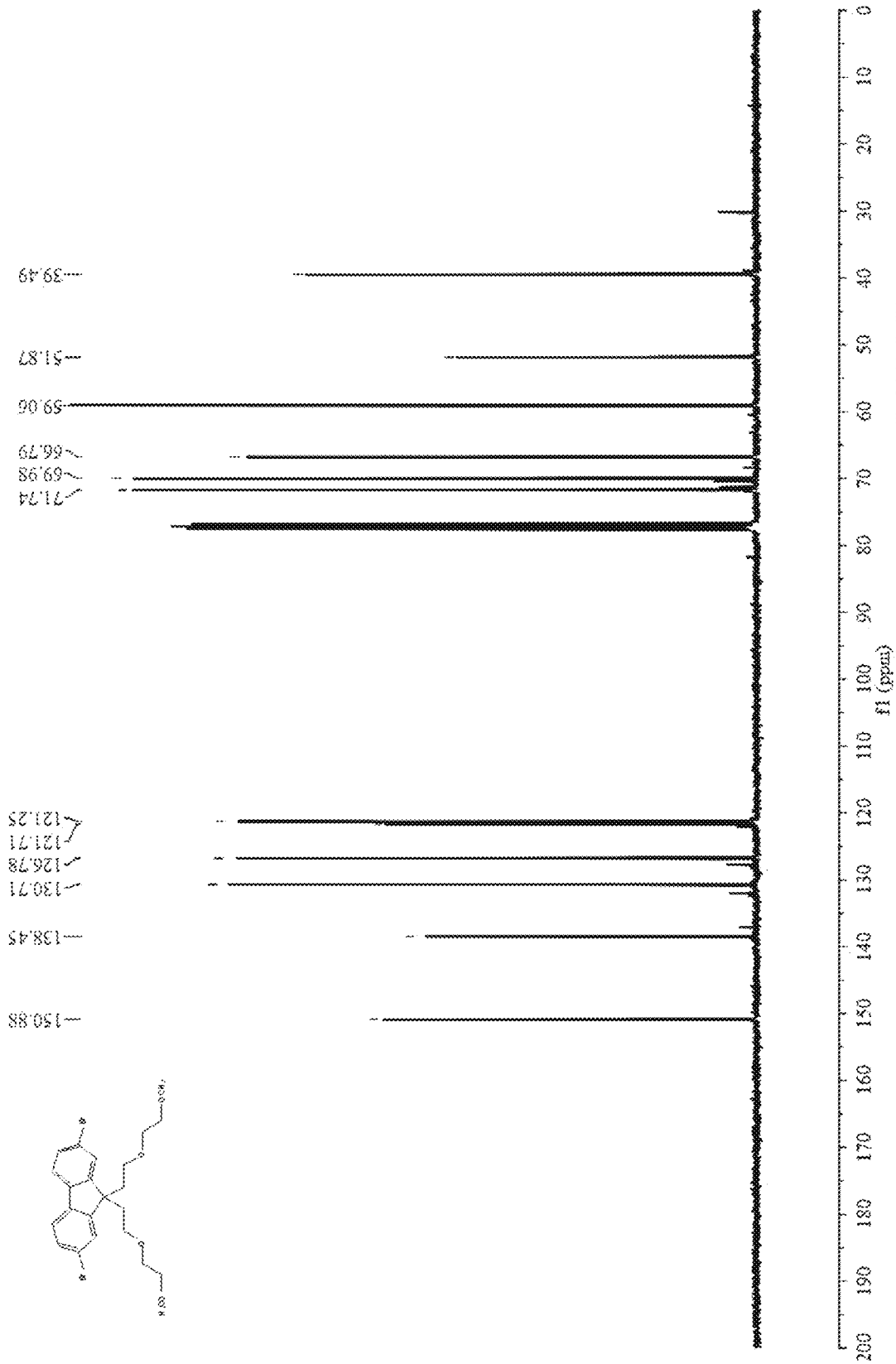
FIG. 7B displays the $^{13}$C NMR spectra of 2,7-dibromo-9,9-bis(2-(2-methoxyethoxy)ethyl)-9H-fluorene (6).

$^1$H, and $^{13}$C NMR spectra of (6) are presented in FIG. 7. $^1$H NMR (300 MHz, CDCl$_3$) δ 7.54 (d, J=1.4 Hz, 2H), 7.51 (d, J=8.0 Hz, 2H), 7.46 (dd, J=8.1, 1.6 Hz, 2H), 3.33-3.26 (m, 10H), 3.18 (dd, J=5.7, 3.4 Hz, 4H), 2.76 (t, J=7.4 Hz, 4H), 2.36 (t, J=7.4 Hz, 4H); $^{13}$C NMR (75 MHz, CDCl$_3$) δ 150.88, 138.45, 130.71, 126.78, 121.71, 121.25, 71.74, 69.98, 66.79, 59.06, 51.87, 39.49.

9,9-Bis(2-(2-methoxyethoxy)ethyl)-2,7-divinyl-9H-fluorene (7)

Compound 6 (1.5 g, 2.8394 mmol, 100 mol %), trimethyl(vinyl)silane (8.5 mL, 58.0066 mmol, 2043 mol %), palladium(II) acetate (223 mg, 0.9933 mmol, 35 mol %), triphenylphosphine (373 mg, 1.4221 mmol, 50 mol %) and anhydrous triethylamine (11.3 mL, 81.0732 mmol, 2855 mol %) were placed in a high-pressure vessel. Anhydrous DMF (15 mL) was added to dissolve the reaction mixture. The high-pressure vessel was sealed, and the reaction mixture was heated to 100° C. for 48 h. The reaction mixture was then cooled to room temperature and the volatile materials were removed under reduced pressure. The residue was suspended in EtOAc (300 mL) and washed with H$_2$O (50 mL×3). The organic phase was collected and concentrated under reduced pressure. The residue was purified on a silica gel column, gradient eluting with 10-20% EtOAc in n-hexane. The solvent was removed under reduced pressure and the silylated intermediate was obtained as a yellow solid (596 mg, 1.0513 mmol, yield=37%). The silylated intermediate was placed in a reaction flask equipped with a water condenser, and the tetrabutylammonium fluoride solution (1 M in THF, 10 mL, 10 mmol, 951 mol %) was added. The reaction mixture was heated under reflux conditions for overnight. The reaction mixture was cooled to r.t., and then distilled water (10 mL) was added. The reaction mixture was stirred for 30 min, and then diluted with EtOAc (100 mL). The organic phase was collected and concentrated under reduced pressure. The residue was purified on a silica gel column, gradient eluting with 5-20% EtOAc in DCM. The solvent was removed under reduced pressure and the product was obtained as a yellow solid 7 (182 mg, 0.4307 mmol, yield=41%).

Figure 8A:
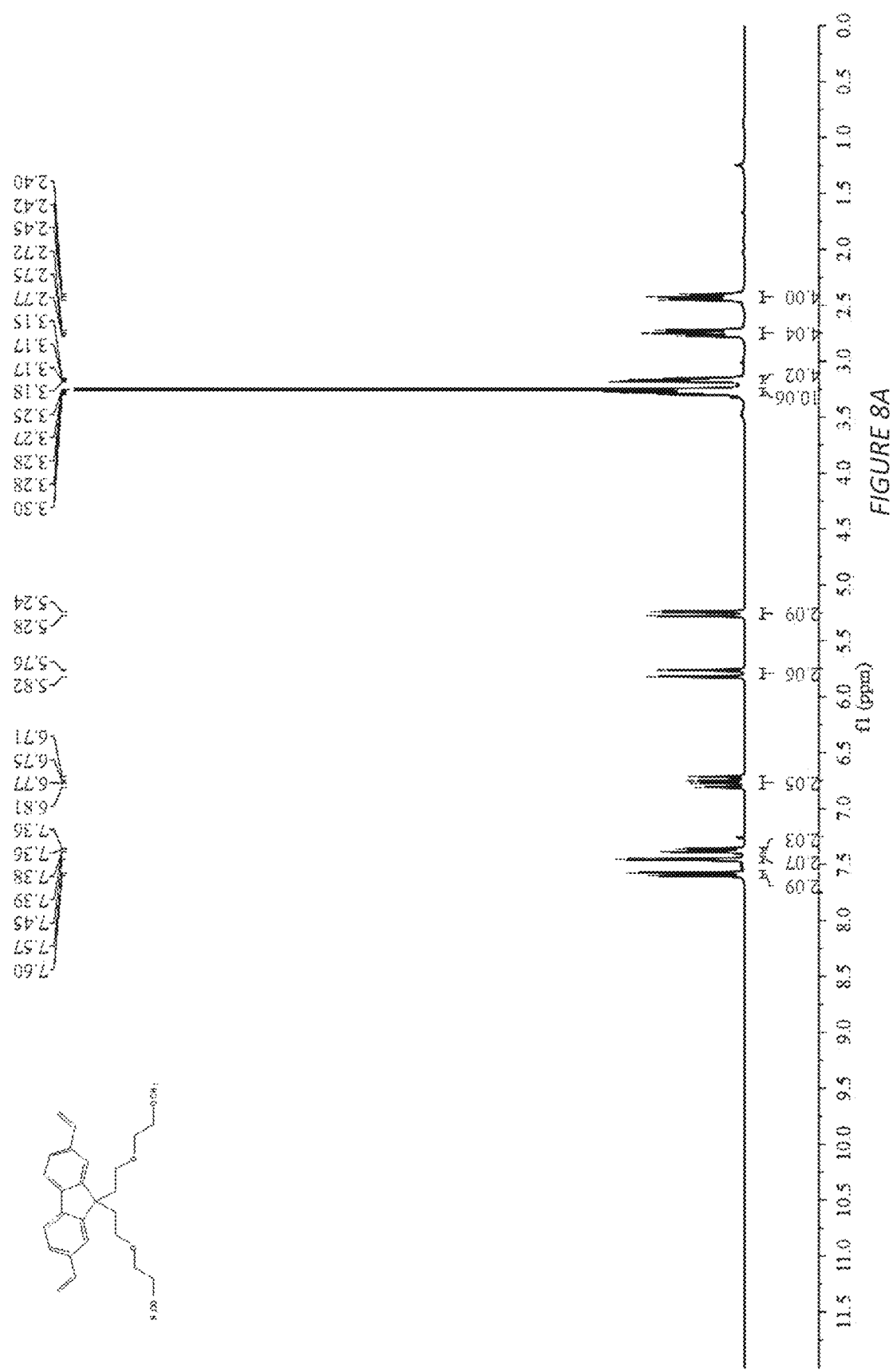
FIG. 8A displays the $^1$H spectra of 9,9-Bis(2-(2-methoxyethoxy)ethyl)-2,7-divinyl-9H-fluorene (7).
Figure 8B:
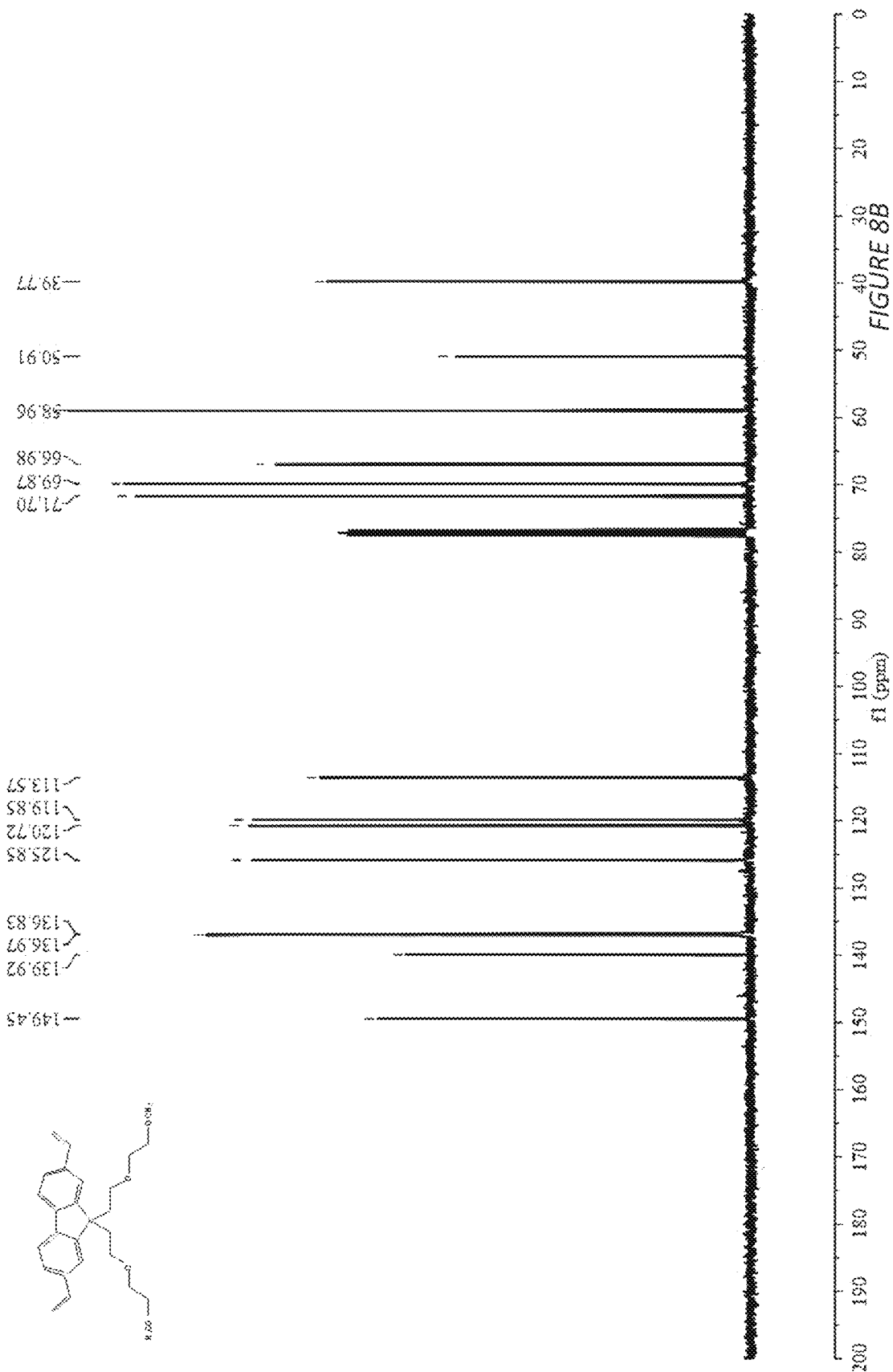
FIG. 8B displays the $^{13}$C spectra of 9,9-Bis(2-(2-methoxyethoxy)ethyl)-2,7-divinyl-9H-fluorene (7).

$^1$H, and $^{13}$C NMR spectra of (7) are presented in FIG. 8. $^1$H NMR (300 MHz, CDCl$_3$) δ 7.59 (d, J=7.8 Hz, 2H), 7.45 (s, 2H), 7.37 (dd, J=7.9, 1.2 Hz, 2H), 6.76 (dd, J=17.6, 10.9 Hz, 2H), 5.79 (d, J=17.5 Hz, 2H), 5.26 (d, J=10.9 Hz, 2H), 3.31-3.24 (m, 10H), 3.17 (dd, J=5.7, 3.3 Hz, 4H), 2.84-2.68 (m, 4H), 2.50-2.36 (m, 4H); $^{13}$C NMR (75 MHz, CDCl$_3$) δ 149.45, 139.92, 136.97, 136.83, 125.85, 120.72, 119.85, 113.57, 71.70, 69.87, 66.98, 58.96, 50.91, 39.77

(E)-2-(3-(1-(Bis(4-methoxyphenyl)(phenyl)methoxy)propan-2-yl)-4-nitrostyryl)-9,9-bis(2-(2-methoxyethoxy)ethyl)-7-vinyl-9H-fluorene (8)

Compound 7 (310 mg, 0.73 mmol, 103 mol %), compound 3 (400 mg, 0.71 mmol, 100 mol %), palladium(II) acetate (20 mg, 0.089 mmol, 12.5 mol %), potassium carbonate (200 mg, 1.45 mmol, 204 mol %) and tetrabutylammonium bromide (230 mg, 0.71 mmol, 100 mol %) were placed in a high-pressure vessel. Anhydrous DMF (12 mL) was added to dissolve the reaction mixture. The high-pressure vessel was sealed, and the reaction mixture was heated to 110° C. for 12 h. After that, the reaction mixture was cooled to room temperature and diluted with EtOAc (100 mL). The insoluble materials were removed by filtration and the filtrate was washed with H$_2$O (10 mL×3). The organic phase was collected and concentrated under reduced pressure. The residue was purified on a silica gel column, gradient eluting with 1-5% EtOAc in DCM. The solvent was removed under reduced pressure and the product was obtained as a yellow solid 8 (159 mg, 0.1759 mmol, yield=24%).

Figure 9A:
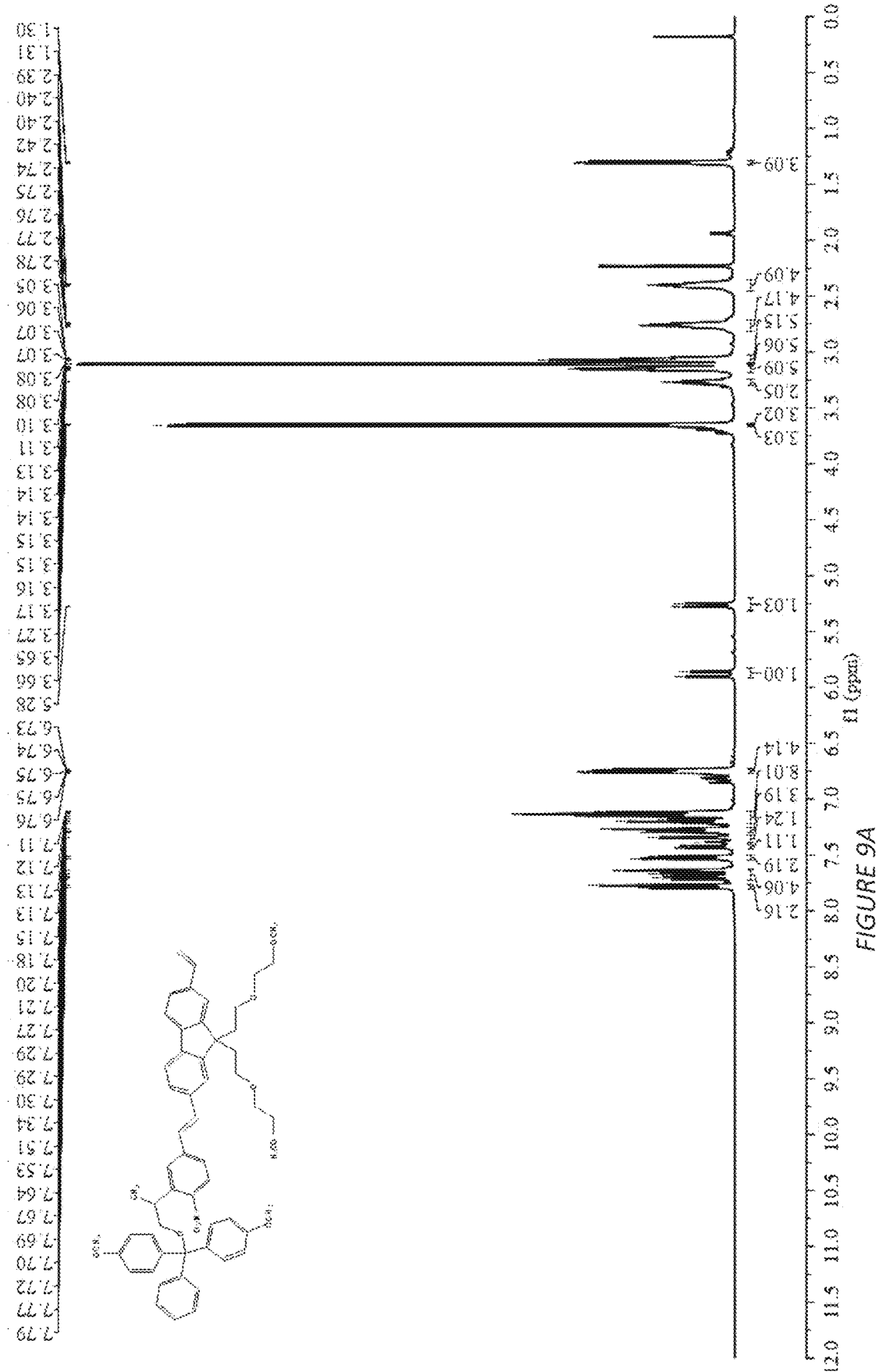
FIG. 9A displays the ¹H NMR spectra (E)-2-(3-(1-(Bis(4-methoxyphenyl)(phenyl)methoxy)propan-2-yl)-4-nitrostyryl)-9,9-bis(2-(2-methoxyethoxy)ethyl)-7-vinyl-9H-fluorene (8).
Figure 9B:
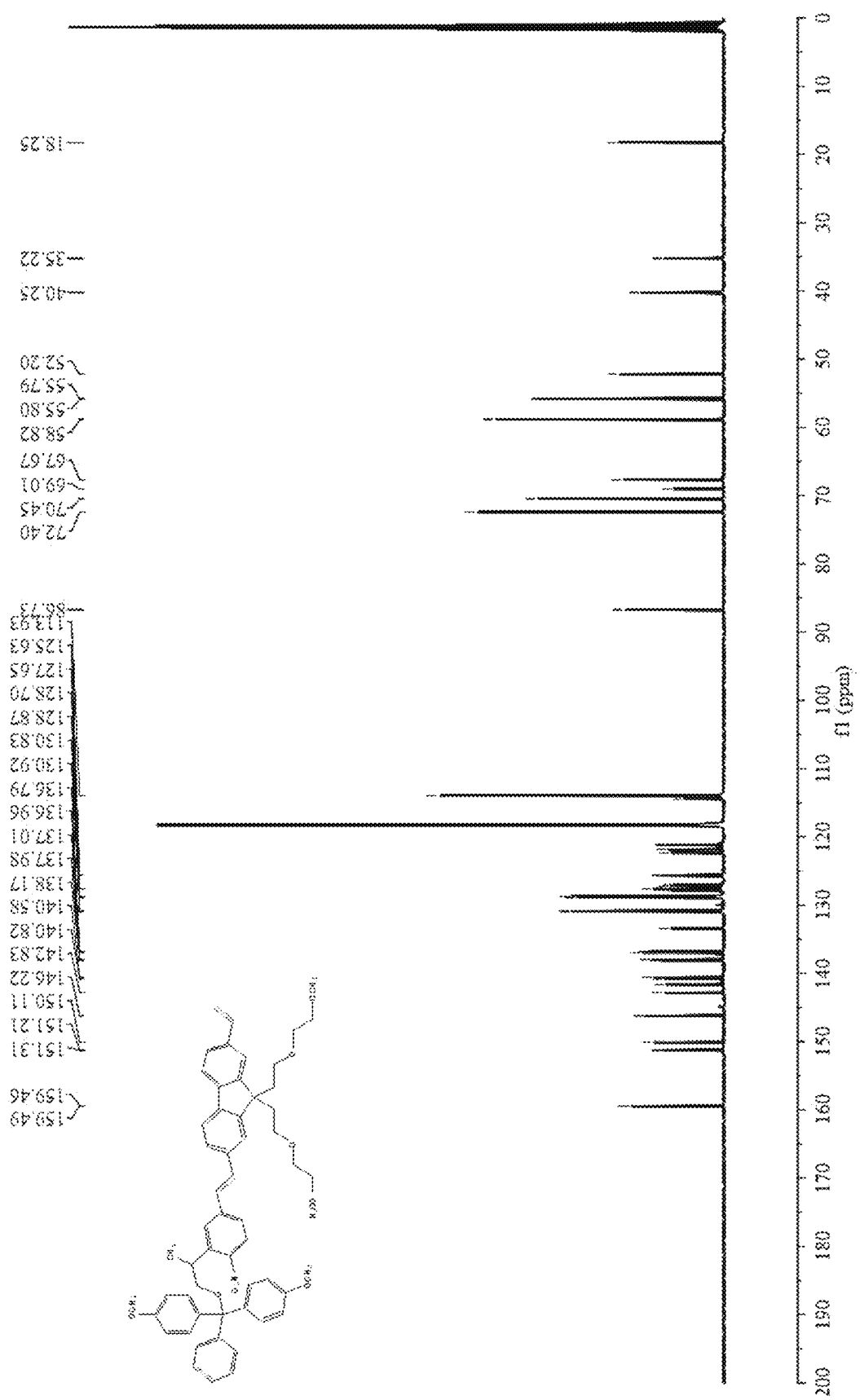
FIG. 9B displays the ¹³C NMR spectra (E)-2-(3-(1-(Bis(4-methoxyphenyl)(phenyl)methoxy)propan-2-yl)-4-nitrostyryl)-9,9-bis(2-(2-methoxyethoxy)ethyl)-7-vinyl-9H-fluorene (8).

$^1$H, and $^{13}$C NMR spectra of (8) are presented in FIG. 9. $^1$H NMR (400 MHz, CD$_3$CN) δ 7.78 (d, J=8.6 Hz, 2H), 7.73-7.62 (m, 4H), 7.52 (d, J=8.5 Hz, 2H), 7.43 (dd, J=7.9, 1.0 Hz, 1H), 7.36 (d, J=16.4 Hz, 1H), 7.31-7.25 (m, 3H), 7.22-7.11 (m, 8H), 6.77-6.72 (m, 4H), 5.88 (d, J=17.6 Hz, 1H), 5.27 (d, J=11.2 Hz, 1H), 3.66 (s, 3H), 3.65 (s, 3H), 3.27 (dd, J=10.0, 5.2 Hz, 2H), 3.17-3.13 (m, 5H), 3.11 (d, J=1.9 Hz, 5H), 3.09-3.05 (m, 5H), 2.76 (td, J=7.7, 3.2 Hz, 4H), 2.40 (dd, J=6.9, 4.8 Hz, 4H), 1.31 (d, J=7.0 Hz, 3H); $^{13}$C NMR (101 MHz, CD$_3$CN) δ 159.49, 159.46, 151.31, 151.21, 150.11, 146.22, 142.83, 141.64, 140.82, 140.58, 138.17, 137.98, 137.01, 136.96, 136.79, 133.43, 130.92, 130.83, 128.87, 128.70, 127.90, 127.65, 127.55, 127.20, 126.98, 125.74, 125.63, 122.36, 121.84, 121.21, 121.14, 114.44, 113.93, 86.73, 72.40, 70.45, 69.01, 67.67, 58.82, 55.80, 55.79, 52.20, 40.25, 35.22, 18.25.

2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propan-1-ol (9)

Compound 8 (100 mg, 0.1106 mmol, 100 mol %), compound 2 (100 mg, 0.3845 mmol, 348 mol %), palladium(II) acetate (8 mg, 0.0356 mmol, 32 mol %), potassium carbonate (34 mg, 0.2460 mmol, 222 mol %) and tetrabutylammonium bromide (36 mg, 0.1117 mmol, 101 mol %) were placed in a high-pressure vessel. Anhydrous DMF (8 mL) was added to dissolve the reaction mixture. The high-pressure vessel was sealed, and the reaction mixture was heated to 110° C. for 12 h. After that, the reaction mixture was cooled to room temperature and diluted with EtOAc (100 mL). The insoluble materials were removed by filtration and the filtrate was washed with H$_2$O (10 mL×3). The organic phase was collected and concentrated under reduced pressure. The residue was purified on a silica gel column, gradient eluting with 5-50% EtOAc in DCM. The solvent was removed under reduced pressure and the product was obtained as a yellow solid 9 (70 mg, 0.0646 mmol, yield=58%).

Figure 10A:
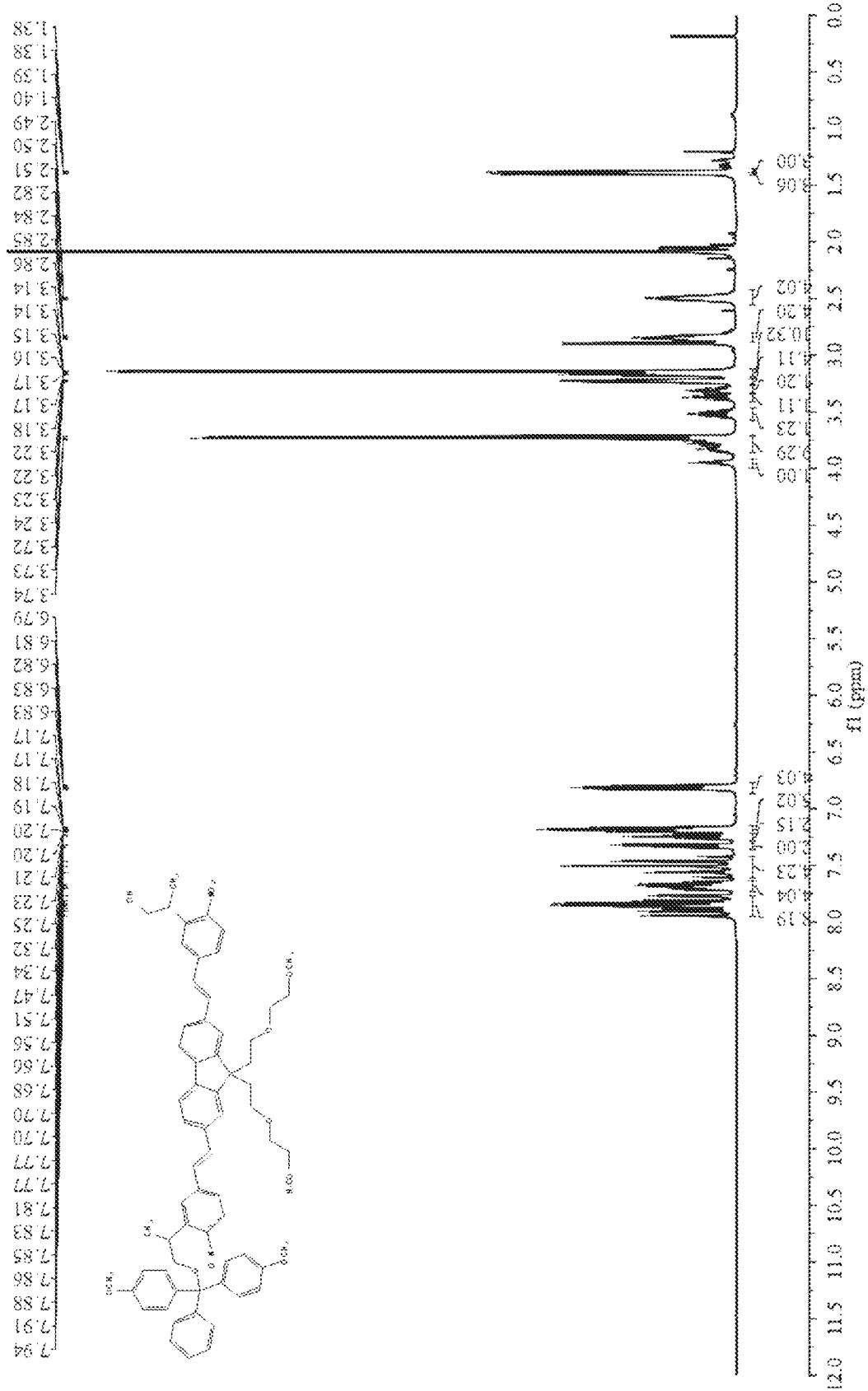
FIG. 10A displays the ¹H NMR spectra of 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propan-1-ol (9).
Figure 10B:
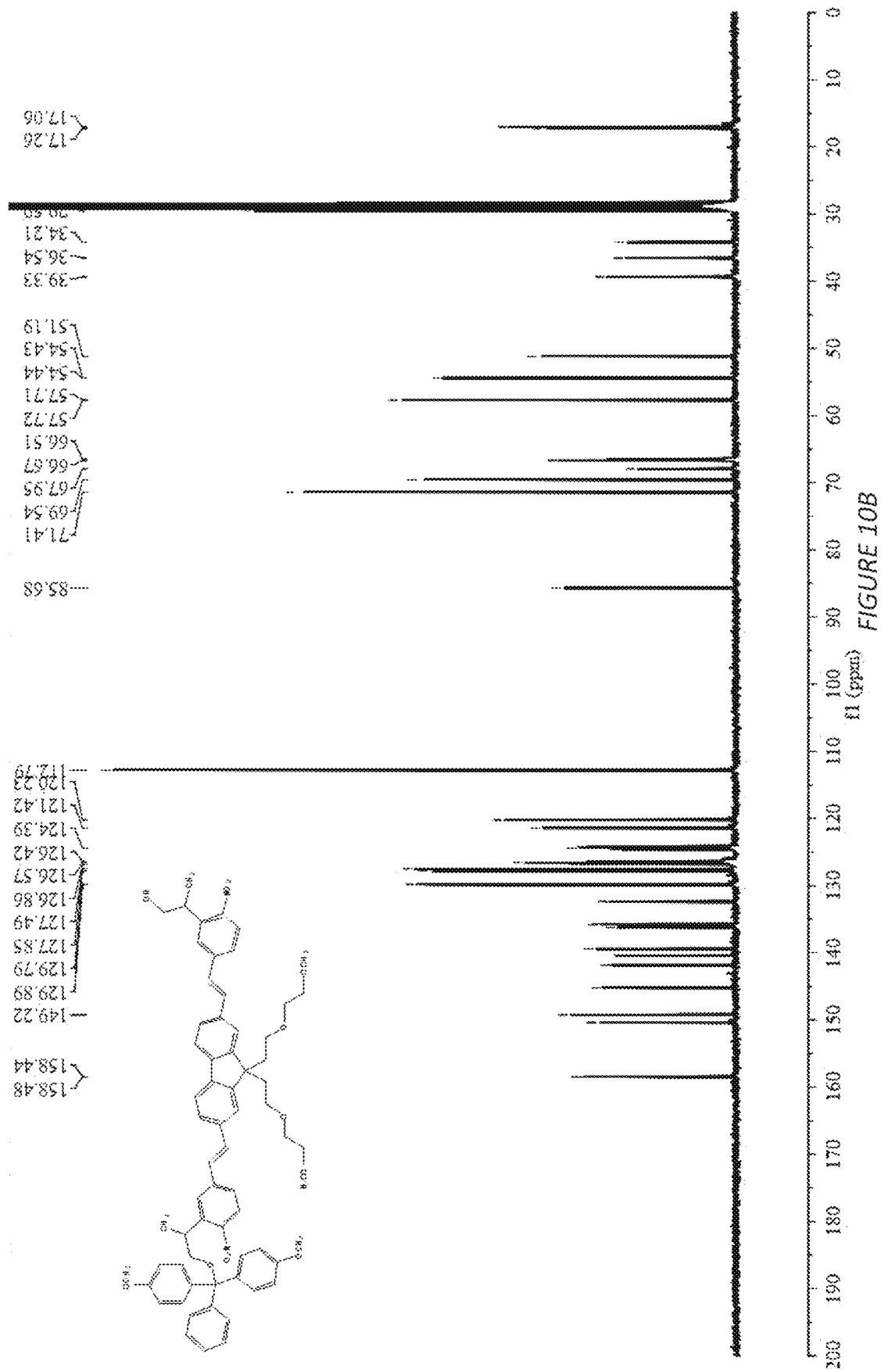
FIG. 10B displays the ¹³C NMR spectra of 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propan-1-ol (9).

$^1$H, and $^{13}$C NMR spectra of (9) are presented in FIG. 10. $^1$H NMR (400 MHz, Acetone) δ 7.95-7.76 (m, 8H), 7.73-7.64 (m, 4H), 7.52 (dq, J=33.1, 16.4 Hz, 4H), 7.33 (d, J=7.3 Hz, 2H), 7.25 (t, J=7.5 Hz, 2H), 7.21-7.15 (m, 5H), 6.87-6.77 (m, 4H), 3.95 (t, J=5.4 Hz, 1H), 3.87-3.69 (m, 9H), 3.56-3.47 (m, 1H), 3.37 (t, J=8.2 Hz, 1H), 3.30 (dd, J=8.8, 5.3 Hz, 1H), 3.26-3.20 (m, 4H), 3.19-3.12 (m, 10H), 2.85 (dt, J=12.0, 6.1 Hz, 4H), 2.50 (td, J=7.3, 3.5 Hz, 4H), 1.40 (d, J=2.9 Hz, 3H), 1.38 (d, J=3.0 Hz, 3H); $^{13}$C NMR (101 MHz, Acetone) δ 158.48, 158.44, 150.39, 150.38, 149.22, 145.19, 141.85, 141.79, 140.46, 140.41, 139.43, 139.40, 136.28, 136.22, 135.83, 135.68, 132.44, 132.36, 129.89, 129.79, 127.85, 127.49, 126.86, 126.57, 126.42, 126.38, 126.29, 124.62, 124.44, 124.39, 124.23, 124.17, 121.42, 120.23, 112.79, 85.68, 71.41, 69.54, 67.95, 66.67, 66.51, 57.72, 57.71, 54.44, 54.43, 51.19, 39.33, 36.54, 34.21, 29.59, 17.26, 17.06.

2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propyl (2-cyanoethyl) diisopropylphosphoramidite (10)

Compound 9 (600 mg, 0.5539 mmol, 100 mol %) and 5-ethylthio-1H-tetrazole (120 mg, 0.9219 mmol, 166 mol %) were placed in a round bottom flask and dissolved in a mixture of anhydrous ACN (4 mL) and anhydrous THF (1 mL). Compound 4 (0.45 mL, 1.4170 mmol, 256 mol %) was then added to the reaction mixture and stirred at room temperature for overnight. After that, the crude mixture was directly loaded on a silica gel column and the product was gradient eluting with 10-50% EtOAc in DCM containing 1% Et$_3$N. The solvent was removed under reduced pressure and the product was obtained as an orange solid 10 (284 mg, 0.2213 mmol, yield=40%). The dried product was stored at −20° C. and under N$_2$ atmosphere.

Figure 11A:
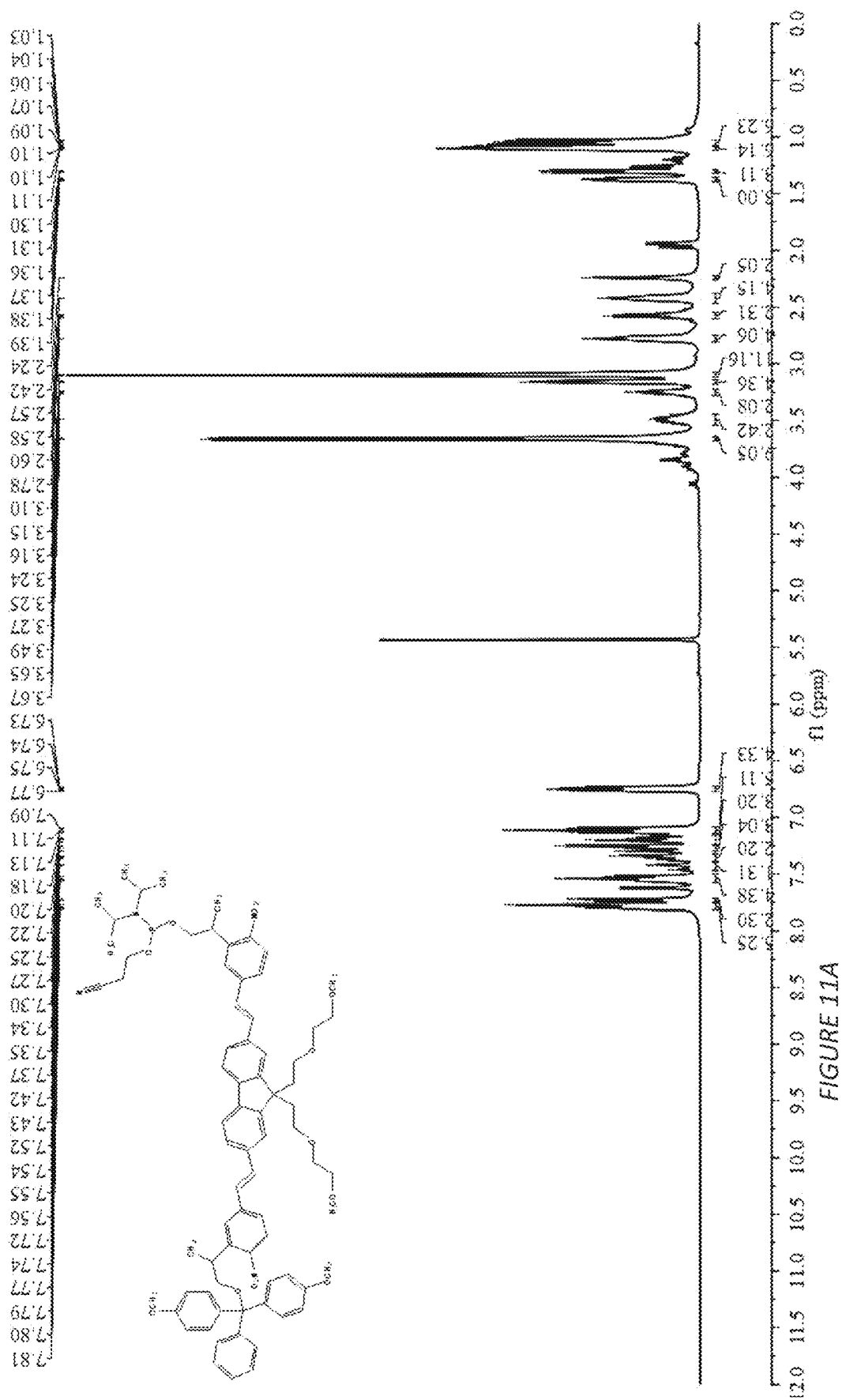
FIG. 11A displays the ¹H NMR spectra of 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propyl (2-cyanoethyl) diisopropylphosphoramidite (10).
Figure 11B:
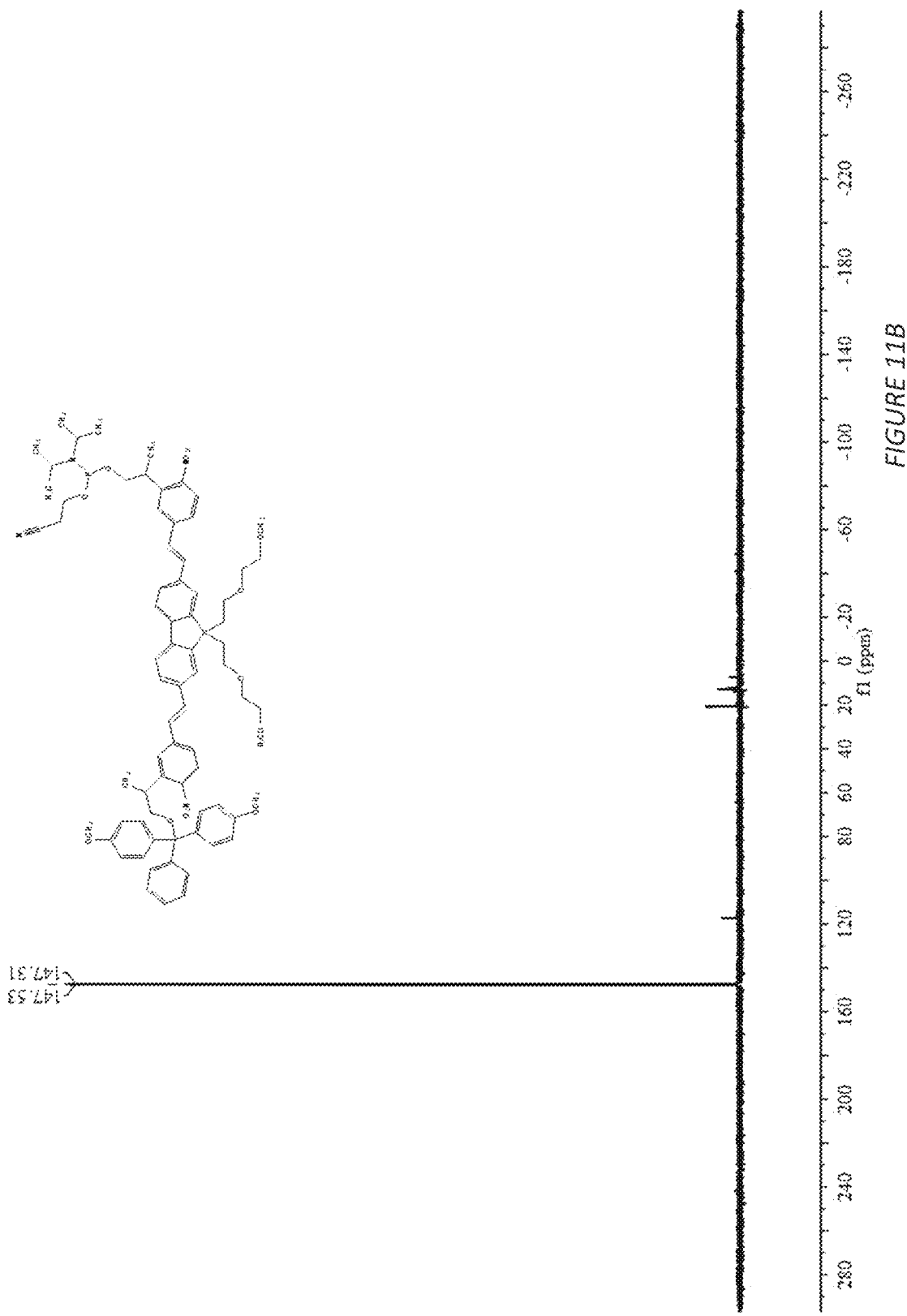
FIG. 11B displays the ³¹P NMR spectra of 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propyl (2-cyanoethyl) diisopropylphosphoramidite (10).
Figure 11C:
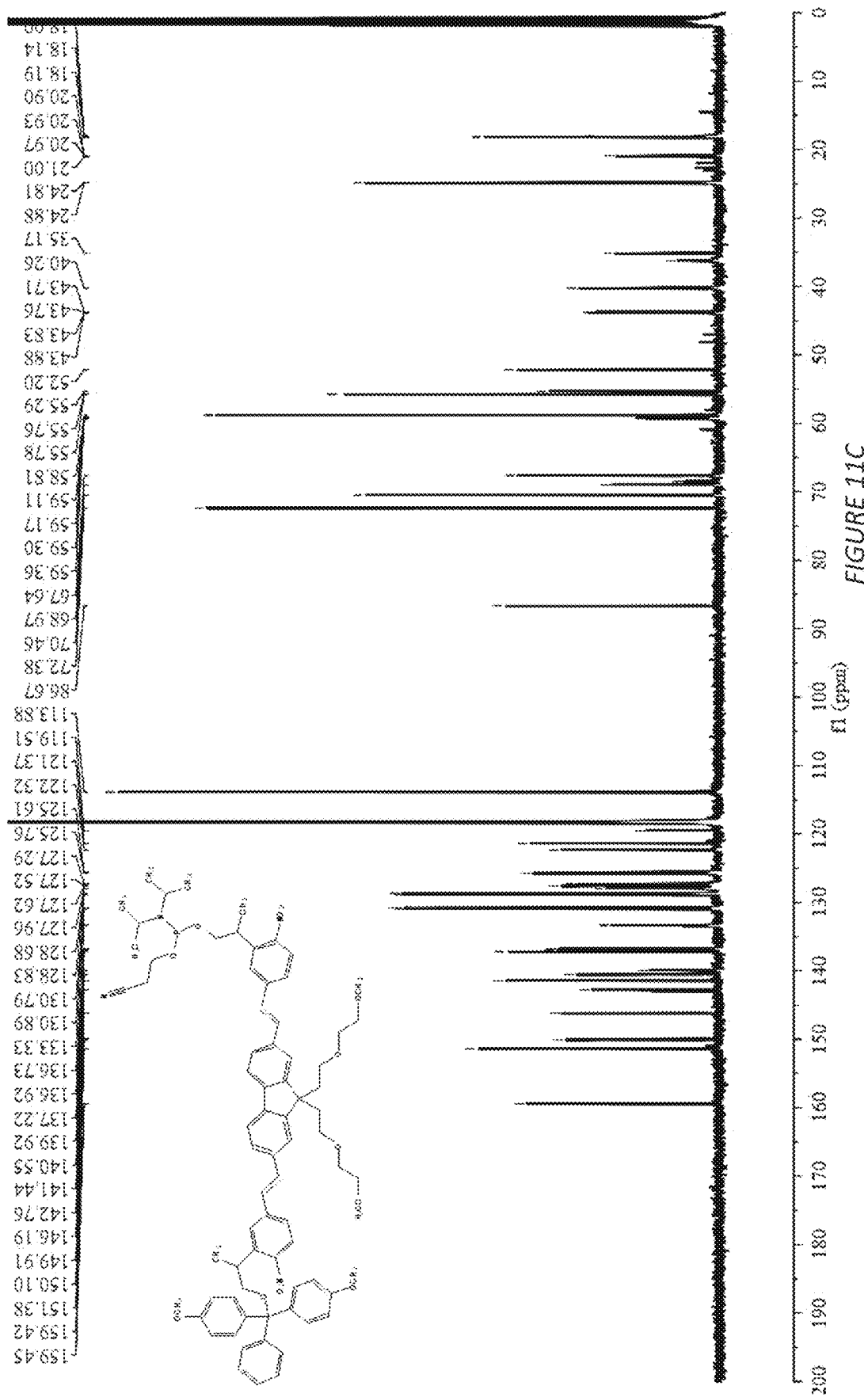
FIG. 11C displays the ¹³C NMR spectra of 2-(5-((E)-2-(7-((E)-3-(1-(bis(4-methoxyphenyl)(phenyl)methoxy)propan-2-yl)-4-nitrostyryl)-9,9-bis(2-(2-methoxyethoxy)ethyl)-9H-fluoren-2-yl)vinyl)-2-nitrophenyl)propyl (2-cyanoethyl) diisopropylphosphoramidite (10).

$^1$H, $^{31}$P and $^{13}$C NMR spectra of (10) are presented in FIG. 11. $^1$H NMR (400 MHz, CD$_3$CN) δ 7.79 (dd, J=8.8, 6.4 Hz, 5H), 7.73 (d, J=7.9 Hz, 2H), 7.54 (dd, J=11.0, 5.3 Hz, 4H), 7.44 (dd, J=16.3, 2.7 Hz, 1H), 7.39-7.33 (m, 2H), 7.31-7.25 (m, 3H), 7.20 (t, J=7.4 Hz, 3H), 7.11 (t, J=8.0 Hz, 5H), 6.75 (dd, J=8.6, 5.3 Hz, 4H), 3.66 (d, J=6.3 Hz, 9H), 3.54-3.44 (m, 2H), 3.30-3.22 (m, 2H), 3.16 (d, J=4.0 Hz, 4H), 3.10 (s, 11H), 2.78 (s, 4H), 2.62-2.54 (m, 2H), 2.42 (s, 4H), 2.24 (s, 2H), 1.38 (dd, J=6.7, 3.2 Hz, 3H), 1.31 (d, J=6.9 Hz, 3H), 1.10 (dd, J=6.6, 4.1 Hz, 6H), 1.05 (dd, J=12.1, 6.8 Hz, 6H); $^{31}$P NMR (162 MHz, CD$_3$CN) δ 147.53, 147.31; $^{13}$C NMR (101 MHz, CD$_3$CN) δ 159.45, 159.42, 151.38, 150.10, 150.02, 149.91, 146.19, 142.96, 142.94, 142.76, 141.44, 140.55, 140.03, 139.92, 137.22, 136.92, 136.73, 133.47, 133.44, 133.33, 130.89, 130.79, 128.83, 128.68, 127.96, 127.81, 127.62, 127.52, 127.29, 125.76, 125.61, 122.32, 121.37, 119.51, 113.88, 86.67, 72.38, 70.46, 68.97, 68.84, 68.54, 68.38, 67.64, 59.36, 59.30, 59.17, 59.11, 58.81, 55.78, 55.76, 55.29, 52.20, 43.88, 43.83, 43.76, 43.71, 40.26, 36.22, 35.17, 24.88, 24.81, 21.00, 20.97, 20.93, 20.90, 18.19, 18.14, 18.00.

4,4'-Dibromo-3,3'-dimethoxy-1,1'-biphenyl (11)

o-Dianisidine (2.86 g, 11.7 mmol, 100 mol %) was placed in a reaction flask equipped with a water condenser and dissolved in ACN (46 mL). Distilled water (46 mL) and 48% aqueous hydrobromic acid (12 mL) were successively added to the reaction mixture. The reaction mixture was then cooled to 0° C. and stirred for 20 min. Sodium nitrite (2.06 g, 29.9 mmol, 256 mol %) was dissolved in a separated flask by distilled water (4 mL). The solution was cooled to 0° C. The cool sodium nitrite solution was then added to the reaction mixture. Following the addition, the reaction mixture was stirred in the ice water bath for 45 min. Copper(I) bromide (3.71 g, 25.9 mmol, 221 mol %) was dissolved in a separated flask by 48% aqueous hydrobromic acid (46 mL). The solution was cooled to 0° C. The cool copper(I) bromide solution was then added to the reaction mixture. Following the addition, the reaction mixture was stirred in the ice water bath for 10 min. The reaction mixture was then warmed to room temperature and subsequently heated under reflux conditions for 2.5 h. After that, the solution was cooled to room temperature and extracted with chloroform (100 mL). The organic layer was collected, washed with 10% aqueous sodium hydroxide solution (50 mL) and brine (50 mL). The organic phase was collected and concentrated under reduced pressure. The residue was purified on a silica gel column, isocratic eluting with chloroform. The solvent was removed under reduced pressure and the product was obtained as a brown solid 11 (3.65 g, 9.81 mmol, yield=84%).

Figure 12A:
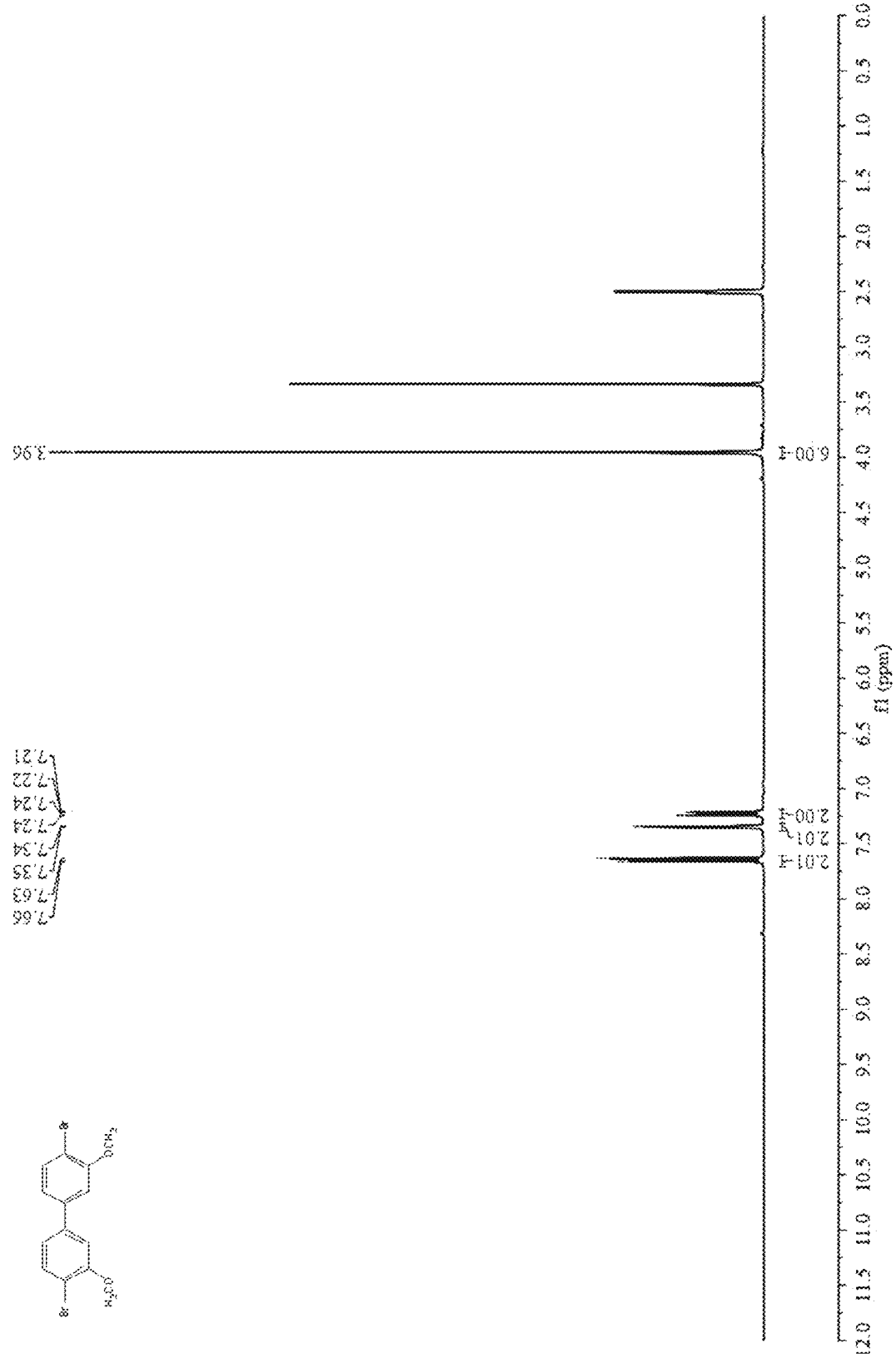
FIG. 12A displays the 1H NMR spectra of 4,4'-Dibromo-3,3'-dimethoxy-1,1'-biphenyl (11).
Figure 12B:
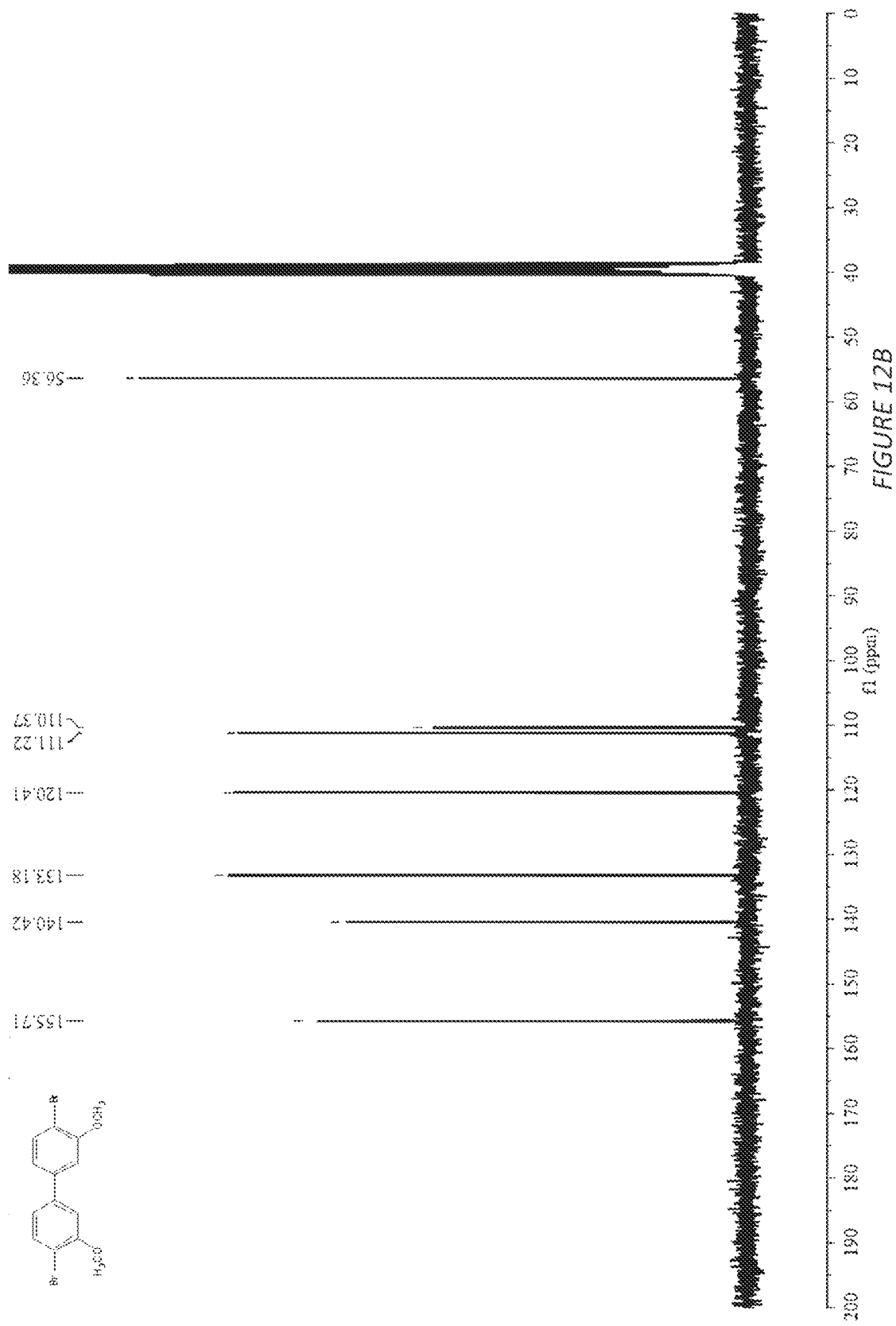
FIG. 12B displays the ¹³C NMR spectra of 4,4'-Dibromo-3,3'-dimethoxy-1,1'-biphenyl (11).

$^1$H, and $^{13}$C NMR spectra of (11) are presented in FIG. 12. $^1$H NMR (300 MHz, DMSO) δ 7.65 (d, J=8.2 Hz, 2H), 7.35 (d, J=2.0 Hz, 2H), 7.23 (dd, J=8.2, 2.0 Hz, 2H), 3.96 (s, 6H);

$^{13}$C NMR (75 MHz, DMSO) δ 155.71, 140.42, 133.18, 120.41, 111.22, 110.37, 56.36.

3,3'-Dimethoxy-4,4'-divinyl-1,1'-biphenyl (12)

Compound 11 (1.5 g, 4.0316 mmol, 100 mol %), trimethyl(vinyl)silane (12 mL, 82 mmol, 2043 mol %), palladium(II) acetate (320 mg, 1.4253 mmol, 35 mol %), triphenylphosphine (530 mg, 2.0207 mmol, 50 mol %) and anhydrous triethylamine (16 mL, 11.616 mmol, 2852 mol %) were placed in a high-pressure vessel. Anhydrous DMF (15 mL) was added to dissolve the reaction mixture. The high-pressure vessel was sealed, and the reaction mixture was heated to 100° C. for 48 h. The reaction mixture was then cooled to r.t. and the volatile materials were removed under reduced pressure. The residue was suspended in EtOAc (300 mL) and washed with $H_2O$ (50 mL×3). The organic phase was collected and concentrated under reduced pressure. The residue was purified on a silica gel column, gradient eluting with 20-30% DCM in n-hexane. The solvent was removed under reduced pressure and the silylated intermediate was obtained as a yellow solid (844 mg, 2.0550 mmol, yield=51%). The silylated intermediate was placed in a two-necked flask, and the tetrabutylammonium fluoride solution (1 M in THF, 20 mL, 20 mmol, 973 mol %) was added. The reaction mixture was heated under reflux conditions for overnight. The reaction mixture was cooled to room temperature and then saturated aq. $NH_4Cl$ solution (20 mL) was added. The reaction mixture was stirred for 30 min, and then diluted with EtOAc (250 mL). The organic phase was collected, washed with aqueous HCl solution (1 M, 50 mL x 2) and distilled water (50 mL). The organic phase was collected and concentrated under reduced pressure. The residue was purified on a silica gel column, gradient eluting with 10-40% DCM in n-hexane containing 1% $Et_3N$. The solvent was removed under reduced pressure and the product was obtained as a white solid 12 (235 mg, 0.8823 mmol, yield=43%).

Figure 13A:
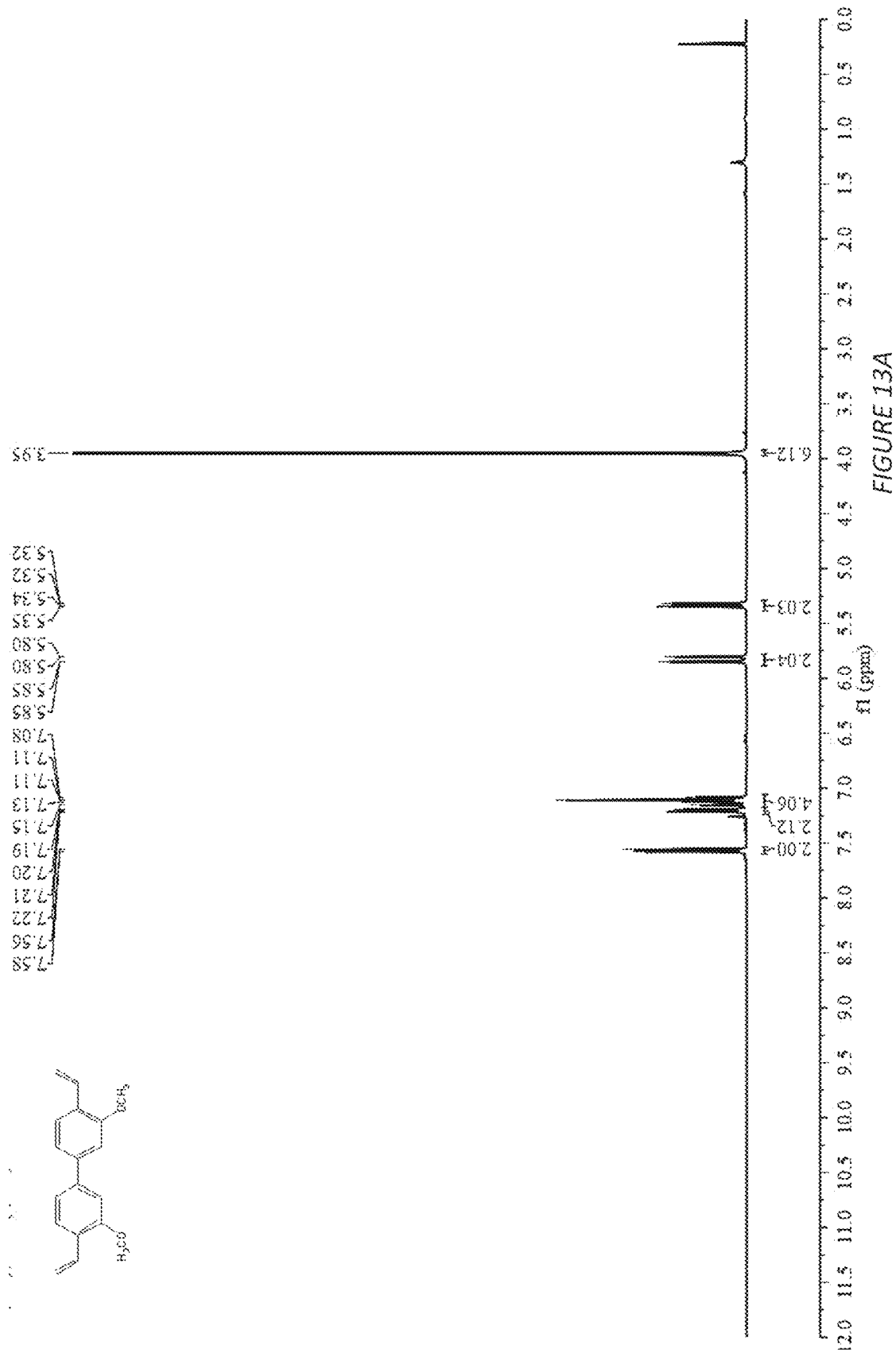
FIG. 13A displays the ¹H NMR spectra of 3,3'-Dimethoxy-4,4'-divinyl-1,1'-biphenyl (12).
Figure 13B:
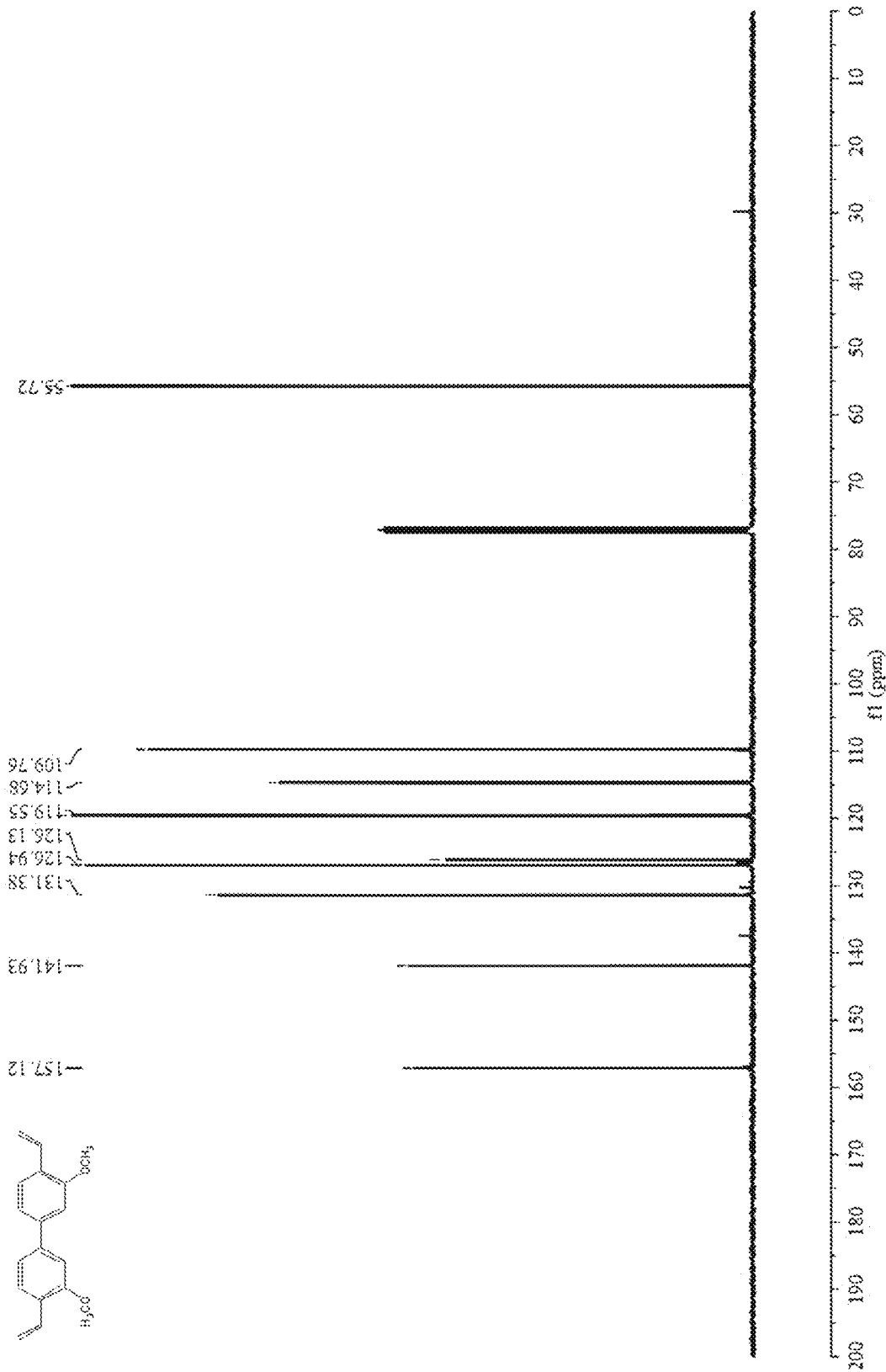
FIG. 13B displays the ¹³C NMR spectra of 3,3'-Dimethoxy-4,4'-divinyl-1,1'-biphenyl (12).

$^1$H, and $^{13}$C NMR spectra of (12) are presented in FIG. 13. $^1$H NMR (400 MHz, CDCl$_3$) δ 7.57 (d, J=7.9 Hz, 2H), 7.20 (dd, J=7.9, 1.4 Hz, 2H), 7.17-7.07 (m, 4H), 5.83 (dd, J=17.8, 1.4 Hz, 2H), 5.33 (dd, J=11.2, 1.4 Hz, 2H), 3.95 (s, 6H); $^{13}$C NMR (101 MHz, CDCl$_3$) δ 157.12, 141.93, 131.38, 126.94, 126.13, 119.55, 114.68, 109.76, 55.72.

(E)-4-(3-(1-(bis(4-methoxyphenyl)(phenyl)methoxy) propan-2-yl)-4-nitrostyryl)-3,3'-dimethoxy-4'-vinyl-1,1'-biphenyl (13)

Compound 12 (162 mg, 0.608 mmol, 100 mol %), compound 3 (350 mg, 0.622 mmol, 102 mol %), palladium(II) acetate (17 mg, 0.0757 mmol, 12.5 mol %), potassium carbonate (170 mg, 1.23 mmol, 202 mol %) and tetrabutylammonium bromide (200 mg, 0.62 mmol, 102 mol %) were placed in a high-pressure vessel. Anhydrous DMF (10 mL) was added to dissolve the reaction mixture. The high-pressure vessel was sealed, and the reaction mixture was heated to 110° C. for 12 h. After that, the reaction mixture was cooled to room temperature and diluted with EtOAc (100 mL). The insoluble materials were removed by filtration and the filtrate was washed with $H_2O$ (10 mL×3). The organic phase was collected and concentrated under reduced pressure. The residue was purified on a silica gel column, gradient eluting with 20-50% DCM in n-hexane containing 1% $Et_3N$. The solvent was removed under reduced pressure and the product was obtained as a yellow solid 13 (140 mg, 0.1872 mmol, yield=31%).

Figure 14A:
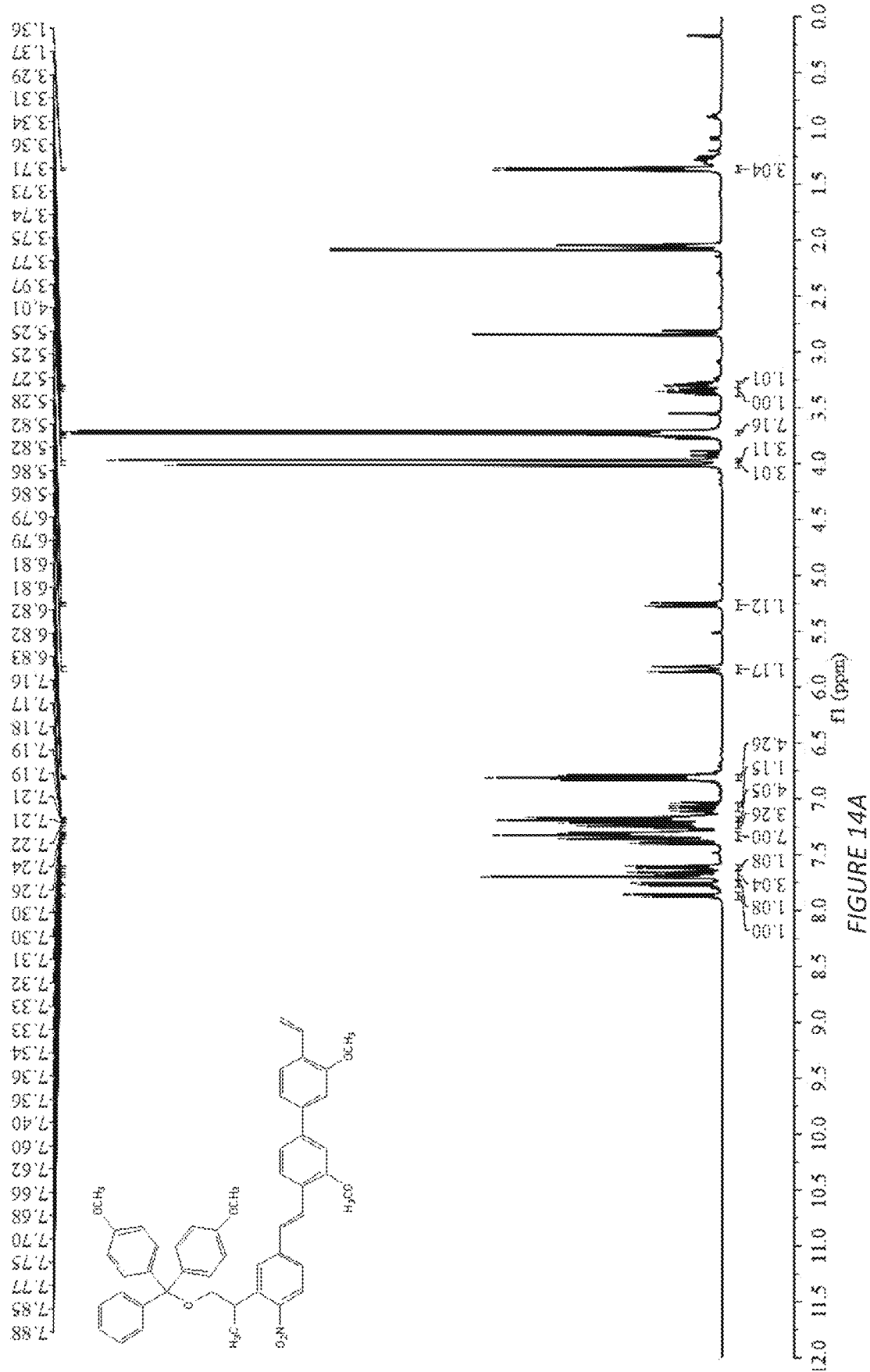
FIG. 14A displays the ¹³C NMR spectra of (E)-4-(3-(1-(Bis(4-methoxyphenyl)(phenyl)methoxy)propan-2-yl)-4-nitrostyryl)-3,3'-dimethoxy-4'-vinyl-1,1'-biphenyl (13).
Figure 14B:
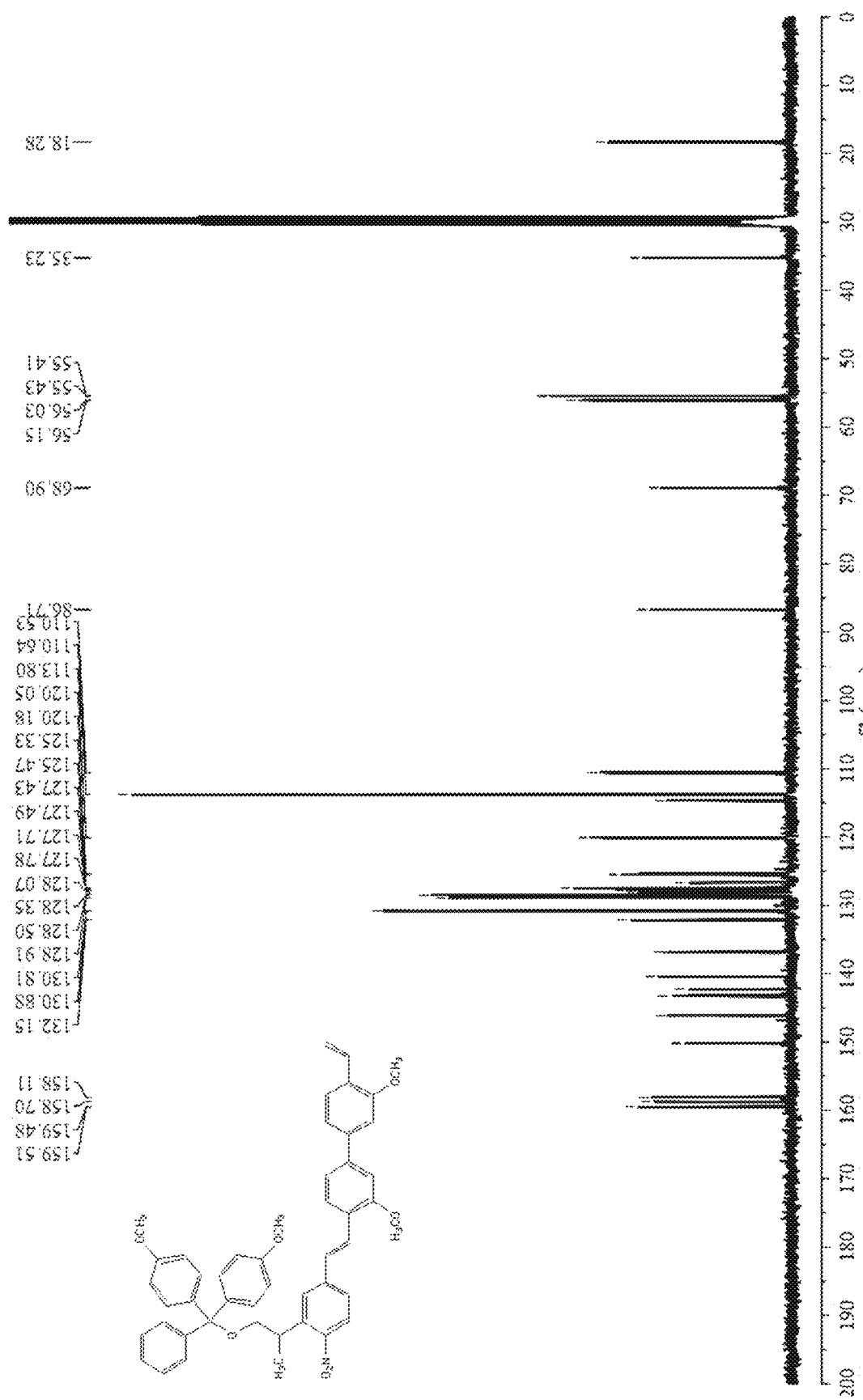
FIG. 14B displays the ¹H NMR spectra of (E)-4-(3-(1-(Bis(4-methoxyphenyl)(phenyl)methoxy)propan-2-yl)-4-nitrostyryl)-3,3'-dimethoxy-4'-vinyl-1,1'-biphenyl (13).

$^1$H, and $^{13}$C NMR spectra of (13) are presented in FIG. 14. $^1$H NMR (400 MHz, Acetone) δ 7.87 (d, J=9.0 Hz, 1H), 7.76 (d, J=7.9 Hz, 1H), 7.71-7.65 (m, 3H), 7.61 (d, J=7.9 Hz, 1H), 7.38-7.28 (m, 7H), 7.27-7.21 (m, 3H), 7.20-7.15 (m, 4H), 7.07 (dd, J=17.9, 11.3 Hz, 1H), 6.84-6.78 (m, 4H), 5.84 (dd, J=17.8, 1.5 Hz, 1H), 5.26 (dd, J=11.2, 1.5 Hz, 1H), 4.01 (s, 3H), 3.97 (s, 3H), 3.77-3.70 (m, 7H), 3.36 (t, J=8.2 Hz, 1H), 3.29 (dd, J=8.8, 5.3 Hz, 1H), 1.37 (d, J=7.0 Hz, 3H); $^{13}$C NMR (101 MHz, Acetone) δ 159.51, 159.48, 158.70, 158.11, 150.17, 146.13, 143.28, 143.11, 142.27, 140.41, 136.90, 136.80, 132.15, 130.88, 130.81, 128.91, 128.50, 128.35, 128.07, 127.78, 127.71, 127.49, 127.43, 126.70, 125.59, 125.47, 125.33, 120.18, 120.05, 114.65, 113.80, 110.64, 110.53, 86.71, 68.90, 56.15, 56.03, 55.43, 55.41, 35.23, 18.28.

2-(5-((E)-2-(4'-((E)-3-(1-(bis(4-methoxyphenyl) (phenyl)methoxy)propan-2-yl)-4-nitrostyryl)-3,3'-dimethoxy-[1,1'-biphenyl]-4-yl)vinyl)-2-nitrophenyl) propan-1-ol (14)

Compound 13 (754 mg, 1.0082 mmol, 100 mol %), compound 2 (912 mg, 3.5065 mmol, 348 mol %), palladium (II) acetate (80 mg, 0.3563 mmol, 35 mol %), potassium carbonate (310 mg, 2.2430 mmol, 222 mol %) and tetrabutylammonium bromide (330 mg, 1.0237 mmol, 102 mol %) were placed in a high-pressure vessel. Anhydrous DMF (15 mL) was added to dissolve the reaction mixture. The high-pressure vessel was sealed, and the reaction mixture was heated to 110° C. for 12 h. After that, the reaction mixture was cooled to room temperature and diluted with EtOAc (100 mL). The insoluble materials were removed by filtration and the filtrate was washed with $H_2O$ (10 mL×3). The organic phase was collected and concentrated under reduced pressure. The residue was purified on a silica gel column, isocratic eluting with DCM containing 1% $Et_3N$. The solvent was removed under reduced pressure and the product was obtained as an orange solid 14 (450 mg, 0.4854 mmol, yield=48%).

Figure 15A:
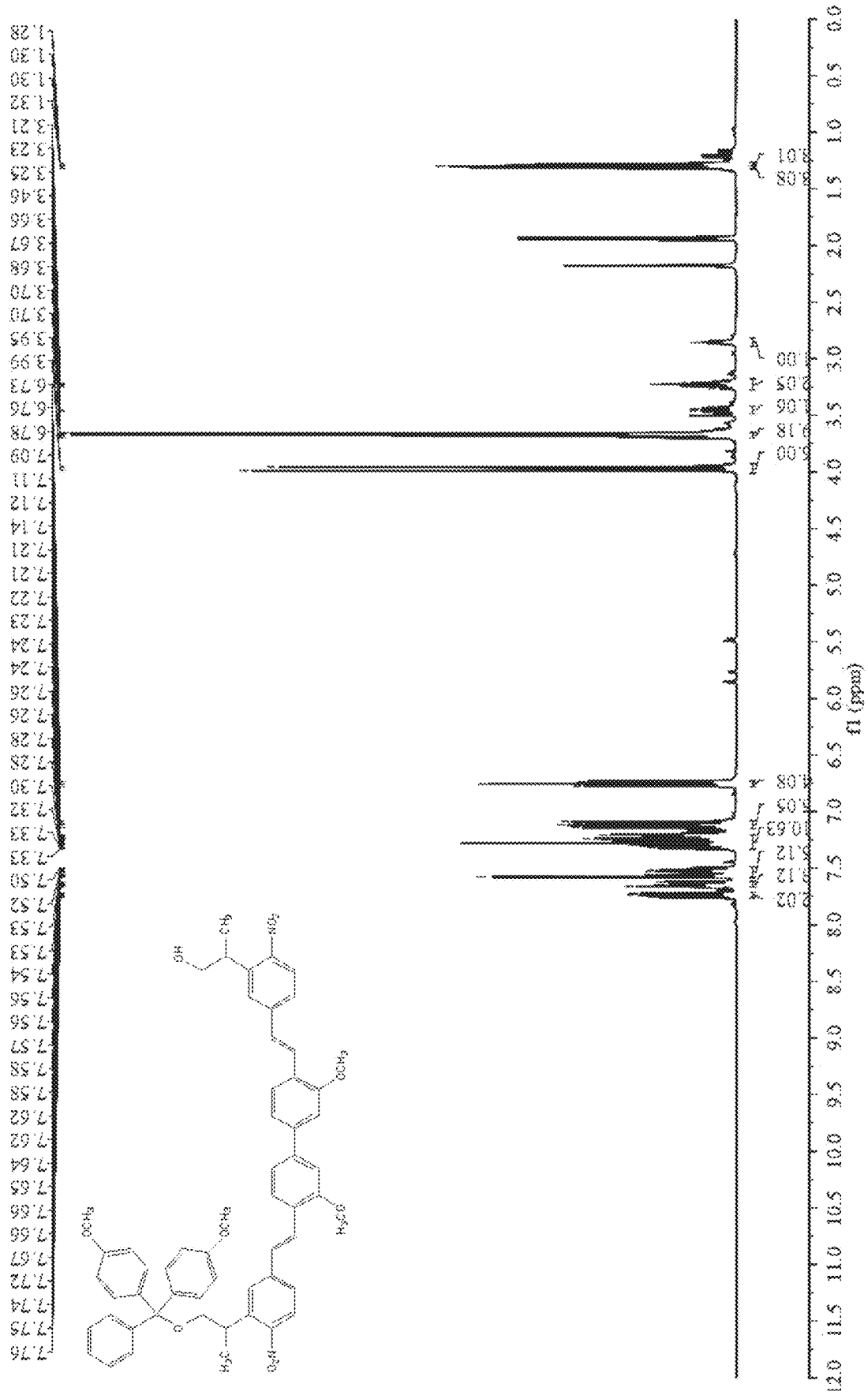
FIG. 15A displays the ¹H NMR spectra of 2-(5-((E)-2-(4'-((E)-3-(1-(Bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propan-1-ol (14).
Figure 15B:
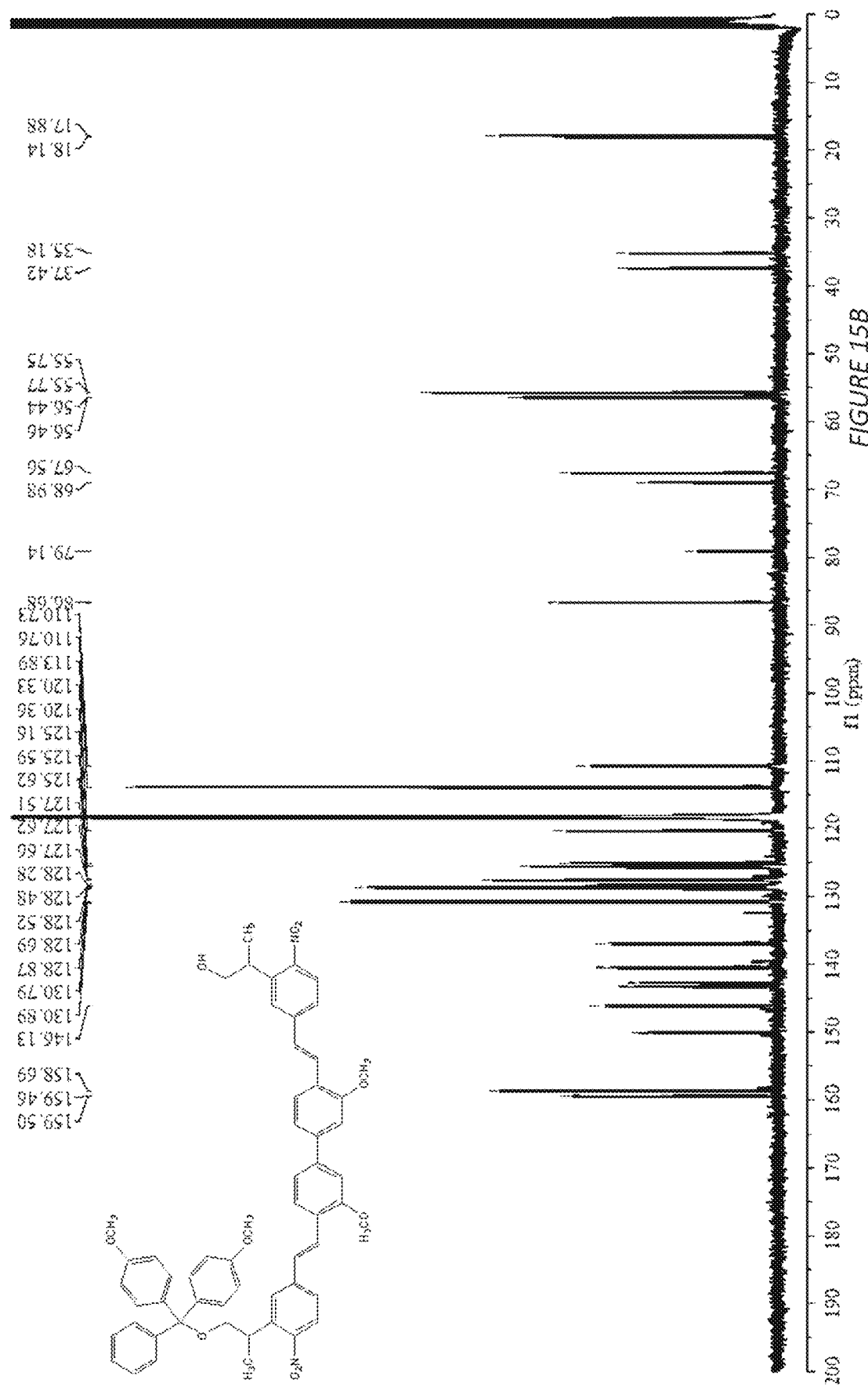
FIG. 15B displays the ¹³C NMR spectra of 2-(5-((E)-2-(4'-((E)-3-(1-(Bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propan-1-ol (14).

$^1$H, and $^{13}$C NMR spectra of (14) are presented in FIG. 15. $^1$H NMR (400 MHz, CD$_3$CN) δ 7.74 (dd, J=8.4, 5.9 Hz, 2H), 7.67-7.62 (m, 3H), 7.59-7.49 (m, 5H), 7.34-7.20 (m, 10H), 7.12 (dd, J=12.5, 9.0 Hz, 5H), 6.75 (t, J=8.6 Hz, 4H), 3.97 (d, J=13.0 Hz, 6H), 3.71-3.65 (m, 9H), 3.45 (dd, J=13.5, 6.9 Hz, 1H), 3.28-3.17 (m, 2H), 2.86 (t, J=5.6 Hz, 1H), 1.31 (d, J=6.9 Hz, 3H), 1.29 (d, J=7.0 Hz, 3H); $^{13}$C NMR (101 MHz, CD$_3$CN) δ 159.50, 159.46, 158.69, 150.17, 150.06, 146.13, 143.35, 143.24, 142.74, 142.71, 140.56, 140.44, 137.01, 136.84, 130.89, 130.79, 128.87, 128.69, 128.52, 128.48, 128.28, 128.24, 127.66, 127.62, 127.51, 125.81, 125.76, 125.62, 125.59, 125.51, 125.16, 120.36, 120.33, 113.89, 110.76, 110.73, 86.68, 79.14, 68.98, 67.56, 56.46, 56.44, 55.77, 55.75, 37.42, 35.18, 18.14, 17.88.

2-(5-((E)-2-(4'-((E)-3-(1-(bis(4-methoxyphenyl) (phenyl)methoxy)propan-2-yl)-4-nitrostyryl)-3,3'-dimethoxy-[1,1'-biphenyl]-4-yl)vinyl)-2-nitrophenyl) propyl (2-cyanoethyl) diisopropylphosphoramidite (15)

Compound 14 (300 mg, 0.3236 mmol, 100 mol %) and 5-ethylthio-1H-tetrazole (70 mg, 0.5378 mmol, 166 mol %) were placed in a round bottom flask and dissolved in a mixture of anhydrous ACN (4 mL) and anhydrous THF (1 mL). Compound 4 (0.26 mL, 0.8186 mmol, 253 mol %) was then added to the reaction mixture and stirred at room temperature for overnight. After that, the crude mixture was directly loaded on a silica gel column and the product was isocratic eluting with DCM containing 1% Et$_3$N. The solvent was removed under reduced pressure and the product was obtained as an orange solid 15 (120 mg, 0.1065 mmol, yield=33%). The dried product was stored at −20° C. and under N$_2$ atmosphere.

Figure 16A:
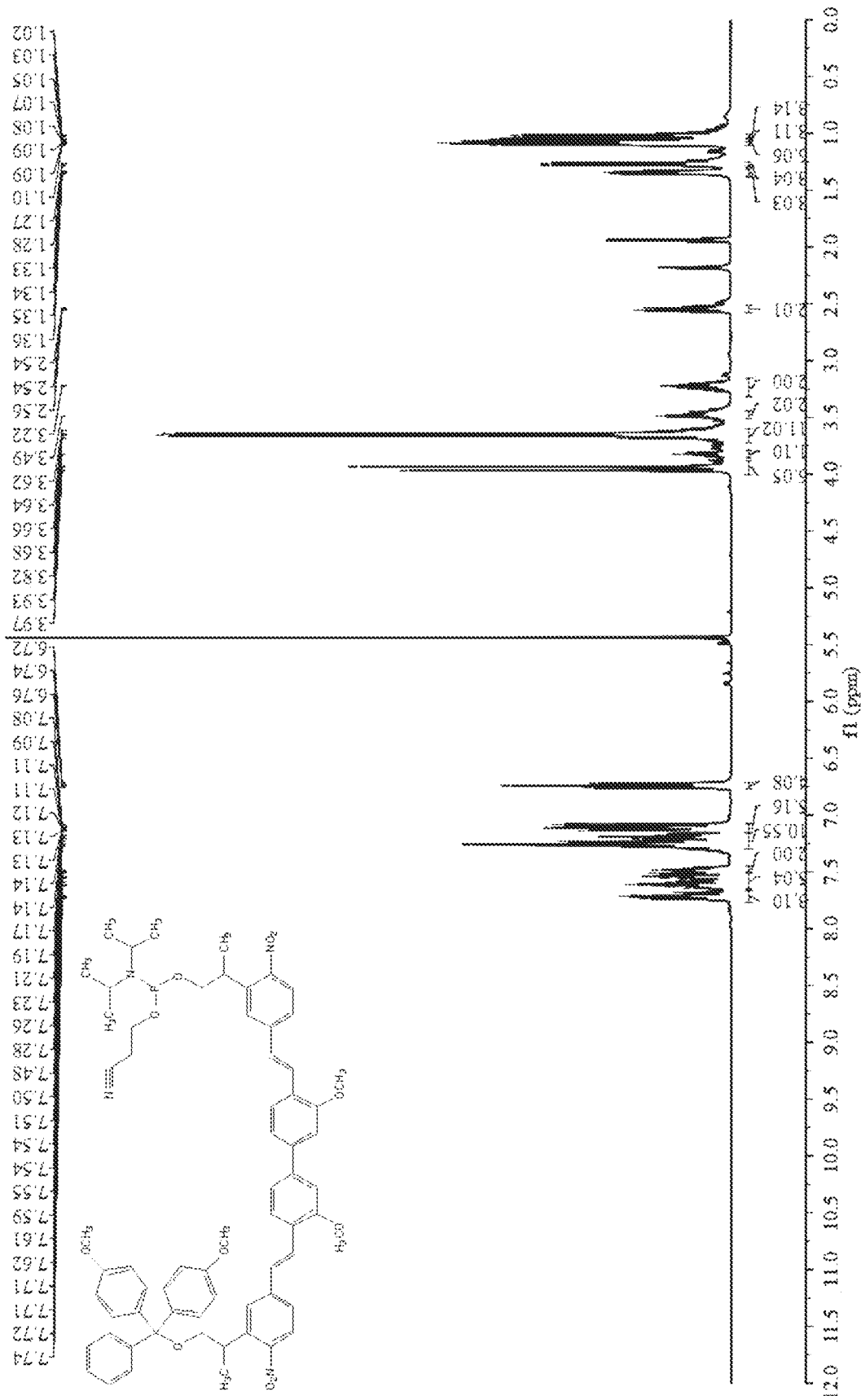
FIG. 16A displays the ¹H NMR spectra of 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl (2-cyanoethyl) diisopropylphosphoramidite (15).
Figure 16B:
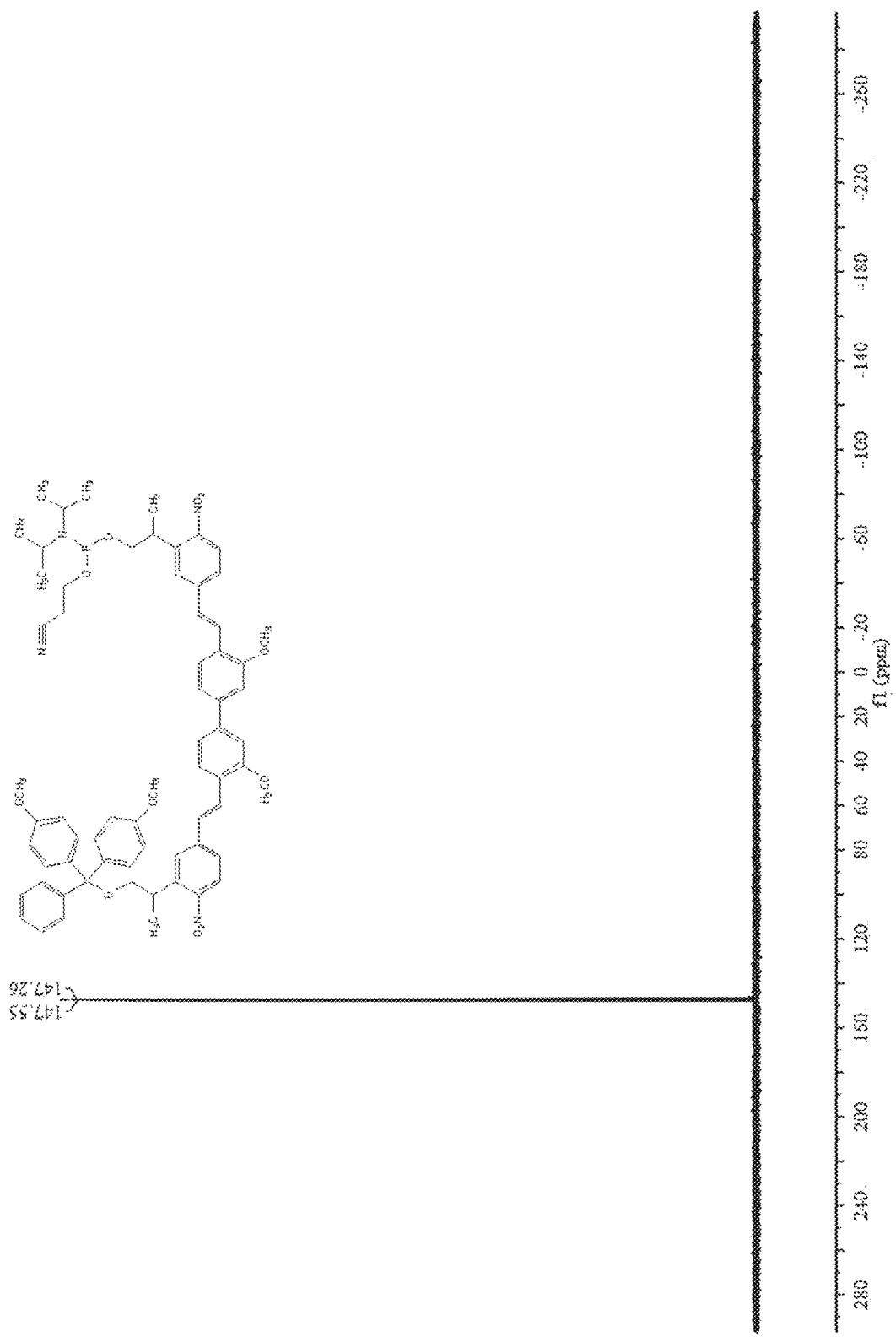
FIG. 16B displays the ³¹P NMR spectra of 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl (2-cyanoethyl) diisopropylphosphoramidite (15).
Figure 16C:
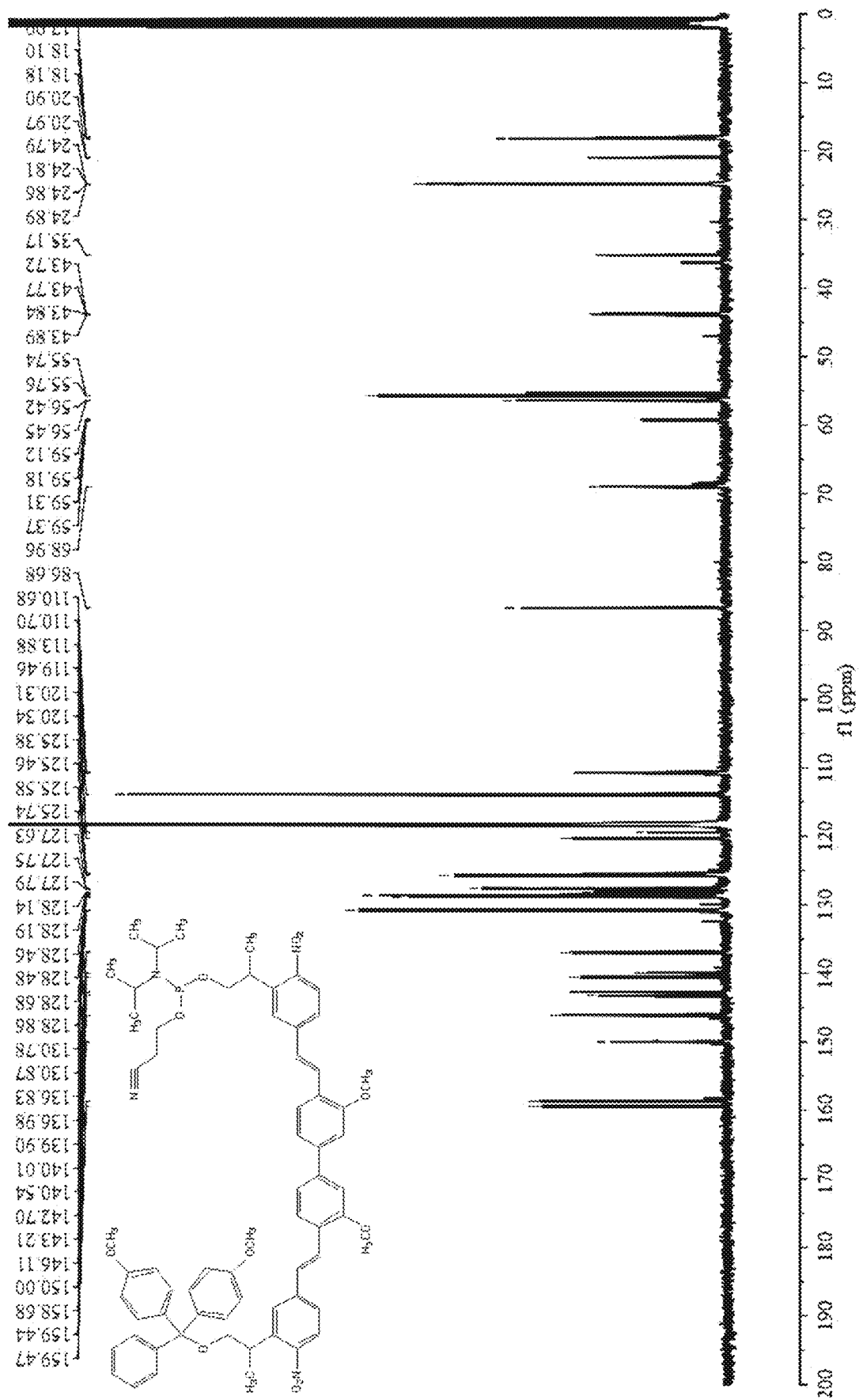
FIG. 16C displays the ¹³C NMR spectra of 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl (2-cyanoethyl) diisopropylphosphoramidite (15).

$^1$H, $^{31}$P and $^{13}$C NMR spectra of (15) are presented in FIG. 16. $^1$H NMR (400 MHz, CD$_3$CN) δ 7.71 (ddd, J=13.6, 9.0, 2.4 Hz, 3H), 7.65-7.51 (m, 5H), 7.48 (t, J=7.0 Hz, 2H), 7.22 (dt, J=14.9, 8.1 Hz, 10H), 7.15-7.07 (m, 5H), 6.74 (t, J=8.3 Hz, 4H), 3.95 (d, J=13.8 Hz, 6H), 3.82 (t, J=6.7 Hz, 1H), 3.70-3.59 (m, 11H), 3.48 (ddd, J=12.9, 6.9, 3.6 Hz, 2H), 3.28-3.18 (m, 2H), 2.55 (dt, J=8.5, 6.0 Hz, 2H), 1.35 (dd, J=6.9, 3.8 Hz, 3H), 1.27 (d, J=7.0 Hz, 3H), 1.09 (dd, J=6.7, 4.7 Hz, 6H), 1.06 (d, J=6.8 Hz, 3H), 1.02 (d, J=6.8 Hz, 3H); $^{31}$P NMR (162 MHz, CD$_3$CN) δ 147.55, 147.26; $^{13}$C NMR (101 MHz, CD$_3$CN) δ 159.47, 159.44, 158.68, 150.00, 149.91, 149.83, 146.11, 143.38, 143.36, 143.21, 142.70, 140.54, 140.01, 139.90, 136.98, 136.83, 130.87, 130.78, 128.86, 128.68, 128.48, 128.46, 128.19, 128.14, 127.79, 127.75, 127.63, 125.74, 125.58, 125.46, 125.38, 120.34, 120.31, 119.46, 113.88, 110.70, 110.68, 86.68, 68.96, 59.37, 59.31, 59.18, 59.12, 56.45, 56.42, 55.80, 55.76, 55.74, 43.89, 43.84, 43.77, 43.72, 35.17, 24.89, 24.86, 24.81, 24.79, 20.97, 20.90, 18.18, 18.10, 17.99.

Synthesis of Photocleavable DNA Oligonucleotides

Oligonucleotide synthesis was performed on 500 nmole scale using an automated oligonucleotide synthesizer and standard cyanoethylphosphoramidite chemistry, starting from the 1000 Å universal CPG solid support. Commercially available DNA nucleoside phosphoramidites, BNSF phosphoramidite and BNSMB phosphoramidite were site-specifically coupled onto the growing oligonucleotides chain as an artificial base with a prolonged detritylation and coupling time. To synthesize the photocleavable DNA oligonucleotides in a quantitative yield and with high purity, the synthetic protocol is optimized accordingly from standard method recommended by the synthesizer manufacturer. For instance, in each synthetic cycle, the frequencies of the de-blocking and coupling reactions are increased by 3 and 2 times, respectively. Additionally, the duration of each de-blocking reaction is extended from 30 s to 12 min while the duration of each coupling reaction is also extended from 60 s to 15 min. The coupling efficiency was monitored by the trityl concentration level. The DNA oligonucleotides were fully deprotected in concentrated ammonium hydroxide at 55° C. for 48 h.

Figure 17:
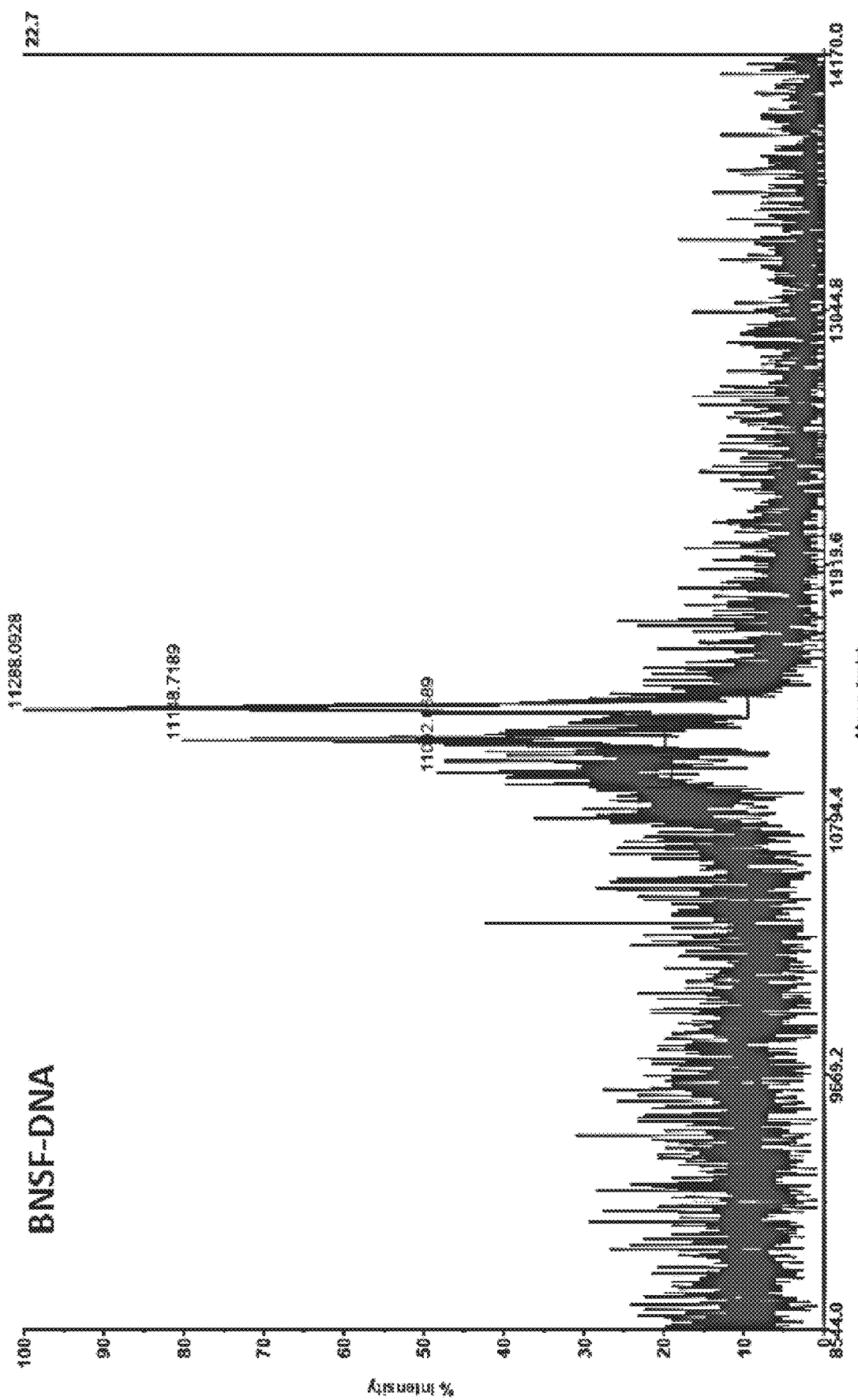
FIG. 17 displays the mass spectrum for BNSF-DNA conjugate.
Figure 18:
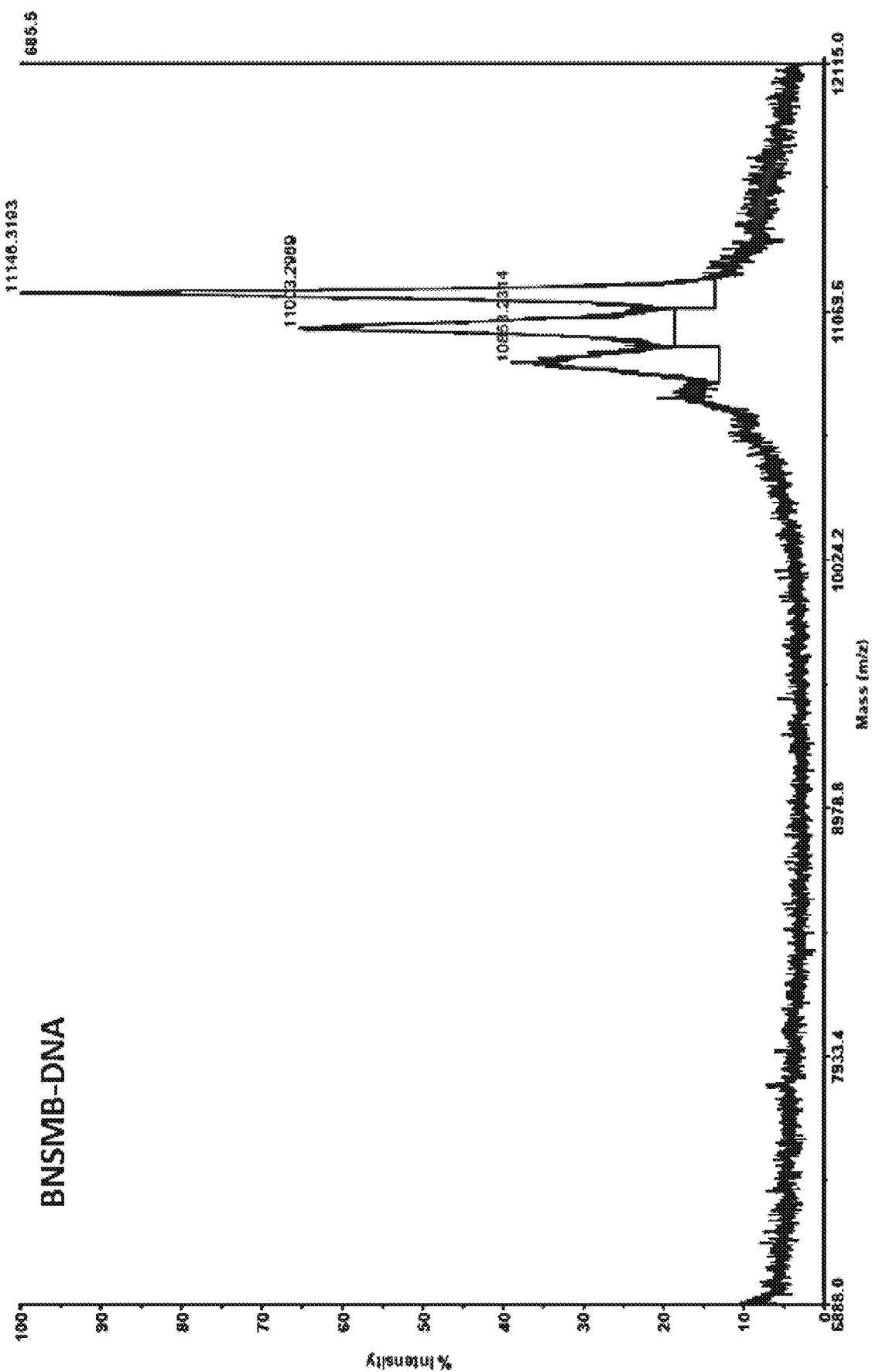
FIG. 18 displays the mass spectrum for BNSMB-DNA conjugate.
Figure 19:
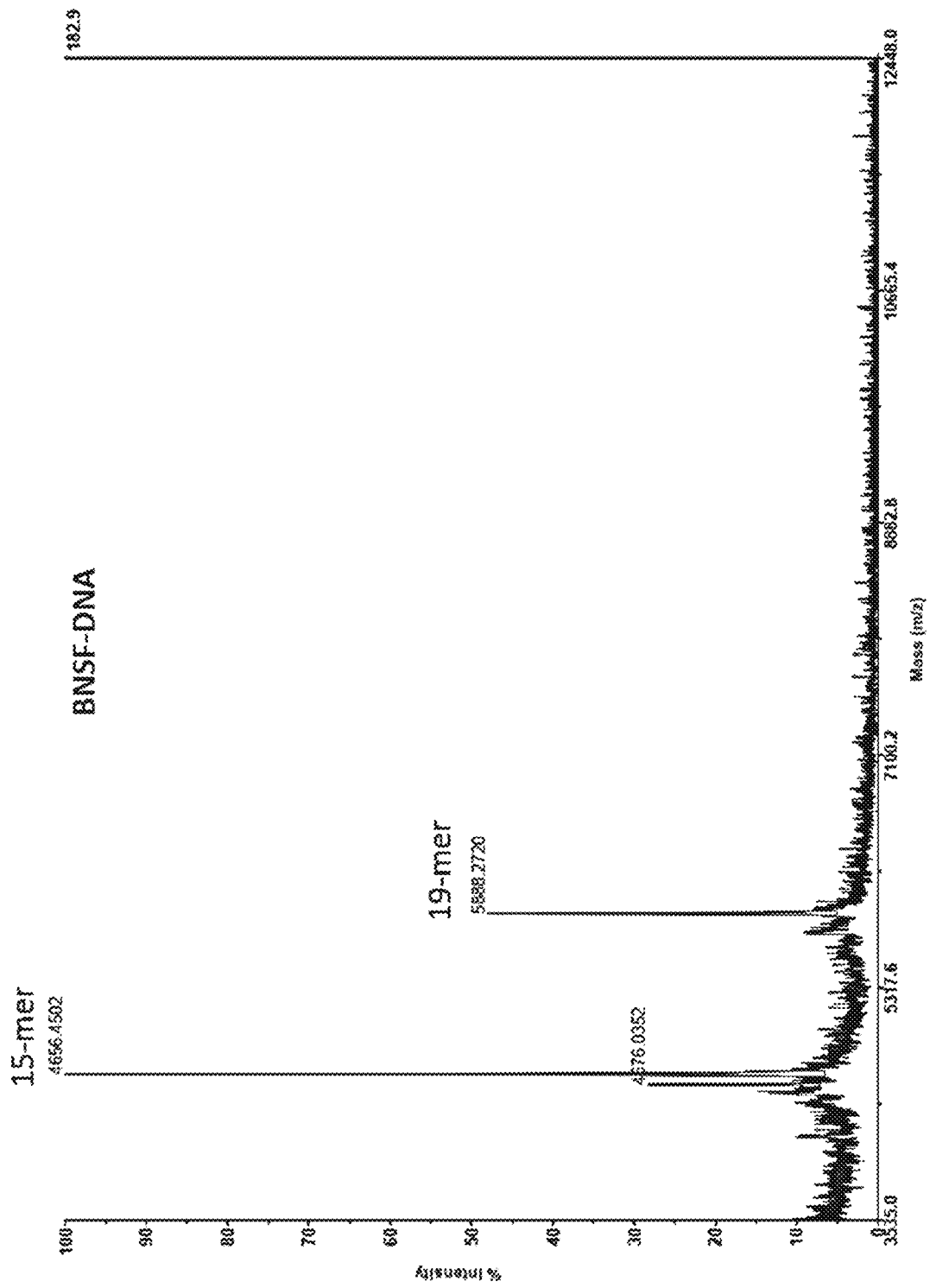
FIG. 19 displays the mass spectrum of BNSF-DNA conjugate after fragmentation by NIR light.
Figure 20:
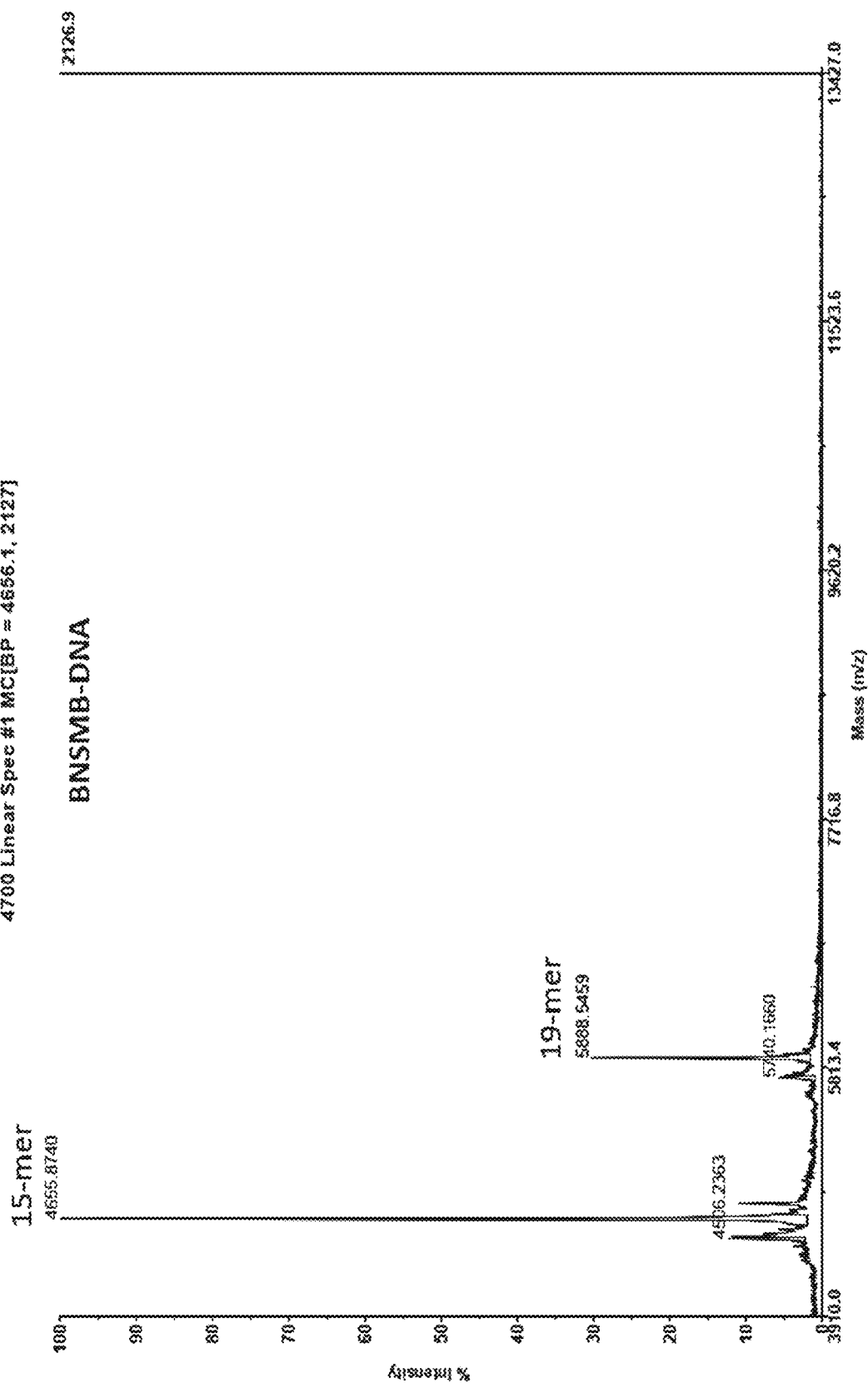
FIG. 20 displays the mass spectrum of BNSMB-DNA conjugate after fragmentation by NIR light.

Crude DNA oligonucleotides were purified on 15% polyacrylamide/8M urea polyacrylamide gels at constant current of 30 mA for 3 h (30 min at 250V followed by 2.5 hr at 500 V), using 1 X TBE buffer. After electrophoresis, the plates were wrapped in plastic and placed on a fluorescent TLC plate and then illuminated with a UV lam at 254 nm. The bands were excised quickly, and the selected gel pieces were crushed and incubated in 12 mL of sterile water at 55° C. for 24 h. The samples were dried to about 1 mL, desalted using Sephadex G-25 column chromatography. Quantification is carried by UV/Vis analysis. The formation of the BNSF-DNA, sequence shown in SEQ ID NO:1 and SEQ ID NO:2, and BNSMB-DNA, sequence shown in SEQ ID NO:3 and SEQ ID NO: 4, is confirmed by MALDI-TOF analysis as shown in Table 1. The MALDI-TOF mass spectrum for BNSF-DNA of m/z calcd 11248.4652; found, 11288.0928 [M]+ while for BNSMB-DNA of m/z calcd 11092.2402; found, 11146.3193 [M]+ are shown in FIGS. 17-18. FIGS. 19 and 20 display the mass spectrum of BNSF-DNA conjugate and BNSMB-DNA conjugate after fragmentation by NIR light.

13.5% Denaturing PAGE was set according to the standard protocol, and the running time is about 1-1.5 h with 30 mA power supply. Stain-All was used to stain the DNA strands.

TABLE 1

Sequences and mass analysis of the BNSF-DNA and BNSMB-DNA before and after photolysis.

| Sample | Sequences 5' to 3' | Before photolysis | | After photolysis | | | |
|---|---|---|---|---|---|---|---|
| | | | | 5'-CTGAGACTTT AATAA | | TTGAAATTCACCT GGTAGC-3' | |
| | | Found mass/g/mol | Calculated mass/g/mol | Found mass/g/mol | Calculated mass/g/mol | Found mass/g/mol | Calculated mass/g/mol |
| BNSF-DNA | CTGAGACTTTAATAA-BNSF-TTGAAATTCACCTGGTAGC | 11288.0928 | 11282.7187 | 4656.4502 | 4655.0324 | 5588.2720 | 5882.8024 |
| BNSMB-DNA | CTGAGACTTTAATAA-BNSMB-TTGAAATTCACCTGGTAGC | 11146.3193 | 11126.4937 | 4655.8740 | 4655.0324 | 5888.5459 | 5882.8024 |

Figure 21A:
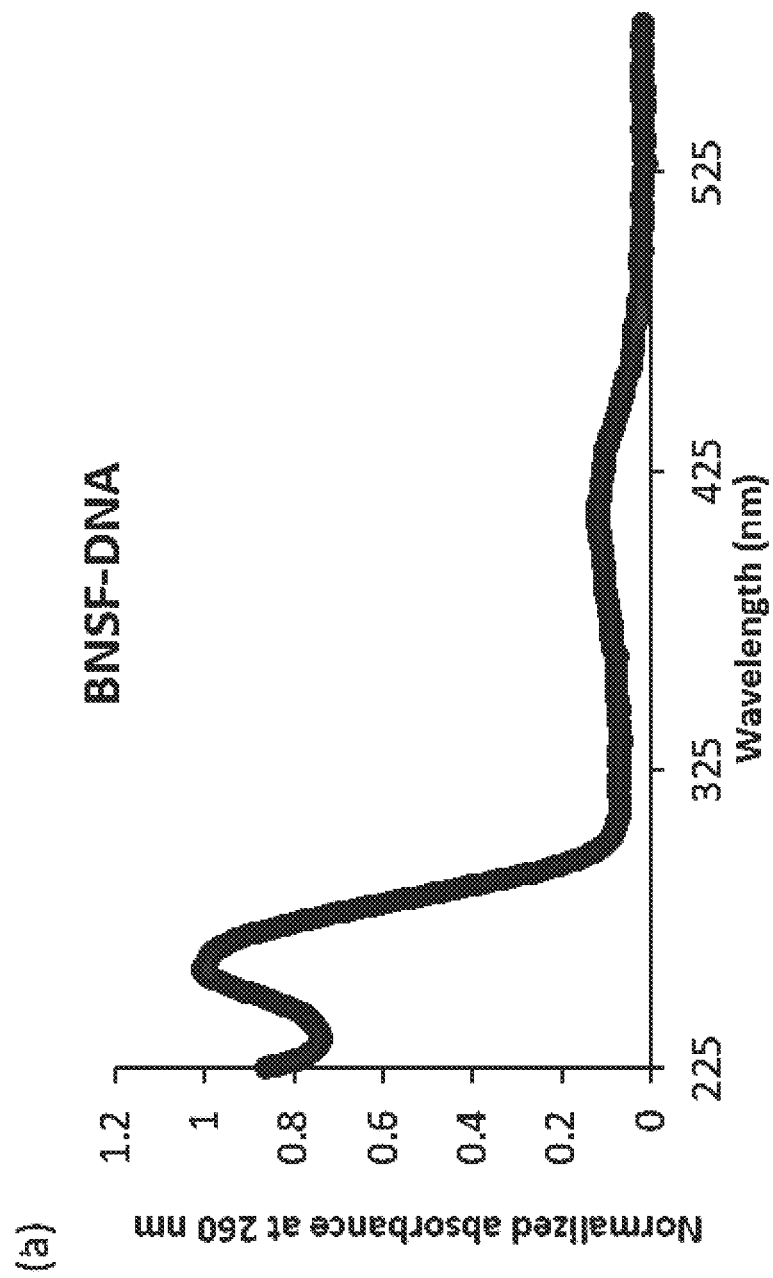
FIGS. 21A-21F display the UV/Vis spectra of (a) BNSF-DNA and (b) BNSMB-DNA, BNSF-DNA and BNSMB-DNA after photolysis at (c-d) 405 nm and (e-f) 700 nm as a function of irradiation time respectively.
Figure 21B:
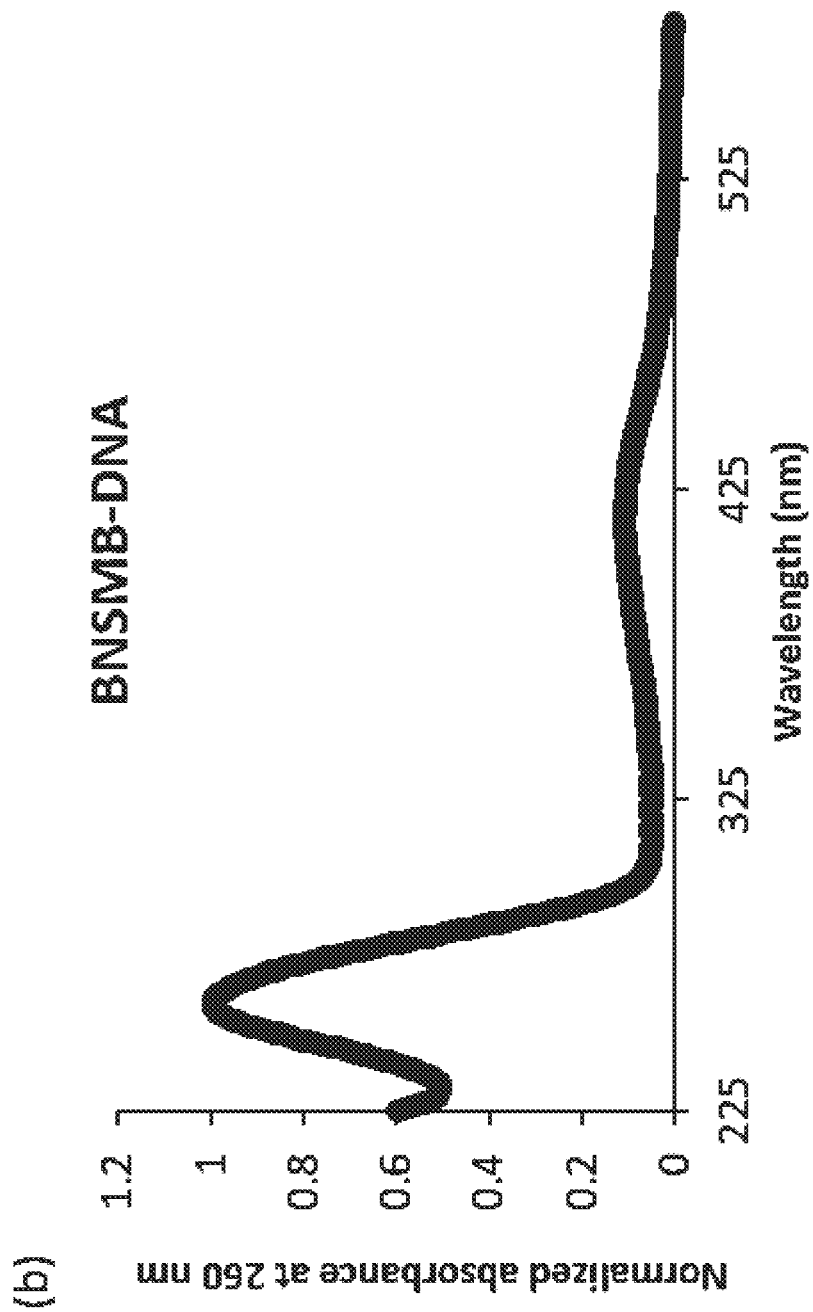

The photophysical properties of the conjugates were investigated by UV/Visible spectroscopy. As shown in FIGS. 21A and 21B, before photocleavage, the one-photon absorption spectra of BNSF- and BNSMB-containing oligonucleotides shows an additional red shifted UV/Vis absorption band with wavelength at ~405 nm and 415 nm respectively which results from the π-π* transitions of the corresponding chromophores on top of the UV/Vis absorption band of nucleobases at 260 nm. BNSF and BNSMB are two well-known uncaging highly conjugated chromophores for two-photon applications. Their two-photon uncaging action cross section of 5.0 and 0.9 GM were determined respectively by Nicoud and his co-workers at 800 nm. They are pretty much higher than those of reported photon-sensitive photoremovable groups such as 2-nitrobenzyl or NPPOC units which exhibit two-photon uncaging action cross section of 0.01 GM or even less at 800 nm.

Figure 21C:
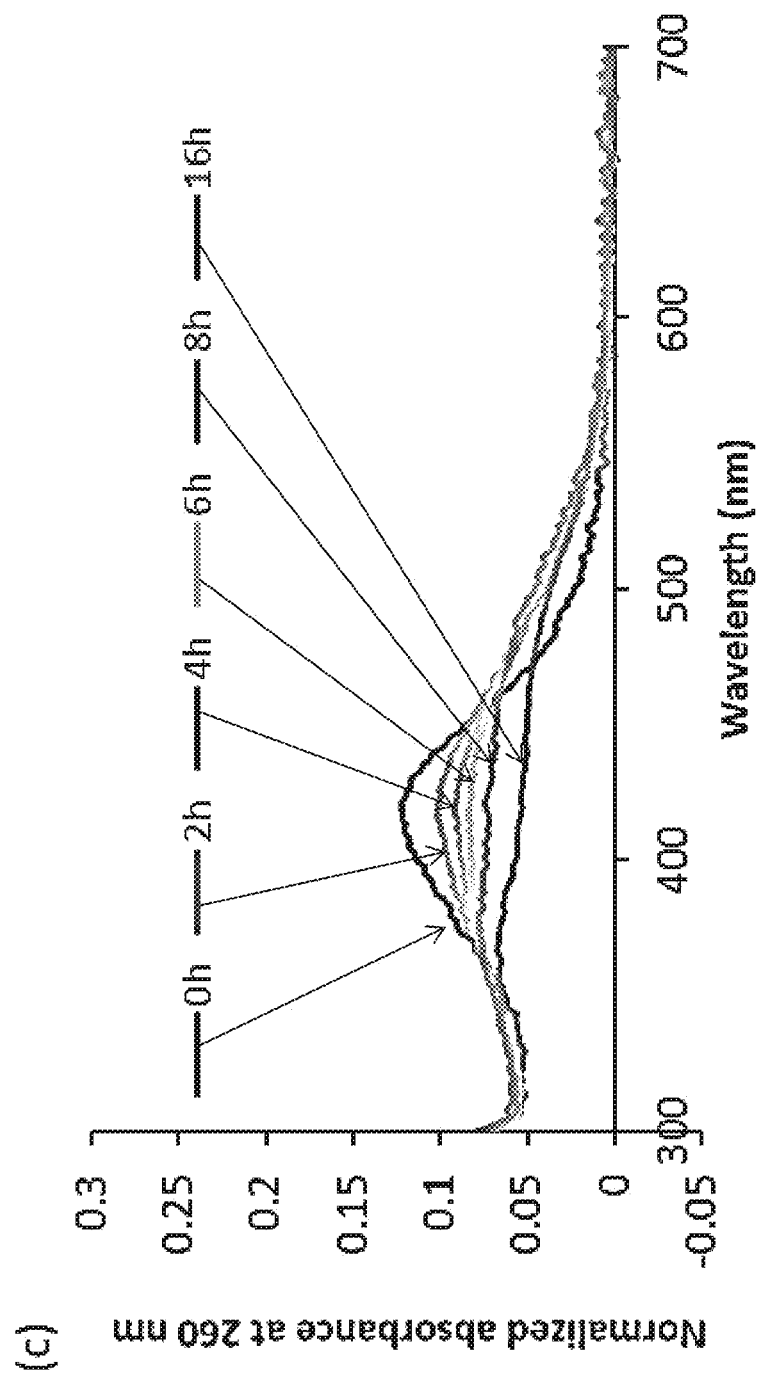
Figure 21D:
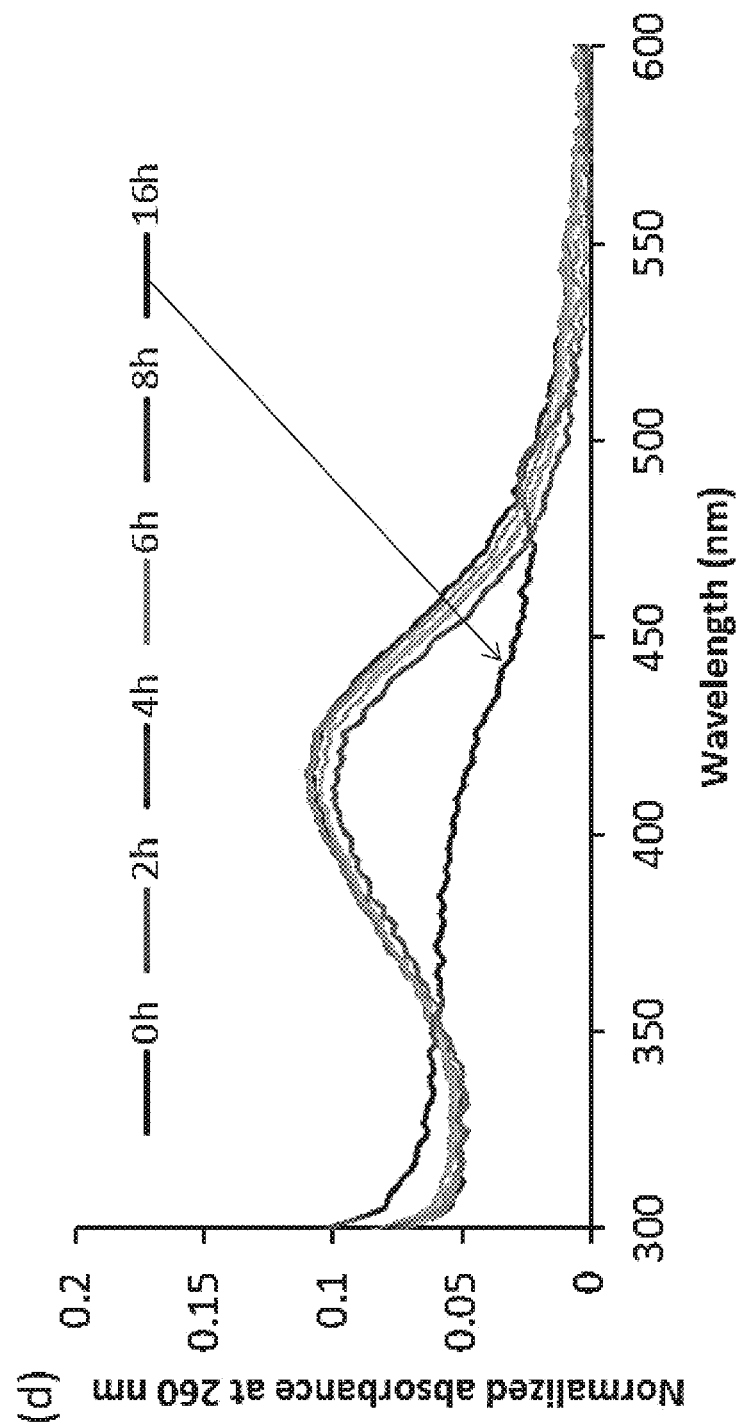
Figure 21E:
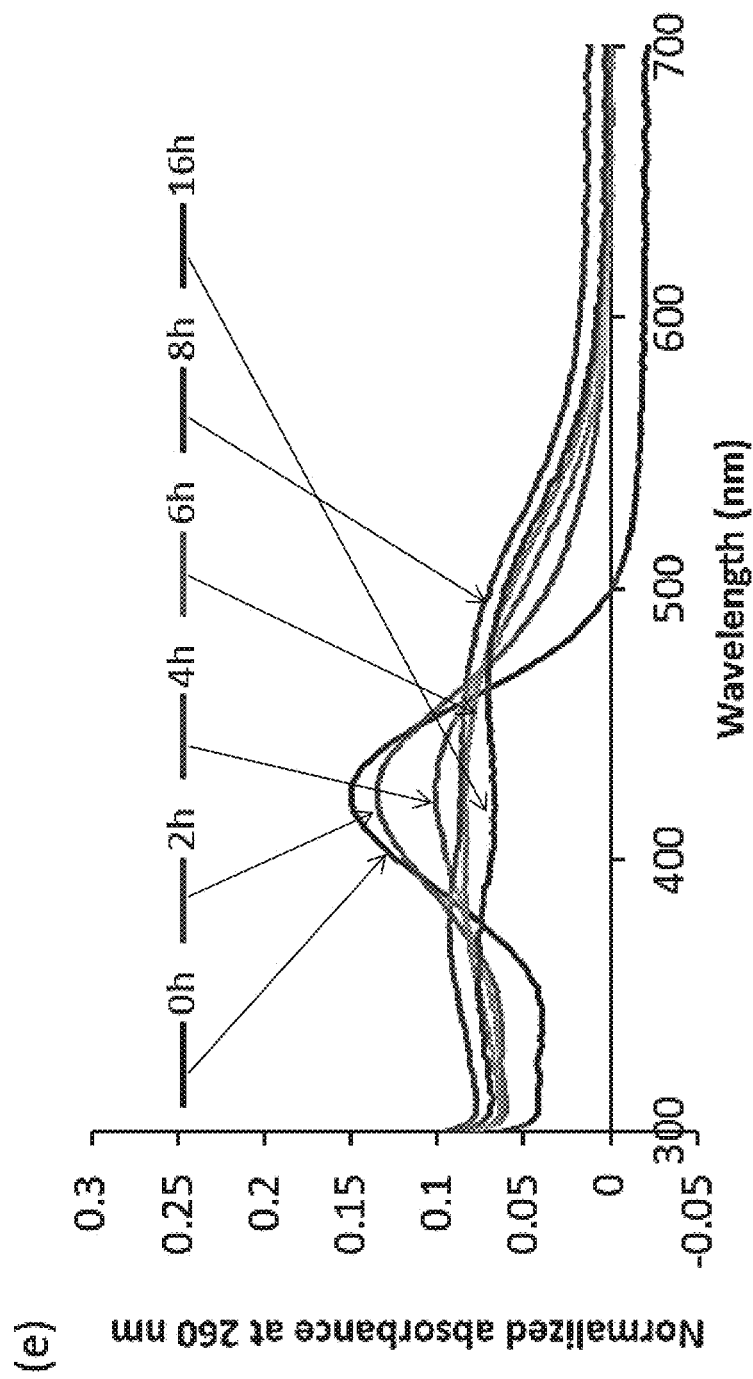
Figure 21F:
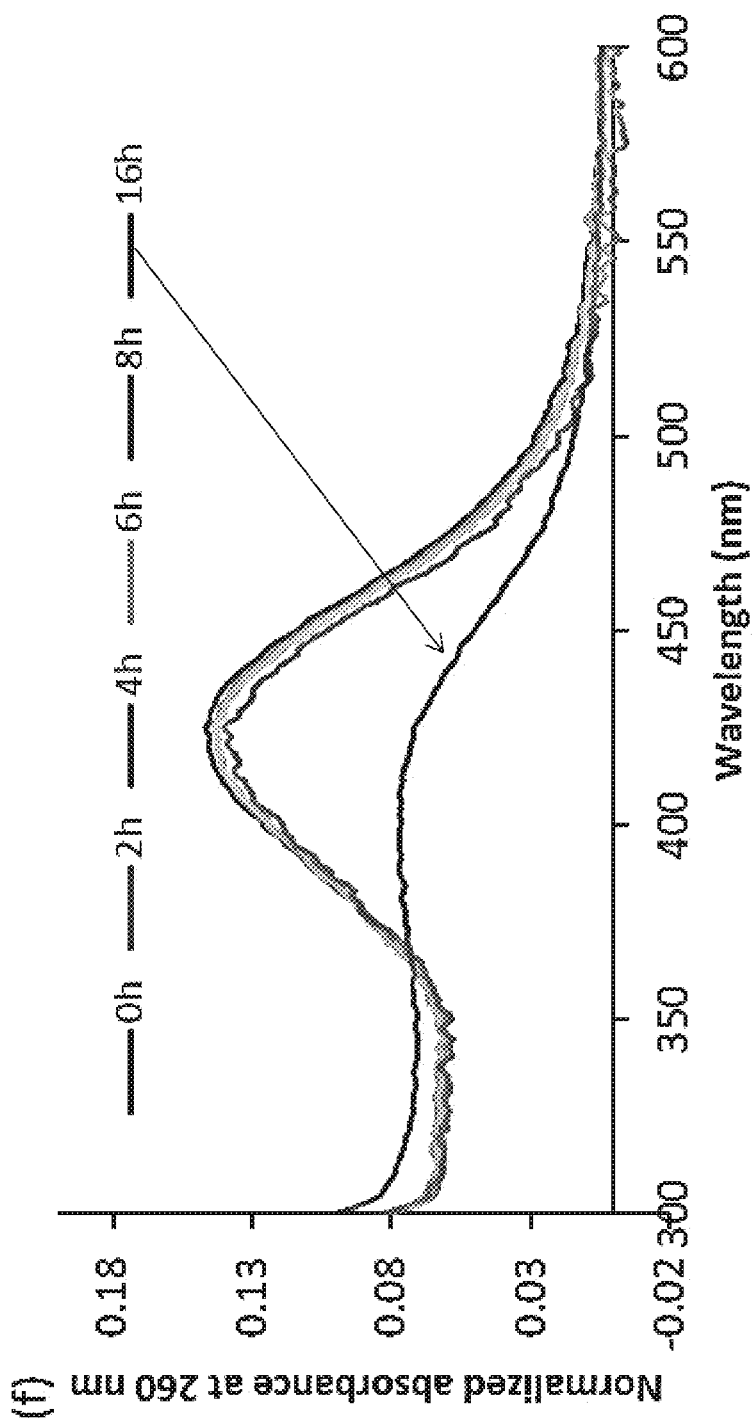

To investigate their photochemical properties, photolysis was conducted by irradiation of the designed oligonucleotides (~0.2 μM) at wavelength 405 nm under 25 mW or 700 nm under 1 mW in phosphate buffer at pH 7.4. The UV/Vis spectra shown in FIGS. 21C and 21D after photolysis show similar decrease in absorbance at 405 nm (for BNSF-DNA) and 415 nm (for BNSMB-DNA) and increase in absorbance at 490 nm (for BNSF-DNA and BNSMB-DNA) upon photolysis as a function of irradiation time with 405 nm light. In contrast, there is not much change in the UV/Vis absorption maxima of BNSF-DNA and BNSMB-DNA until photolysis under 700 nm light for longer than 8 h (FIGS. 21E and 21F). Even though the photocleavage molecules was optimized for two-photon uncaging, they still exhibit great sensitivities toward one-photon absorption.

Figure 23B:
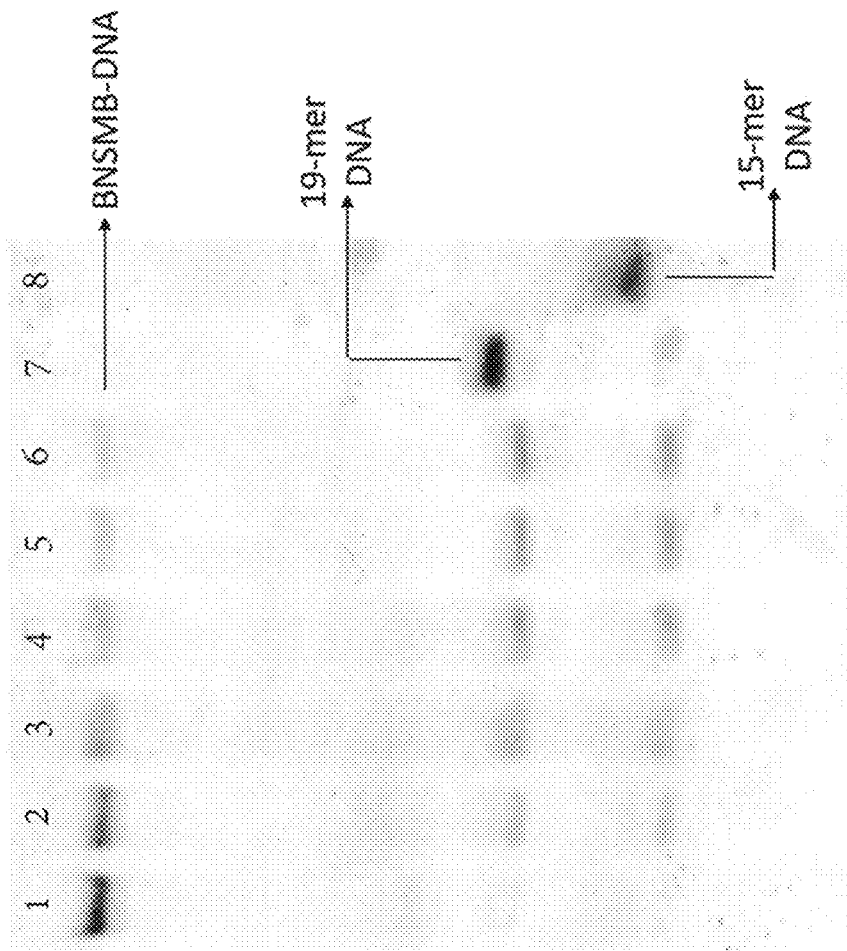
FIGS. 23A and 23B are PAGE analysis of the photocleavable DNA conjugates upon UV light (405 nm) irradiation.
Figure 23A:
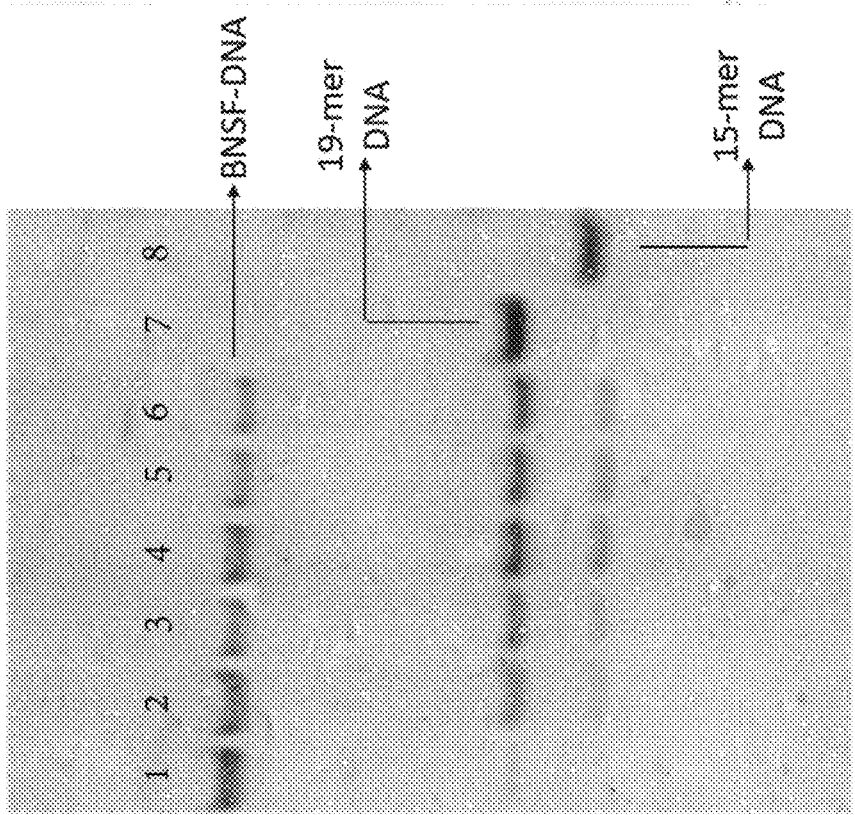

Polyacrylamide gel electrophoresis (PAGE) analysis was also used to confirm the photocleavage of the designed oligonucleotides BNSF-DNA and BNSMB-DNA into two shorter fragments. As shown in FIGS. 22A and 22B, the BNSF-DNA and BNSMB-DNA (lane 1) break into two fragments (lane 2) in which their molecular sizes are equivalent to the 19- and 15-mer of DNA strands (lane 3 and 4) after irradiating with 700 nm light. Similar results were obtained when the DNA samples were irradiated with 405 nm light at different time points (FIGS. 23A and 23B). These results are in good agreement with our designed caged DNA fragments, confirming the occurrence of bond breaking only in the photoliable NPPOC units.

Figure 24A:
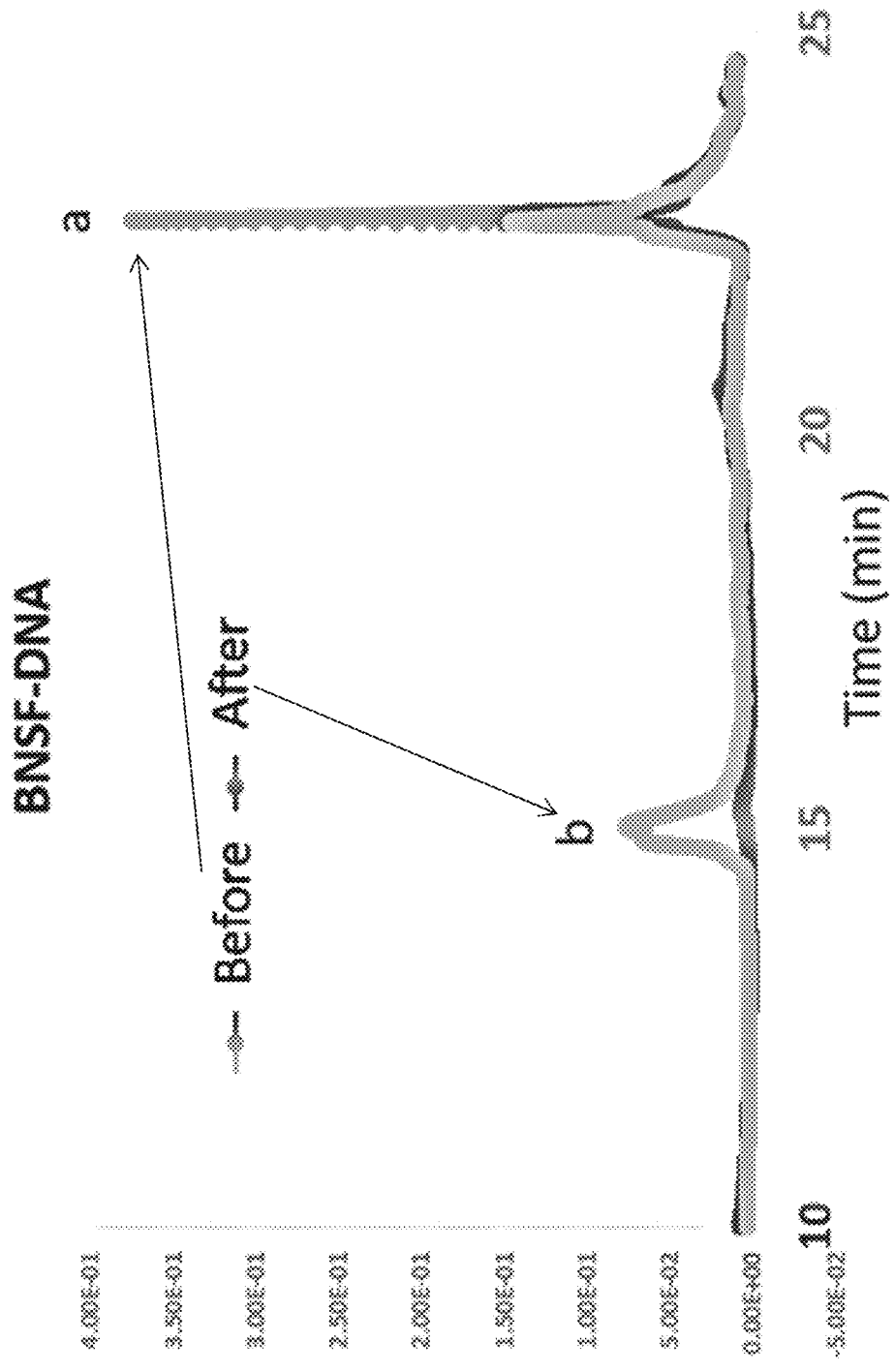
FIGS. 24A and 24B are HPLC chromatogram of BNSF-DNA and BNSMB-DNA conjugates before and after NIR light (700 nm) irradiation.
Figure 24B:
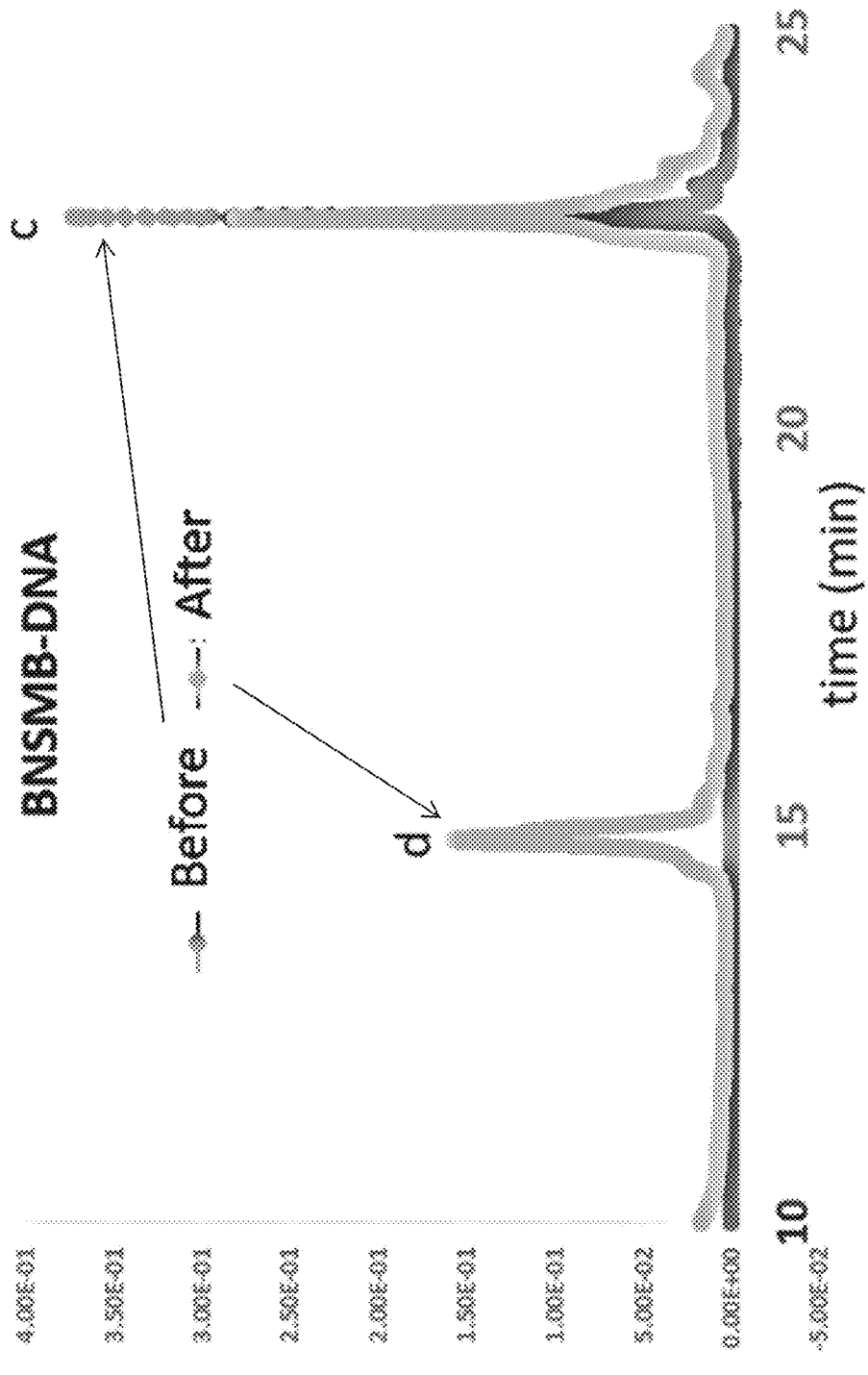
Figure 25A:
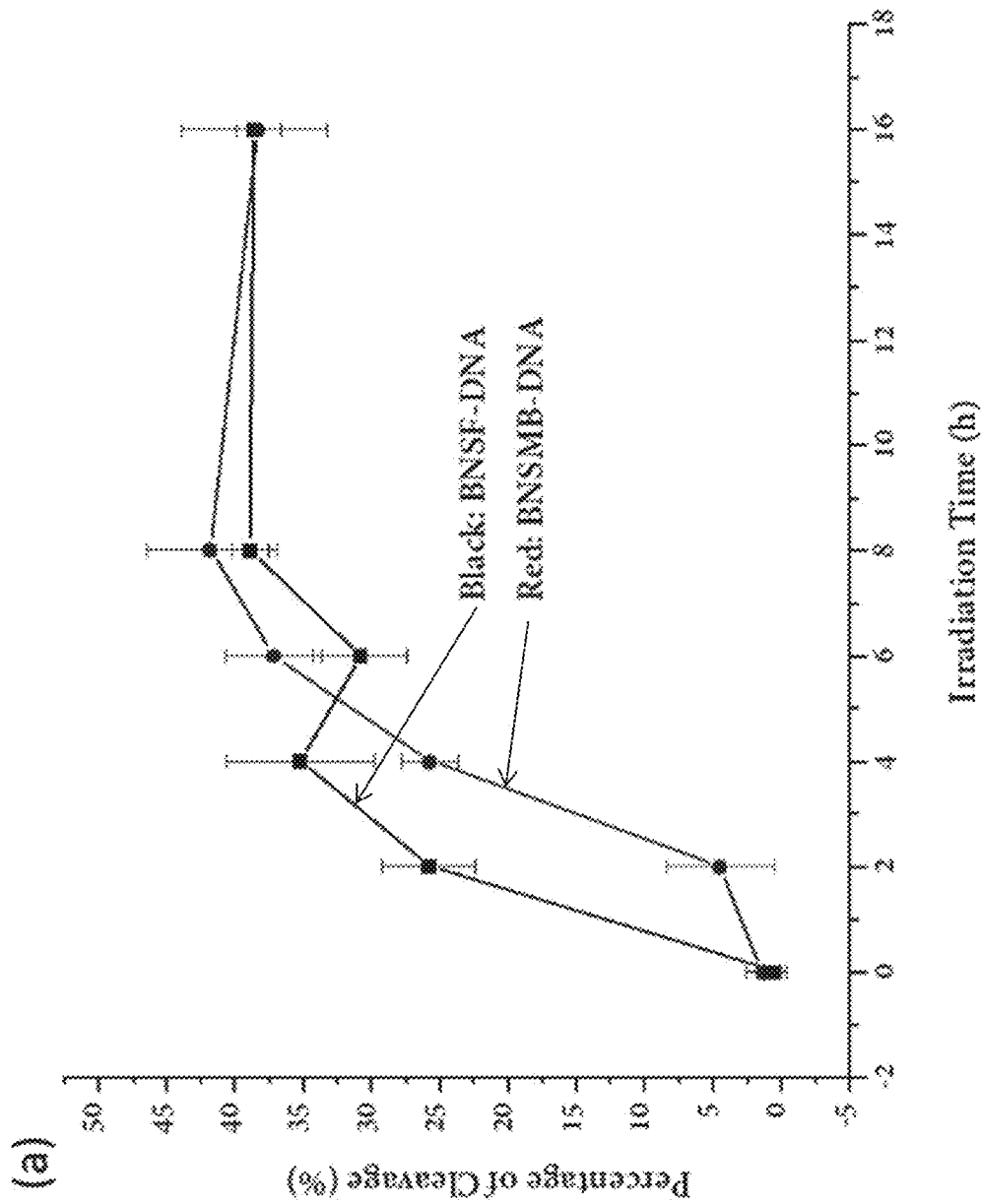
FIG. 25A is a graph of the percentage cleavage as a function of irradiation (UV light) time.
Figure 25B:
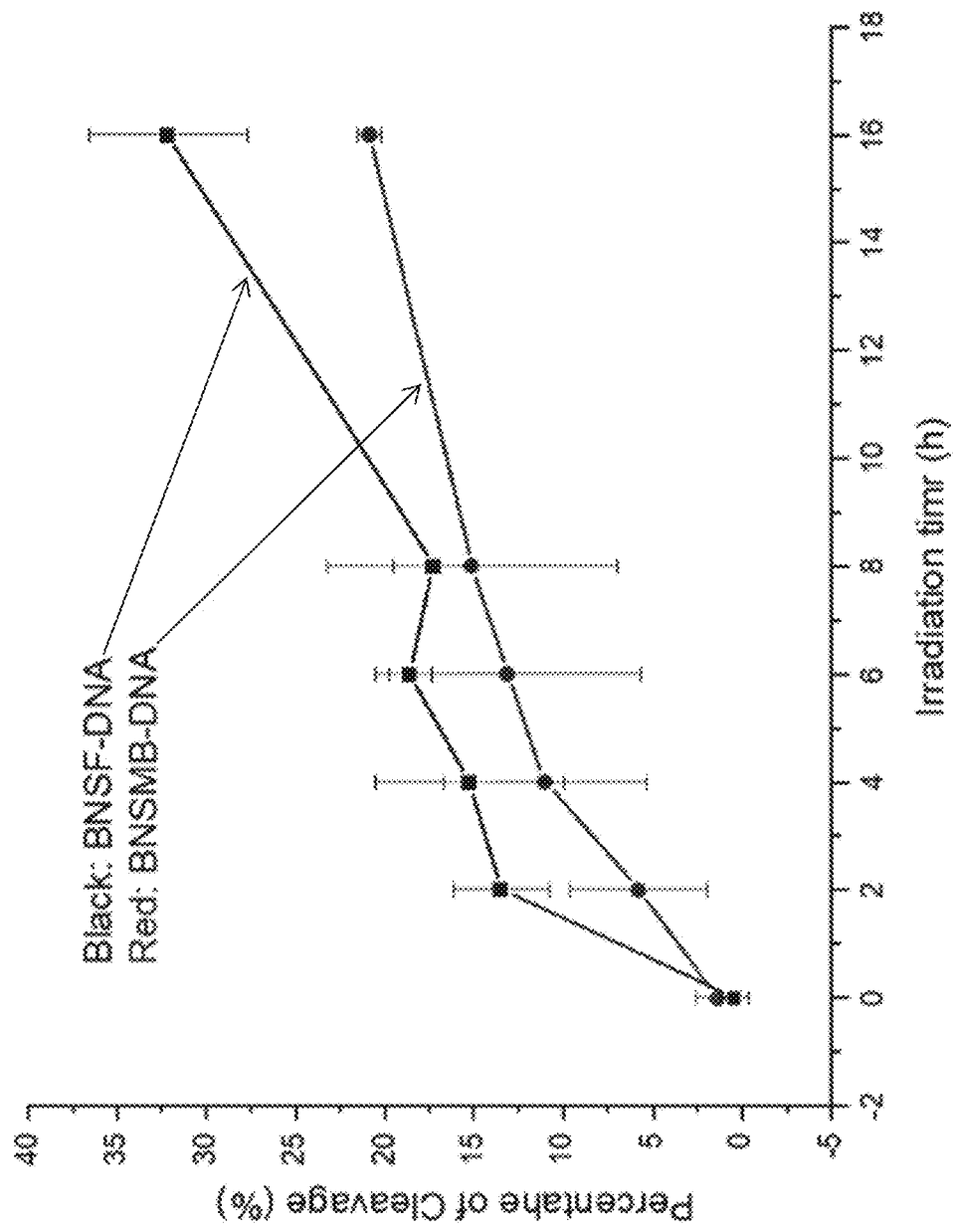
FIG. 25B is a graph of the percentage cleavage as a function of irradiation (NIR light) time.

The photolytic release of caged DNAs was analysed quantitatively by reversed-phase high-performance liquid chromatography (RP-HPLC). FIGS. 24A and 24B and Table 1 shows the HPLC results of non-irradiated and irradiated samples. The non-irradiated sample a or c and the resulting photoproduct b or d were characterized by mass spectroscopy. As expected, the additional HPLC peak at 14.9 min presents the photoproducts 19-mer and 15-mer of DNAs resulted from linker cleavage of BNSF-DNA and BNSMB-DNA. which are confirmed by MALDI-TOF analyses as shown in Table 1. The two shorter fragments of broken DNA strands were confirmed with their corresponding MALDI-TOF m/z peak at 4656.4502 $[M+Na]^+$ (calculated m/z 4646.9097) and m/z peak at 5888.2720 $[M+K]^+$ (calculated m/z 5870.6499) as shown in SI. It was found that the photocleavage abilities of BNSF-DNA and BNSMB-DNA were about 32±4.5% and 21±0.7% at the saturation point (FIG. 25). A control DNA with no photocleavable moieties was also irradiated in the same manner but showed no evidence of degradation over the observed time points.

The results demonstrate the design and synthesis of two phosphoramidite building blocks based on BNSF and BNSMB structures. Some common molecular intermediates have been designed and linked to the central biphenyl core of the two molecules, resulting in a versatile and cost-effective design. They can be effectively introduced to DNA oligonucleotides via the well-established standard cyanoethylphosphoramidite chemistry on the nucleic acid synthesizer. More importantly, fragmentation of these BNSF- and BNSMB-functionalized DNA strands is achieved by both one-photon and two-photon photolysis of photoliable bonds of [2-(2-nitrophenyl)propoxy]carbonyl groups on BNSF and BNSMB molecules respectively, resulting in two short pieces of single-stranded DNAs. The versatile design and facile synthesis of these two-photon photocleavage phosphoramidite molecules are beneficial to synthetic chemists and photochemists for the development of new caged compounds which enables to introduce into oligonucleotides as light-triggered carriers via solid-phase synthesis for a wide range of applications in materials science, polymer, chemistry, biology and DNA nanoecthnology.

SEQUENCE LISTING

```
<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: Linker
<222> LOCATION: (11)..(11)
<223> OTHER INFORMATION: Seq 1 is linked to Sequence 2 via the last
      residue a is linked to the first residue of sequence 2 by the
      phosphoramidite BNSF

<400> SEQUENCE: 1 ctgagactttt a                                                          11

<210> SEQ ID NO 2
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: Linker2
<222> LOCATION: (1)..(19)
<223> OTHER INFORMATION: The first residue of sequence 2 is linked to
      the last residue of sequence 1 using the phosphoramidite BNSF

<400> SEQUENCE: 2
ttgaaattca cctggtagc                                                   19

<210> SEQ ID NO 3
<211> LENGTH: 14
<212> TYPE: DNA
```

```
<213> ORGANISM: Artificial Sequence
<220> FEATURE:
<223> OTHER INFORMATION: Synthetic
<220> FEATURE:
<221> NAME/KEY: Linker
<222> LOCATION: (1)..(11)
<223> OTHER INFORMATION: Sequence 3 is linked to Sequence 4 via the
      terminal a of Sequence 3 and the initial t of Sequence 4 using the
      phosphoramidite BNSMB

<400> SEQUENCE: 3
tgagacttta ataa                                                      14

<210> SEQ ID NO 4
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: Linker
<222> LOCATION: (1)..(19)
<223> OTHER INFORMATION: Sequemce 3 is linked to Sequemce 4 via the
      terminal a of Sequemce 3 to the initial t of Sequemce 4 using the
      phosphorabidite BNSMB

<400> SEQUENCE: 4
ttgaaattca cctggtagc                                                 19
```

What is claimed is:

1. A conjugated molecule comprising a photocleavable group linked to a nucleic acid, wherein the photocleavable group is a 4,4'-bis-(8-(4-(nitro-3-(2-propyl)-styryl))-3,3'-dimethoxybiphenyl (BNSMB) group conferred by 2-(5-((E)-2-(4'-((E)-3-(1-bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl(2-cyanoethyl) diisopropylphosphoramidite coupled to the nucleic acid during synthesis of the conjugated molecule; and the conjugated molecule is capable of releasing the nucleic acid therefrom upon being exposed to near infrared (NIR) light to cleave away the photocleavable group.

2. The conjugated molecule of claim 1, wherein the nucleic acid is DNA, mRNA, miRNA, siRNA, or antisense oligonucleotide.

3. The conjugated molecule of claim 1, wherein the photocleavable group is 2-(5-((E)-2-(4'-((E)-3-(1-(bis(4-methoxyphenyl)(phenyl)methoxy)propan-2-yl)-4-nitrostyryl)-3,3'-dimethoxy-[1,1'-biphenyl]-4-yl)vinyl)-2-nitrophenyl)propyl(2-cyanoethyl) diisopropylphosphoramidite.

* * * * *